(12) United States Patent
Damm et al.

(10) Patent No.: US 9,878,127 B2
(45) Date of Patent: Jan. 30, 2018

(54) CATHETER DELIVERY SYSTEM FOR HEART VALVE PROSTHESIS

(71) Applicants: JenaValve Technology GmbH, München (DE); FRAUNHOFER-GESELLSCHAFT ZUR FÖRDERUNG DER ANGEWANDTEN FORSCHUNG E.V., München (DE)

(72) Inventors: Christoph Damm, Jena (DE); Andreas Kamm, Jena (DE); Michael Litzenburger, München (DE); Thomas Töllner, Berlin (DE)

(73) Assignees: JenaValve Technology, Inc., Irvine, CA (US); Fraunhofer-Gesellschaft Zur Förderung Der Angewandten Forschung E.V., Munich (DE)

( * ) Notice: Subject to any disclaimer, the term of this patent is extended or adjusted under 35 U.S.C. 154(b) by 0 days.

(21) Appl. No.: 14/400,893

(22) PCT Filed: Apr. 10, 2013

(86) PCT No.: PCT/EP2013/057431
§ 371 (c)(1),
(2) Date: Nov. 13, 2014

(87) PCT Pub. No.: WO2013/171007
PCT Pub. Date: Nov. 21, 2013

(65) Prior Publication Data
US 2015/0148894 A1    May 28, 2015

(30) Foreign Application Priority Data
May 16, 2012    (EP) ..................... 12168367

(51) Int. Cl.
A61F 2/24    (2006.01)
A61M 25/01    (2006.01)
A61F 2/95    (2013.01)

(52) U.S. Cl.
CPC ......... *A61M 25/0147* (2013.01); *A61F 2/243* (2013.01); *A61F 2/2436* (2013.01);
(Continued)

(58) Field of Classification Search
CPC .... A61F 2/2433; A61F 2/2436; A61F 2/2439; A61F 2/2427; A61M 25/0147; A61M 25/0136
See application file for complete search history.

(56) References Cited

U.S. PATENT DOCUMENTS 3,755,823 A    9/1973    Hancock
4,485,816 A    12/1984    Krumme
(Continued)

FOREIGN PATENT DOCUMENTS

AU    2006308187 A1    5/2007
AU    2006310681 A1    5/2007
(Continued)

OTHER PUBLICATIONS

International Search Report for PCT/EP2013/057431 dated Jul. 26, 2013 (4 pages).
(Continued)

*Primary Examiner* — Tuan V Nguyen
(74) *Attorney, Agent, or Firm* — Bookoff McAndrews, PLLC

(57) ABSTRACT

The invention relates to an operating handle (10-1, 10-2) for manipulating a catheter tip (80-1, 80-2) of a catheter delivery system. The operating handle (10-1, 10-2) comprises a hand grip (11) designed to be held by a user, and a manipulating part (12) axially aligned with the hand grip (11). The
(Continued)

Figure 1:
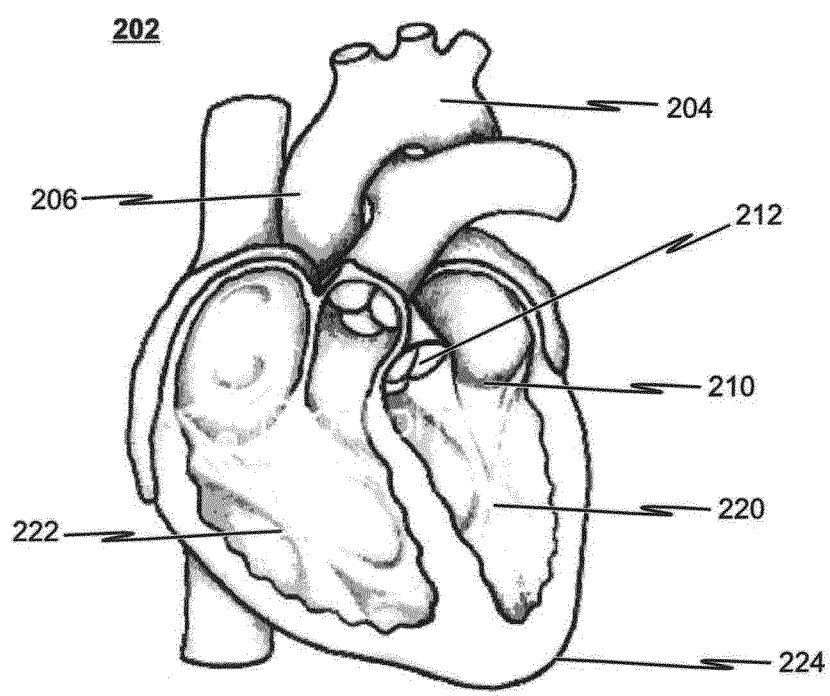

manipulating part (12) is rotatable relatively to the hand grip (11) about a longitudinal axis (L) defined by the operating handle (10-1, 10-2). The operating handle (10-1, 10-2) comprises at least one sliding member (30, 40) operatively linked with the manipulating part (12) by means of a cam mechanism (50) such that, upon rotation of the manipulating part (12) relative to the hand grip (11), the at least one sliding member (30, 40) moves axially in the direction of the longitudinal axis (L).

20 Claims, 21 Drawing Sheets

(52) U.S. Cl.
CPC ....... *A61M 25/0136* (2013.01); *A61F 2/2418* (2013.01); *A61F 2002/9517* (2013.01)

(56) References Cited

U.S. PATENT DOCUMENTS

| | | |
|---|---|---|
| 4,502,488 A | 3/1985 | Degironimo et al. |
| 4,922,905 A | 5/1990 | Strecker |
| 4,994,077 A | 2/1991 | Dobben |
| 5,002,566 A | 3/1991 | Carpentier et al. |
| 5,026,377 A | 6/1991 | Burton et al. |
| 5,035,706 A | 7/1991 | Giantureo et al. |
| 5,053,008 A | 10/1991 | Bajaj |
| 5,061,277 A | 10/1991 | Carpentier et al. |
| 5,094,661 A | 3/1992 | Levy et al. |
| 5,104,407 A | 4/1992 | Lam et al. |
| 5,163,953 A | 11/1992 | Vince |
| 5,197,979 A | 3/1993 | Quintero et al. |
| 5,211,183 A | 5/1993 | Wilson |
| 5,234,447 A | 8/1993 | Kaster et al. |
| 5,279,612 A | 1/1994 | Eberhardt |
| 5,332,402 A | 7/1994 | Teitelbaum |
| 5,336,258 A | 8/1994 | Quintero et al. |
| 5,350,399 A | 9/1994 | Erlebacher et al. |
| 5,352,240 A | 10/1994 | Ross |
| 5,368,608 A | 11/1994 | Levy et al. |
| 5,411,552 A | 5/1995 | Andersen et al. |
| 5,429,144 A | 7/1995 | Wilk |
| 5,456,713 A | 10/1995 | Chuter |
| 5,509,930 A | 4/1996 | Love |
| 5,540,712 A | 7/1996 | Kleshinski et al. |
| 5,549,666 A | 8/1996 | Hata et al. |
| 5,595,571 A | 1/1997 | Jaffe et al. |
| 5,609,626 A | 3/1997 | Quijano et al. |
| 5,613,982 A | 3/1997 | Goldstein |
| 5,632,778 A | 5/1997 | Goldstein |
| 5,643,278 A | 7/1997 | Wijay |
| 5,655,548 A | 8/1997 | Nelson et al. |
| 5,674,298 A | 10/1997 | Levy et al. |
| 5,679,112 A | 10/1997 | Levy et al. |
| 5,683,451 A | 11/1997 | Lenker et al. |
| 5,697,972 A | 12/1997 | Kim et al. |
| 5,713,953 A | 2/1998 | Vallana et al. |
| 5,733,325 A | 3/1998 | Robinson et al. |
| 5,746,775 A | 5/1998 | Levy et al. |
| 5,755,777 A | 5/1998 | Chuter |
| 5,817,113 A | 10/1998 | Gifford, III et al. |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,855,601 A | 1/1999 | Bessler et al. |
| 5,876,434 A | 3/1999 | Flomenblit et al. |
| 5,880,242 A | 3/1999 | Hu et al. |
| 5,885,238 A | 3/1999 | Stevens et al. |
| 5,891,160 A | 4/1999 | Williamson, IV et al. |
| 5,899,936 A | 5/1999 | Goldstein |
| 5,928,281 A | 7/1999 | Huynh et al. |
| 5,935,163 A | 8/1999 | Gabbay |
| 5,104,407 B1 | 9/1999 | Lam et al. |
| 5,957,949 A | 9/1999 | Leonhardt et al. |
| 5,987,344 A | 11/1999 | West |
| 6,001,126 A | 12/1999 | Nguyen-Thien-Nhon |
| 6,061,277 B1 | 2/2000 | Carpentier et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,168,614 B1 | 1/2001 | Andersen et al. |
| 6,177,514 B1 | 1/2001 | Pathak et al. |
| 6,183,481 B1 | 2/2001 | Lee et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,241,738 B1 | 6/2001 | Dereume |
| 6,254,564 B1 | 7/2001 | Wilk et al. |
| 6,254,636 B1 | 7/2001 | Peredo |
| 6,273,876 B1 | 8/2001 | Klima et al. |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,352,547 B1 | 3/2002 | Brown et al. |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,572,642 B2 | 6/2003 | Rinaldi et al. |
| 6,582,462 B1 | 6/2003 | Andersen et al. |
| 6,585,766 B1 | 7/2003 | Huynh et al. |
| 6,613,086 B1 | 9/2003 | Moe et al. |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,776,791 B1 | 8/2004 | Stallings et al. |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,584 B1 | 12/2004 | Seguin |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,101,396 B2 | 9/2006 | Artof et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,318,278 B2 | 1/2008 | Zhang et al. |

(56) References Cited

U.S. PATENT DOCUMENTS

| | | |
|---|---|---|
| 7,318,998 B2 | 1/2008 | Goldstein et al. |
| 7,322,932 B2 | 1/2008 | Xie et al. |
| 7,329,278 B2 | 2/2008 | Seguin et al. |
| 7,381,218 B2 | 6/2008 | Schreck |
| 7,393,360 B2 | 7/2008 | Spenser et al. |
| 7,399,315 B2 | 7/2008 | Lobbi |
| 7,452,371 B2 | 11/2008 | Pavcnik et al. |
| 7,473,275 B2 | 1/2009 | Marquez |
| 7,896,915 B2 | 3/2011 | Guyenot et al. |
| 7,914,575 B2 | 3/2011 | Guyenot et al. |
| 2001/0011187 A1 | 8/2001 | Pavcnik et al. |
| 2001/0021872 A1 | 9/2001 | Bailey et al. |
| 2001/0039450 A1 | 11/2001 | Pavcnik et al. |
| 2002/0010489 A1 | 1/2002 | Gayzel et al. |
| 2002/0032481 A1 | 3/2002 | Gabbay |
| 2002/0035390 A1 | 3/2002 | Schaldach et al. |
| 2002/0045846 A1 | 4/2002 | Kaplon et al. |
| 2002/0045929 A1 | 4/2002 | Diaz |
| 2002/0055775 A1 | 5/2002 | Carpentier et al. |
| 2002/0120322 A1 | 8/2002 | Thompson et al. |
| 2002/0120323 A1 | 8/2002 | Thompson et al. |
| 2002/0123790 A1 | 9/2002 | White et al. |
| 2002/0133226 A1 | 9/2002 | Marquez et al. |
| 2002/0143387 A1 | 10/2002 | Soetikno et al. |
| 2002/0151970 A1 | 10/2002 | Garrison et al. |
| 2002/0161426 A1 | 10/2002 | Iancea |
| 2002/0177840 A1 | 11/2002 | Farnholtz |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0153974 A1 | 8/2003 | Spenser et al. |
| 2003/0195620 A1 | 10/2003 | Huynh et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0093060 A1 | 5/2004 | Seguin et al. |
| 2004/0093063 A1 | 5/2004 | Wright et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0206363 A1 | 10/2004 | McCarthy et al. |
| 2004/0210301 A1 | 10/2004 | Obermiller et al. |
| 2004/0210304 A1 | 10/2004 | Seguin et al. |
| 2004/0210306 A1 | 10/2004 | Quijano et al. |
| 2004/0243143 A1 | 12/2004 | Corcoran et al. |
| 2004/0249343 A1 | 12/2004 | Cioanta |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0060018 A1 | 3/2005 | Dittman |
| 2005/0075725 A1 | 4/2005 | Rowe |
| 2005/0075776 A1 | 4/2005 | Cho |
| 2005/0096726 A1 | 5/2005 | Sequin et al. |
| 2005/0096736 A1 | 5/2005 | Osse et al. |
| 2005/0098547 A1 | 5/2005 | Cali et al. |
| 2005/0113902 A1 | 5/2005 | Geiser et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0137499 A1 | 6/2005 | Sheets et al. |
| 2005/0137609 A1 | 6/2005 | Guiraudon |
| 2005/0137682 A1 | 6/2005 | Justino |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0074484 A1 | 4/2006 | Huber |
| 2006/0111770 A1 | 5/2006 | Pavcnik et al. |
| 2006/0136034 A1 | 6/2006 | Modesitt et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0246584 A1 | 11/2006 | Covelli |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0056346 A1 | 3/2007 | Spencer et al. |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0203576 A1 | 8/2007 | Lee et al. |
| 2007/0213813 A1 | 9/2007 | Von Segesser et al. |
| 2007/0239271 A1 | 10/2007 | Nguyen |
| 2007/0244551 A1 | 10/2007 | Stobie |

(56) References Cited

U.S. PATENT DOCUMENTS

| | | |
|---|---|---|
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0022504 A1 | 1/2008 | Melsheimer |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0127707 A1 | 6/2008 | Kokish et al. |
| 2008/0133003 A1 | 6/2008 | Seguin et al. |
| 2008/0140189 A1 | 6/2008 | Nguyen et al. |
| 2008/0147182 A1 | 6/2008 | Righini et al. |
| 2008/0154355 A1 | 6/2008 | Benichou et al. |
| 2008/0200977 A1 | 8/2008 | Paul et al. |
| 2008/0215143 A1 | 9/2008 | Seguin |
| 2008/0221703 A1 | 9/2008 | Que et al. |
| 2008/0255660 A1 | 10/2008 | Guyenot et al. |
| 2008/0255661 A1 | 10/2008 | Straubinger et al. |
| 2008/0262602 A1 | 10/2008 | Wilk et al. |
| 2008/0269878 A1 | 10/2008 | Lobbi |
| 2008/0275549 A1 | 11/2008 | Rowe |
| 2009/0093876 A1 | 4/2009 | Nitzan et al. |
| 2009/0216312 A1 | 8/2009 | Straubinger et al. |
| 2009/0222076 A1 | 9/2009 | Figulla et al. |
| 2010/0100167 A1 | 4/2010 | Bortlein et al. |
| 2010/0160725 A1 | 6/2010 | Kiser et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0262231 A1 | 10/2010 | Tuval et al. |
| 2011/0093007 A1 | 4/2011 | Abbott et al. |
| 2011/0208290 A1 | 8/2011 | Straubinger et al. |
| 2011/0208297 A1 | 8/2011 | Tuval et al. |
| 2011/0319989 A1 | 12/2011 | Lane et al. |
| 2012/0041547 A1* | 2/2012 | Duffy .................... A61F 2/2436 623/2.11 |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| CN | 1745727 A | 3/2006 |
| CN | 2762776 Y | 3/2006 |
| CN | 1897892 A | 1/2007 |
| CN | 2933337 Y | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 10034105 C1 | 4/2002 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| DE | 20221871 U1 | 10/2008 |
| EP | 0084395 A1 | 7/1983 |
| EP | 0402036 B1 | 12/1990 |
| EP | 0402176 B1 | 12/1990 |
| EP | 0411118 A1 | 2/1991 |
| EP | 0458877 B1 | 4/1991 |
| EP | 0515324 A1 | 11/1992 |
| EP | 0547135 B1 | 6/1993 |
| EP | 0657147 A2 | 6/1995 |
| EP | 0 592 410 B1 | 10/1995 |
| EP | 0 592 410 B1 | 11/1995 |
| EP | 1 087 727 B1 | 11/1995 |
| EP | 0729364 B1 | 9/1996 |
| EP | 0756498 B1 | 5/1997 |
| EP | 0778775 B1 | 6/1997 |
| EP | 0826346 A1 | 3/1998 |
| EP | 0896813 A2 | 2/1999 |
| EP | 0903122 A2 | 3/1999 |
| EP | 0928615 A1 | 7/1999 |
| EP | 0938877 A2 | 9/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1499366 B1 | 1/2005 |
| EP | 1518518 A2 | 3/2005 |
| EP | 1 253 875 B1 | 4/2005 |
| EP | 1 251 803 B1 | 6/2005 |
| EP | 1469797 B1 | 11/2005 |
| EP | 1 690 515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| EP | 2474287 A1 | 7/2012 |
| FR | 2788217 A1 | 7/2000 |
| FR | 2815844 A1 | 5/2002 |
| FR | 2828263 A1 | 2/2003 |
| GB | 2433700 A | 7/2007 |
| GB | 2440809 A | 2/2008 |
| JP | 52-86296 | 7/1977 |
| JP | 62-227352 | 10/1987 |
| JP | 1049571 A | 2/1989 |
| JP | 7-504091 | 5/1995 |
| JP | 2001-526574 A | 12/2001 |
| JP | 2004-504111 A | 2/2002 |
| JP | 2002-525168 A | 8/2002 |
| JP | 2002-525169 A | 8/2002 |
| JP | 2002-536115 A | 10/2002 |
| JP | 2003-515386 A | 5/2003 |
| JP | 2003-523262 | 8/2003 |
| JP | 2003-524504 | 8/2003 |
| JP | 2004-283461 A | 10/2004 |
| JP | 2005-118585 | 5/2005 |
| JP | 2007-521125 A | 8/2007 |

(56) References Cited

FOREIGN PATENT DOCUMENTS

| | | |
|---|---|---|
| JP | 2007-296375 | 11/2007 |
| JP | 2008-539985 A | 11/2008 |
| JP | 2009-131397 A | 6/2009 |
| JP | 2009-534157 A | 9/2009 |
| JP | 2010-525896 | 7/2010 |
| JP | 2010-526609 A | 8/2010 |
| JP | 2012-500665 | 1/2012 |
| WO | WO 92/12690 | 8/1982 |
| WO | WO-90/09102 | 8/1990 |
| WO | WO 91/17720 A1 | 11/1991 |
| WO | WO 95/11055 A1 | 4/1995 |
| WO | WO-95/24873 | 9/1995 |
| WO | WO-95/28183 | 10/1995 |
| WO | WO 95/29713 A1 | 11/1995 |
| WO | WO-96/13227 | 5/1996 |
| WO | WO 97/27893 A1 | 8/1997 |
| WO | WO 97/27898 A1 | 8/1997 |
| WO | WO-97/32615 | 9/1997 |
| WO | WO 98/08456 A1 | 3/1998 |
| WO | WO 98/11846 A1 | 3/1998 |
| WO | WO 98/19633 A1 | 5/1998 |
| WO | WO-98/43556 | 10/1998 |
| WO | WO-98/46165 | 10/1998 |
| WO | WO 98/53761 A1 | 12/1998 |
| WO | WO 99/36001 A1 | 7/1999 |
| WO | WO-99/37337 | 7/1999 |
| WO | WO 99/42058 A1 | 8/1999 |
| WO | WO 99/53987 A1 | 10/1999 |
| WO | WO-99/66863 | 12/1999 |
| WO | WO 00/02503 A1 | 1/2000 |
| WO | WO 00/15148 | 3/2000 |
| WO | WO 00/18330 | 4/2000 |
| WO | WO 00/18333 A1 | 4/2000 |
| WO | WO-00/18445 | 4/2000 |
| WO | WO 00/21464 A1 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO 00/69367 A1 | 11/2000 |
| WO | WO 00/78226 A1 | 12/2000 |
| WO | WO-01/10209 A1 | 2/2001 |
| WO | WO 2001/35870 A1 | 5/2001 |
| WO | WO-01/41679 A1 | 6/2001 |
| WO | WO 2001/039700 A1 | 6/2001 |
| WO | WO 01/49213 A2 | 7/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 02/22054 A1 | 3/2002 |
| WO | WO 2002/36048 A1 | 5/2002 |
| WO | WO-02/058745 A1 | 8/2002 |
| WO | WO-02/100301 A1 | 12/2002 |
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO 03/051231 A2 | 6/2003 |
| WO | WO-03/079928 A2 | 10/2003 |
| WO | WO 03/079933 A1 | 10/2003 |
| WO | WO 03/092554 A1 | 11/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO 2004/030515 A2 | 4/2004 |
| WO | WO 2004/043301 A1 | 5/2004 |
| WO | WO 2004/064671 A2 | 8/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/011534 A1 | 2/2005 |
| WO | WO 2005/021063 A2 | 3/2005 |
| WO | WO 2005/034812 A1 | 4/2005 |
| WO | WO 2005/062980 A2 | 7/2005 |
| WO | WO 2005/063980 A1 | 7/2005 |
| WO | WO 2005/070343 A1 | 8/2005 |
| WO | WO-2005/072654 A1 | 8/2005 |
| WO | WO 2005/102015 A2 | 11/2005 |
| WO | WO 2006/066327 | 6/2006 |
| WO | WO-2006/066327 A1 | 6/2006 |
| WO | WO 2006/070372 A2 | 7/2006 |
| WO | WO 2006/076890 | 7/2006 |
| WO | WO 2006/089517 A1 | 8/2006 |
| WO | WO-2006/102063 A2 | 9/2006 |
| WO | WO 2006/108090 A2 | 10/2006 |
| WO | WO 2006/124649 A2 | 11/2006 |
| WO | WO-2006/124649 A2 | 11/2006 |
| WO | WO 2006/127756 A2 | 11/2006 |
| WO | WO 2006/127765 A1 | 11/2006 |
| WO | WO 2006/129441 A1 | 12/2006 |
| WO | WO-2006/132948 A1 | 12/2006 |
| WO | WO 2006/133959 A1 | 12/2006 |
| WO | WO 2007/047488 A2 | 4/2007 |
| WO | WO 2007/047945 A2 | 4/2007 |
| WO | WO 2007/048529 A1 | 5/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO 2007/123956 | 11/2007 |
| WO | WO-2008/028569 A1 | 3/2008 |
| WO | WO 2008/031103 A2 | 3/2008 |
| WO | WO 2008/035337 A2 | 3/2008 |
| WO | WO 2008/045949 | 4/2008 |
| WO | WO 2008/051554 A2 | 5/2008 |
| WO | WO 2008/070797 A2 | 6/2008 |
| WO | WO 2008/079962 A1 | 7/2008 |
| WO | WO 2008/098191 A2 | 8/2008 |
| WO | WO 2008/101083 A2 | 8/2008 |
| WO | WO 2008/125153 A1 | 10/2008 |
| WO | WO 2008/137603 A2 | 11/2008 |
| WO | WO 2008/138584 A1 | 11/2008 |
| WO | WO 2008/150529 A1 | 12/2008 |
| WO | WO 2009/053497 A1 | 4/2009 |
| WO | WO 2009/094188 A2 | 7/2009 |
| WO | WO 2009/106545 A1 | 9/2009 |
| WO | WO 2009/149462 A2 | 12/2009 |
| WO | WO 2010/022138 A2 | 2/2010 |
| WO | WO 2011/008812 A2 | 1/2011 |
| WO | WO 2011/060386 A2 | 5/2011 |
| WO | WO 2011/104269 A1 | 9/2011 |
| WO | WO 2011/120050 A1 | 9/2011 |
| WO | WO 2011/144351 A2 | 11/2011 |
| WO | WO 2011/147849 A1 | 12/2011 |
| WO | WO 2012/023980 A1 | 2/2012 |
| WO | WO 2012/036742 A2 | 3/2012 |
| WO | WO 2012/038550 A1 | 3/2012 |
| WO | WO 2012/039748 A2 | 3/2012 |
| WO | WO 2012/082952 A2 | 6/2012 |
| WO | WO 2012/106491 A1 | 8/2012 |
| WO | WO 2012/142189 A1 | 10/2012 |

OTHER PUBLICATIONS

Aortenklappenbioprothese erfolgreich in der Entwicklung, May 16, 2003 (1 page).

English translation of Aortenklappenbioprothese erfolgreich in der Entwicklung (2 pages). No Date.

(56) References Cited

OTHER PUBLICATIONS

Screen shots from http://www.fraunhofer.de/presse/filme/2006/index.jsp, 2006 (2 pages).
Liang, Ma, et al., "Double-crowned valved stents for off-pump mitral valve replacement," *Eur. J. Cardio-Thoracic Surgery*, vol. 28, pp. 194-195 (2005) (5 pages).
Huber, Christoph H., et al. "Direct Access Valve Replacement (DAVR)—are we entering a new era in cardiac sugery?" *Eur. J. Cardio-Thoracic Surgery*, vol. 29, pp. 380-385 (2006) (6 pages).
File history for German Patent DE 195 46 692 filed Dec. 14, 1995 and patented Jul. 11, 2002 (111 pages).
Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).
Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).
Ferrari, M.W. et al., "Transarterial Aortic Valve Replacement with a Self expanding Stent in Pigs," *Heart*, vol. 90, No. 11, pp. 1326-1331 (2004).
Ferrari, "Entwicklung eines Verfahrens zum transvaskulären Aortenklappenersatz," Habilitationsschrift, Medizinische Fakultät der Friedrich-Schiller-Universität Jena, pp. 49-52, dated Sep. 2003.
Ferrari, "Entwicklung eines Verfahrens zum transvaskulären Aortenklappenersatz," Habilitationsschrift, Medizinische Fakultät der Friedrich-Schiller-Universität Jena, pp. 1-159, dated Sep. 2003.
German National Library, bibliographic information for Ferrari, M., "Entwioklung eines Verfahrens zum transvaskulären Aortenklappenersatz," available at https://www.deutsche-digitale-bibliothek.de/item/U2RQV45RMES4YP6AHEPGN4QPJWAMGROI. No Date.

\* cited by examiner

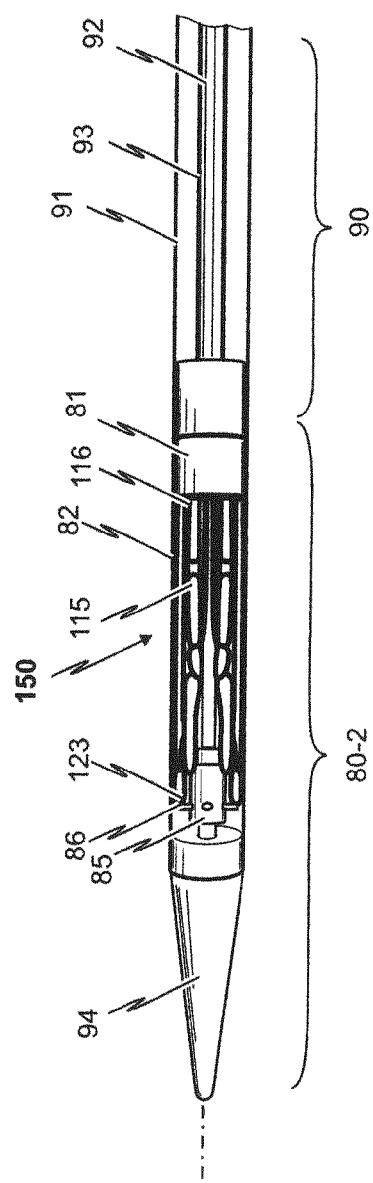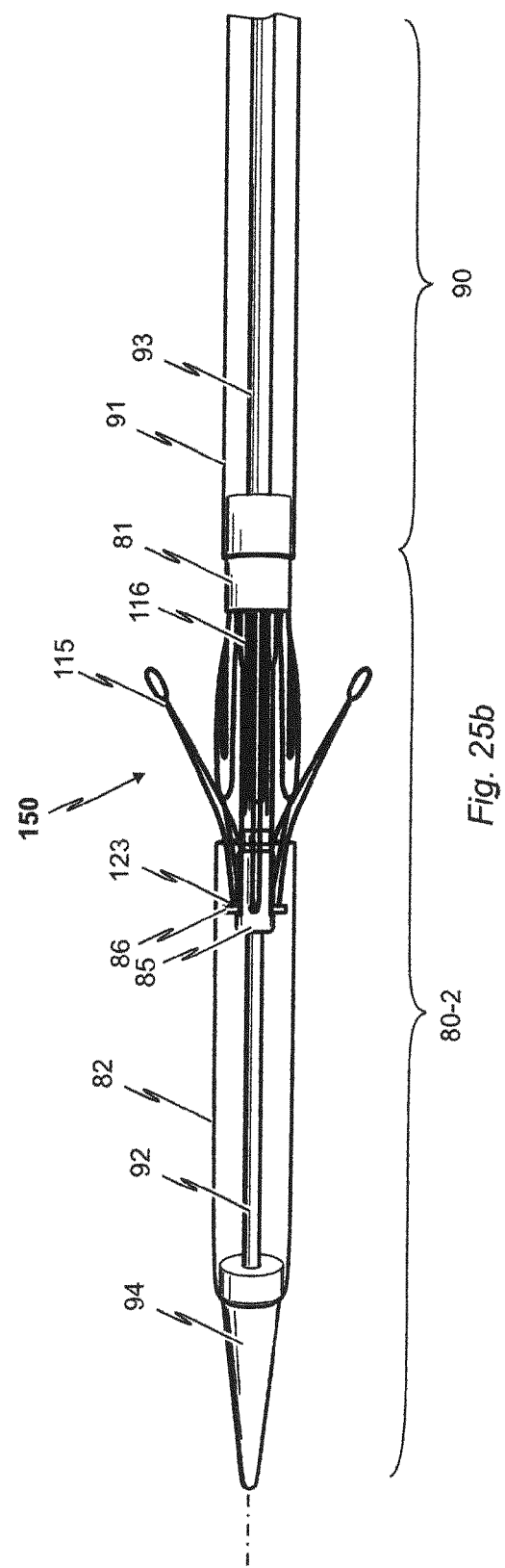

CATHETER DELIVERY SYSTEM FOR HEART VALVE PROSTHESIS

This application is a national stage filing under 35 U.S.C. § 371 of International Application No. PCT/EP2013/057431, filed on Apr. 10, 2013, incorporated by reference herein in its entirety, which published in the English language and claims the benefit of priority to European Application No. 12168367.6 filed, on May 16, 2012.

The present disclosure relates generally to surgical procedures, and more specifically to devices and methods for minimally-invasive surgery, such as minimally invasive cardiac surgery. In more detail, some embodiments of the disclosure relate to technologies pertinent to heart valve defect treatment, such as treatment of a heart valve failure or a heart valve stenosis in a patient.

The present disclosure further concerns an operating handle for manipulating a catheter tip of a catheter delivery system as well as a catheter delivery system for introducing an expandable heart valve prosthesis into the body of a patient. In addition, the present disclosure concerns a medical device for the treatment of a heart valve defect.

Heart valve surgery is used to repair or replace diseased heart valves. Medical technology has long since endeavored to correct valvular defects such as, for example, aortic valve insufficiencies or aortic valve stenosis, without requiring open heart surgery with minimally invasive methods. During the last decades minimally invasive forms of treatment have been developed and approved. They are in particular characterized in that a catheter delivery system is employed in order to advance to the side inside the body for implantation of a prosthetic device. Since by employing a catheter delivery system only small incisions are necessary resulting in a faster patient recovery with less pain and bodily trauma can be achieved. Furthermore, in particular, in the case of performing a minimal invasive heart surgery the patient should not be placed on cardiopulmonary bypass for the duration of the surgery allowing the procedure to be performed under local anesthesia. This, in turn, may reduce the medical costs and the overall disruption of the life of a patient.

The term "catheter delivery system" as used herein generally refers to a medical system with which, for example, a stent system can be advanced in a minimally invasive fashion to the side of implantation in the patient's heart, for example to treat an aortic valve stenosis and/or aortic valve insufficiency. A catheter system thereby allows access by surgical instruments. The process of inserting a catheter system is catheterization. In most uses a catheter system is a thin, flexible tube: a "soft" catheter system; in some uses, it is a larger, solid tube: a "hard" catheter system.

In the present context, "minimally invasive" implantation procedures are procedures for treating a patient where, for example, a heart-lung machine is not needed when performing the procedure on the anaesthetized patient such that the medical procedure.

The expression "heart valve stenosis and/or aortic valve insufficiency" generally refers to, for example, a congenital or acquired dysfunction of one or more cardiac valves. Such valvular disorders can affect any of the four cardiac valves, whereby the valves in the left ventricle (aortic and mitral valve) are certainly more frequently affected than thus of the right ventricle (pulmonary and tricuspid valve). The functional disorder can result in narrowing (stenosis) or inability to close (insufficiency) or a combination of the two (combined cardiac defect).

A medical catheter delivery system may comprise a catheter system by which a stent, as needed with a prosthetic heart valve affixed thereto, can be introduced into the patient's body in its folded state. The medical catheter delivery system can, for example, exhibit a catheter tip having at least one manipulatable receiving area at a distal end region of the catheter system, i.e. closest to the heart.

It is moreover conceivable for the medical catheter delivery system to exhibit a operating handle at the proximal end region of the catheter system, i.e. at the end region of the catheter system furthest from the heart and the catheter tip, with which the at least one receiving area of the catheter tip can be appropriately manipulated such that an expandable stent or prosthesis accommodated in the catheter tip can be incrementally released from the catheter tip according to a predefined or predefinable sequence of events.

Generally, there are two minimally invasive approaches known for implanting a prosthetic heart valve. The first approach is the so-called transarterial or transfemoral approach in which a medical instrument, for example, a catheter tip with an expandable heart valve prosthesis housed therein, is advanced to the implantation side via the aorta of a patient. A transarterial or transfemoral retrograde valve delivery procedure for valve replacement is typically limited by the sides of the catheter delivery system and is generally not recommended for patients with an existing peripheral vascular disease.

The second approach is the so-called transapical or transventrical approach, wherein access to the heart is provided through the apical area of the heart or through a ventricle of the heart in order to introduce, for example, an expandable stent system or an expandable heart valve prosthesis. Generally, the apical area or apex of the heart corresponds to the blunt rounded inferior extremity of the heart formed by the left and right ventricles. A transapical or transventrical retrograde delivery procedure is the most direct, shortest, antegrade and controllable access for transcatheter aortic valve replacement (TAVR).

Transapical or transventrical transcatheter valve implantation techniques typically involve an incision, for example, a thoracotomy, in order to gain access to the heart. After reaching the implantation side with the transapical or transventrical approach, an expandable heart valve prosthesis, for example, a stent with a prosthetic heart valve affixed thereto, can then be positioned and unfolded. After unfolding, the heart valve prosthesis can be anchored in the desired position in the heart, for example, with the aid of anchoring hubs.

A heart valve prosthesis of this type may include, for example, of a self-expanding or balloon-expanding anchoring support (also termed "heart valve stent" or "stent" in the following), to which the actual prosthetic heart valve is fastened, preferably in the inflow area of the stent.

The implantation procedure of conventional heart valve prostheses is relatively complicated, difficult and expensive. Apart from the complicated implantation of heart valve prostheses as a replacement for an insufficient native heart valve, there is a fundamental risk of incorrect positioning of the stent or heart valve prosthesis with the catheter delivery systems used up to the present, which cannot be corrected without more extensive operative intervention.

A problem addressed by the present disclosure is that medical technology does not currently offer any catheter delivery system in particular for transarterial or transfemoral implantation of a self- or balloon-expandable heart valve stent with a prosthetic heart valve attached to it in which, on the one hand, the catheter delivery system enables a minimally invasive implantation of the heart valve prosthesis in a predictable manner and, on the other hand, dispensing with the need to use a heart-lung machine during the operation of the patient. With such catheter delivery systems, an operative intervention may be cost-effective and, in particular, to reduce the physical and mental stress on the patient. In more detail, there is a lack of a medical device for implantation of heart valve prosthesis that can also be used for patients on whom, for example, due to their age, an operation cannot be carried out without the aid of a heart-lung machine.

Because of the increasing number of patients requiring treatment, there is also a growing need for an improved catheter delivery system with which a minimally invasive intervention can be made on a patient for treatment of a heart valve stenosis and/or heart valve insufficiency in a precisely predictable way, whereby the success of the operation is in particular no longer significantly dependent on the skill and experience of the heart surgeon or radiologist carrying out the treatment.

This situation also applies to operations in which heart valve prosthesis with stent systems are implanted with the aid of a so-called balloon catheter system.

It is also regarded as problematic that, when using conventional catheter delivery systems, incorrect positioning of the heart valve prosthesis or the associated heart valve stent can frequently only be avoided when the heart surgeon or radiologist is especially experienced. It is indeed known, for example, to insert a heart valve stent with a prosthetic heart valve attached thereto into the body of a patient as far as a heart via the aorta, whereby self-expansion or balloon-expansion of the heart valve stent is initiated by external manipulation when the implantation location is reached, which should lead to a secure anchorage and precise positioning of the heart valve prosthesis. Such heart valve stents, however, cannot usually be removed in a simple way, and their position cannot usually be corrected once the stent has expanded.

Accordingly, there is basically a risk with known catheter delivery systems that if, for example, a self-expansion or balloon-expansion of the stent with the attached prosthetic heart valve is initiated in a non-optimum position, due to a slip by the heart surgeon or radiologist carrying out the treatment or other technical circumstances such as stent foreshortening, this position can only be corrected appropriately by way of a major, in particular operative intervention, which is frequently carried out on the open heart.

A heart valve stent of a heart valve prosthesis is described, for example, in document WO 2004/019825 A1. With such a conventional heart valve stent, positioning arches are provided, which can be inserted into the pockets of the native heart valve of a patient so that the heart valve stent can be positioned with the positioning arches. Additional so-called commissural hubs can also be formed in the known heart valve stent which, together with the positioning arches, clamp parts of the native heart valve leaflets once the stent has unfolded so that the stent can be positioned and anchored as a result of this clamping action.

Although the positioning arches provided on the conventional heart valve stent enable improved positioning of the heart valve prosthesis to be implanted, there is nevertheless still a risk of incorrect implantation and of the heart valve prosthesis being incapable of functioning correctly or functioning but unsatisfactorily. For example, it may be found during the intervention that the heart valve prosthesis or the heart valve stent is not optimally dimensioned for the patient. In such cases, even if only the respective positioning arches of the stent are in their expanded state, removal (explanation) or repositioning of the heart valve stent with a heart valve prosthesis affixed thereto is no longer possible and there exists an increased mortality risk for the particular patient.

An objective of the disclosure is to provide a catheter delivery system which is relatively easy to use and which allows for a lower risk and optimized implantation of an expandable heart valve stent or heart valve prosthesis. One aspect lies in a simplified handling of the catheter delivery system during implantation of an expandable heart valve stent or heart valve prosthesis. Hence, there is a need for an optimized operating handle for manipulating a catheter tip of a catheter delivery system as well as a catheter delivery system for introducing an expandable heart valve prosthesis into the body of a patient and for positioning the heart valve prosthesis at a desired implantation side, wherein the operating handle and the catheter delivery system are designed to enable the implantation of the heart valve prosthesis in an optimum implantation location in a sequence of events defined before the intervention.

A further objective is to propose a medical device for treatment of a heart valve stenosis and/or heart valve insufficiency, comprising a catheter delivery system and an expandable heart valve stent mounted in the catheter tip of the catheter delivery system, wherein the medical device is designed to reduce a risk to the patient on implantation of the heart valve prosthesis.

According to the one aspect of the disclosure, the invention resides in an operating handle for manipulating a catheter tip of a catheter delivery system, wherein the operating handle comprises a cam mechanism and means that prescribe a pre-set sequence of steps such that each subsequent step is inhibited until the preceding step has been completed. Ideally the operating handle includes means that prescribe or enforce a pre-set sequence of steps for staged release of a heart valve stent or a heart valve prosthesis accommodated in the catheter tip of the catheter delivery system.

The term "pre-set" refers to steps that have been set of fixed in advance of operation of the catheter delivery system and, in particular the operating handle of the catheter delivery system. The steps of operation are pre-conditioned such that one step must be completed before the next step can be effected. A predetermined series of steps reduces the risk of incorrect positioning and requires less skill and expertise on the part of whomsoever performs the procedure. Thus, the sequence of events which can be determined beforehand relates to those events or steps of the operation which depend on and, for example, may be controlled by the operating handle of the catheter delivery system.

In this way, a catheter tip of the catheter delivery system may be manipulated especially reliably with the operating handle and a heart valve stent or a heart valve prosthesis accommodated in the catheter tip of the catheter delivery system may be introduced in a particularly simple but nevertheless reliable way into the body of a patient and optimally positioned at the implantation site in the heart.

While it will be appreciated that such a operating handle may be applied to any catheter delivery system for which, for example, delivery, accurate positioning and/or control of medical devices is required, for the purposes of the present invention, the operating handle is used in conjunction with a catheter delivery system for introducing a heart valve stent or a heart valve prosthesis into a patient's body and for positioning the stent or prosthesis at a desired implantation site.

In particular, the catheter delivery system comprises a catheter shaft and a catheter tip at a distal end region of the catheter shaft. The proximal end region of the catheter shaft is attached to the operating handle. According to some aspects disclosed herein, the catheter tip accommodates the heart valve stent or heart valve prosthesis to be introduced into the patient's body.

An aspect of some embodiments of the disclosure relates to an operating handle for manipulating a catheter tip of a catheter delivery system, wherein the operating handle comprises a hand grip designed to be held by a user, and further comprises a manipulating part axially aligned with the hand grip. The manipulating part of the operating handle is rotatable relative to the hand grip about a longitudinal axis defined by the operating handle. The operating handle further comprises at least one sliding member operatively linked with the manipulating part of the operating handle with a cam mechanism such that, upon rotation of the manipulating part relative to the hand grip, the at least one sliding member moves axially in the direction of the longitudinal axis.

Preferably, the cam mechanism is integrated into the operating handle and transforms a rotary motion of the manipulating part relative to the hand grip into a linear motion of the at least one sliding member relative to the hand grip.

More preferably, the cam mechanism of the operating handle is provided with means that transform a rotary motion of the manipulating part relative to the hand grip into a pre-set sequence of steps of linear (axial) motions of the at least one sliding member relative to the hand grip.

In preferred embodiments disclosed herein, the at least one sliding member is operatively connected with at least one manipulatable member of a catheter tip of a catheter delivery system relative such that, upon rotation of the manipulating part relative to the hand grip, the at least one manipulatable member of the catheter tip operatively connected with the at least one sliding member of the operating handle performs a sequence of steps of axial movements (strokes) determined beforehand.

More preferably, the at least one manipulatable member of the catheter tip is manipulated in accordance with a displacement diagram characterizing the cam mechanism of the operating handle. The displacement diagram of the cam mechanism reflects the changing position the at least one sliding member (and the at least one manipulatable member of the catheter tip operatively connected with the at least one sliding member) would make as the manipulating part of the operating handle rotates relatively to the hand grip about a longitudinal axis defined by the operating handle. This diagram may relate angular position to the radial displacement experienced at that.

By determining the displacement diagram of the cam mechanism beforehand, the catheter tip of the catheter delivery system may be manipulated especially reliably with the operating handle and a heart valve stent or a heart valve prosthesis accommodated in the catheter tip of the catheter delivery system may be introduced in a particularly simple but nevertheless reliable way into the body of a patient and optimally positioned at the implantation site in the heart.

An aspect of some embodiments of the disclosure relates to a medical catheter delivery system for introducing an expandable heart valve prosthesis into the body of a patient. The medical catheter delivery system is preferably formed as a catheter system comprising a catheter tip at a distal end thereof, an operating handle at a proximal end thereof, and a catheter shaft interconnecting the catheter tip and the operating handle. The catheter tip of the medical catheter delivery system comprises at least one sleeve-shaped member at a distal end portion of the catheter delivery system, wherein the at least one sleeve-shaped member is capable of receiving at least partly a tightly compressed heart valve prosthesis thereby forming a part of the catheter tip.

For manipulating the at least one sleeve-shaped member, the operating handle of the medical catheter delivery system is further provided with at least one sliding member at a proximal end portion of the medical catheter delivery system, wherein the at least one sliding member is operatively connected with the at least one sleeve-shaped member. The operating handle of the medical catheter delivery system, which is disposed at the proximal end portion of the medical catheter delivery system, comprises a hand grip designed to be held by a user, and a manipulating part which is preferably axially aligned with the hand grip. The manipulating part is rotatable relative to the hand grip of the operating handle about a longitudinal axis defined by the operating handle. The at least one sliding member, which is operatively connected with the at least one sleeve-shaped member, is operatively linked with the manipulating part of the operating handle by way of a cam mechanism such that, upon rotation of the manipulating part of the operating handle relative to the hand grip of the operating handle, the at least one sliding member together with the at least one sleeve-shaped member operatively connected with the at least one sliding member moves axially in the direction of the longitudinal axis.

Preferably, the cam mechanism is integrated into the operating handle of the medical catheter delivery system. More preferably, the cam mechanism transforms a rotary motion of the manipulating part of the operating handle relative to the hand grip into a linear motion of the at least one sliding member and the at least one sleeve-shaped member operatively connected with the at least one sliding member.

According to some aspects of the present disclosure, the manipulating part of the operating handle is a rotating wheel designed to be gripped by a user with one of its hands, whereas the other hand of the user holds the hand grip of the operating handle. In this regard, the cam mechanism of the medical catheter delivery system preferably comprises a cylindrical member connected with the manipulating part of the operating handle, wherein the cylindrical member comprises at least one cam groove.

Moreover, the cam mechanism may further comprise at least one pin member having a first end portion connected with the at least one sliding member, and a second end portion opposite to the first end portion. The second end portion of the at least one pin member preferably engages with the at least one cam groove of the cylindrical member of the cam mechanism such that, upon rotation of the manipulating part of the operating handle relative to the hand grip, the at least one pin member follows a cam profile defined by the at least one cam groove of the cylindrical member of the cam mechanism.

In order to secure functional reliability of the cam mechanism, the cam mechanism is provided with means for preventing a rotational movement of the at least one sliding member relative to the operating handle. In some embodiments of the present disclosure, the means for preventing a rotational movement of the at least one sliding member relative to the operating handle comprises at least one elongated hole allocated to the at least one sliding member. The at least one elongated hole extends parallel to the longitudinal axis defined by the operating handle. Through the at least one elongated hole the at least one pin member connected with the at least one sliding member extends.

In embodiments of the disclosure, the manipulating part of the operating handle is a rotating wheel having a diameter greater than the diameter of the cylindrical member of the cam mechanism.

In accordance with embodiments, the hand grip of the operating handle is formed as a kind of jacket. The cylindrical member of the cam mechanism is at least partly disposed concentrically and coaxially with the hand grip, wherein the cylindrical member of the cam mechanism is rotatable relatively to the hand grip.

In embodiments of the present disclosure, the cylindrical member of the cam mechanism is a hollow cylindrical member. The cam mechanism preferably further comprises a body member disposed concentrically and coaxially with the hollow cylindrical member. The body member may comprise a cylindrical portion having a diameter less than an inner diameter of the hollow cylindrical member, the cylindrical portion of the body member being at least partly received in the interior of the hollow cylindrical member such that the hollow cylindrical member is rotatable relatively to the body member.

In some embodiments disclosed herein, the body member of the cam mechanism may be provided with at least one flange for preventing axial movement of the manipulating part of the operating handle relative to the body member.

According to embodiments of the operating handle of the medical catheter delivery system, the body member of the cam mechanism is at least partly hollow, wherein the at least one sliding member is received within the body member such that the at least one sliding member together with the at least one sleeve-shaped member operatively connected with the at least one sliding member is axially movable relatively to the body member.

In some embodiments of the present disclosure, the operating handle comprises a cam mechanism for transforming a rotary motion of the manipulating part of the operating handle into a linear motion of the at least one sliding member and the at least sleeve-shaped member operatively connected with the at least one sliding member, wherein the cam mechanism comprises a cylindrical member connected with the manipulating part of the operating handle, the cylindrical member comprising at least one cam groove. The cam mechanism may further comprise at least one pin member having a first end portion connected with the at least one sliding member, and a second end portion opposite to the first end portion. The second end portion of the at least one pin member engages with the at least one cam groove of the cylindrical member of the cam mechanism such that, upon rotation of the manipulating part of the operating handle relative to the hand grip, the at least one pin member follows a cam profile defined by the at least one cam groove.

Preferably, the cylindrical member of the cam mechanism is a hollow cylindrical member, wherein the cam mechanism further comprises a body member disposed concentrically and coaxially with the hollow cylindrical member. In some preferred embodiments, the body member is at least partly hollow, wherein the at least one sliding member is received within the body member such that the at least one sliding member together with the at least one sleeve-shaped member operatively connected with the at least one sliding member are axially movable relative to the body member of the cam mechanism.

In some embodiments of the present disclosure, the body member is preferably provided with at least one elongated hole which runs parallel to the longitudinal axis of the operating handle. The at least one pin member extends through the at least one elongated hole. The at least one elongated hole limits the freedom degree of the at least one pin member such that the at least one pin member cannot rotate relatively to the body member anymore.

In some embodiments, the body member is fixed to the hand grip of the operating handle. For this reason, the body member may comprise a portion fixed to the hand grip. For example, the portion of the body member, which is fixed to the hand grip, may be a cylindrical portion having a diameter equal to or substantially equal to the outer diameter of the hollow cylindrical member of the cam mechanism. Preferably, the hand grip of the operating handle is at least partly disposed around the cylindrical portion of the body member such as to be concentrically and coaxially with the cylindrical portion of the body member.

In embodiments of the present disclosure, the operating handle is provided with a locking mechanism for subdividing a maximal available turning movement of the manipulating part of the operating handle when the manipulating part is rotated relatively to the hand grip. The maximum available turning movement of the manipulating part is defined by the at least one cam groove of the cylindrical member of the cam mechanism and/or an elongated hole provided in the hollow body member of the cam mechanism. Preferably, the locking mechanism comprises at least one locking recess provided in the cylindrical member of the cam mechanism and at least one engaging piece operatively connected with the body member of the cam mechanism, wherein the at least one engaging piece is adapted to releasably engage with the at least one locking recess thereby preventing rotation or continued rotation of the cylindrical member of the cam mechanism relative to the body member.

In some embodiments, the locking mechanism can disengage the engaging piece when the engaging piece engages with the at least one locking recess. For example, the engaging piece may be spring loaded, including a spring loaded push-button operatively connected with the engaging piece, wherein the push-button is designed to be pushed by the user for disengaging the engaging piece.

More preferably, a lever may be connected with the push-button for pressing the engaging piece down when the push-button is pushed down by the user. In this regard, it is preferred that a driving piece having a first end region coupled to the lever by a pin such as to be pivotable in a plain perpendicular to the direction of pushing of the push-button, and further having a second end region for pressing the engaging piece down when the push-button is pushed down by the user.

In some embodiments of the locking mechanism, the driving piece is coupled to the lever such that the driving piece swings out relatively to the lever when the push-button is pushed down by the user and when simultaneously the cylindrical member of the cam mechanism is rotated relatively to the body member. The second end region of the driving piece then loses contact with the engaging piece when the driving piece swings out relatively to the lever arm. Some embodiments may further comprise centering bias for returning of the driving piece when the push-button is released.

A locking mechanism of the kind as disclosed herein ensures a step-wise manipulation of a catheter. In more detail, the locking mechanism prevents that the manipulating part of the operating handle can be rotated by the user relatively to the hand grip through a maximal available angular turning range, when the push-button is continuously pushed.

In accordance with embodiments of the locking mechanism, the locking mechanism comprises a plurality of locking recesses provided in the cylindrical member of the cam mechanism such as to subdivide the maximal available turning movement of the manipulating part of the operating handle into a plurality of consecutive indexing turning movements of the manipulating part. In this regard, it is conceivable when the locking mechanism comprises a first locking recess provided in the cylindrical member of the cam mechanism such that the at least one pin member of the cam mechanism is at the beginning of the at least one cam groove of the cylindrical member when the engaging piece of the locking mechanism engages with the first locking recess.

Moreover, it is conceivable when the locking mechanism comprises at least one second locking recess provided in the cylindrical member such that the at least one pin member of the cam mechanism is in a central portion of the at least one cam groove of the cylindrical member when the engaging piece of the locking mechanism engages with the at least one second locking recess. Also, it is conceivable when the locking mechanism comprises a third locking recess provided in the cylindrical member such that the at least one pin member of the cam mechanism is at the end of the at least one cam groove when the engaging piece of the locking mechanism engages with the third locking recess.

According to a further aspect of the present disclosure, the operating handle of the medical catheter delivery system further includes an operative linkage between the at least one sliding member and the manipulating part of the operating handle for selectively separating the sliding member and the manipulating part.

At least one pin member manipulating element may be operatively connected with the at least one pin member, the at least one pin member manipulating element being drivable from a first position, in which the at least one pin member engages the at least one cam groove of the cylindrical member of the cam mechanism, into a second position, in which the at least one pin member is disengaged from the at least one cam groove.

In an embodiment of the operating handle, the first end portion of the at least one pin member of the cam mechanism is at least partly received in a recess provided in the at least one sliding member such that the at least one pin member is movable relatively to the sliding member in a longitudinal direction defined by sliding this recess.

In accordance with an embodiment of the operating handle, the at least one pin member manipulating element comprises a lever arm having a first end region operatively connected with the at least one pin member of the cam mechanism, in particular with the first end portion of the at least one pin member. The lever arm of the at least one pin member manipulating element further have a second end region opposite to the first end region, wherein the second end region of the lever arm is operatively connected with an operating bar for moving the lever arm with the at least one sliding member connected thereon.

The at least one pin member is movable by the operating bar and the lever arm connected therewith from a coupled state, in which the second end portion of the at least one pin member engages the at least one cam groove of the cylindrical member of the cam mechanism, into an uncoupled state, in which the second end portion of the pin member disengages the cam groove and in which the pin member manipulating element at least partly engages with a further recess provided in the body member of the cam mechanism thereby blocking an axial movement of the sliding member relative to the body member upon rotation of the manipulating part of the operating handle relative to the hand grip.

In some embodiments of the medical catheter delivery system, the medical catheter delivery system further comprises at least one catheter tube having a distal end connected with the at least one sleeve-shaped member, and further having a proximal end connected with the at least one sliding member.

According to some embodiments, the medical catheter delivery system comprises a first sleeve-shaped member and a first sliding member operatively connected with a first sleeve-shaped member, and further comprises a second sleeve-shaped member and a second sliding member operatively connected with the second sleeve-shaped member. The first and second sliding members are both operatively linked with the manipulating part of the operating handle by the cam mechanism such that, upon rotation of the manipulating part of the operating handle relative to the hand grip, the first and second sliding members together with the first and second sleeve-shaped members operatively connected thereto move independently from each other axial in the direction of the longitudinal axis.

Preferably, the cam mechanism comprises a cylindrical member connected with the manipulating part, the cylindrical member comprising a first cam groove and a second cam groove.

The cam mechanism preferably further comprises a first pin member having a first end portion connected with the first sliding member, and a second end portion opposite to the first end portion, the second end portion of the first pin member engaging with the first cam groove such that, upon rotation of the manipulating part of the operating handle relative to the hand grip, the first pin member follows a cam profile defined by the first cam groove.

The cam mechanism preferably further comprises a second pin member having a first end portion connected with the second sliding member, and further having a second end portion opposite to the first end portion, the second end portion of the second pin member engaging with the second cam groove such that, upon rotation of the manipulating part relative to the hand grip, the second pin member follows a cam profile defined by the second cam groove.

Preferably, the first sleeve-shaped member and the second sleeve-shaped member provide a seat portion adapted to receive a heart valve prosthesis which is at least partly tightly compressed. More preferably, the medical catheter delivery system may further comprise a stent retaining system at the distal end portion of the catheter delivery system, the stent retaining system being capable of releasably fixing a heart valve prosthesis received in the seat portion. For releasing heart valve prosthesis received by the seat portion constituted by the first and second sleeve-shaped members, the first and second sleeve-shaped members are axially movable relatively to each other and relatively to the stent retaining mechanism to which the heart valve prosthesis is releasably fixed.

In particular, a medical catheter delivery system is disclosed, with which an expandable heart valve stent with a heart valve prosthesis attached thereto can be advanced to the implantation site in a particularly simple way, for example via the aorta of a patient being treated (transarterially or transfemorally). Preferably, during transarterial or transfemoral access by the medical catheter delivery system, the whole free cross-section available within the aorta is not completely filled up, since the catheter tip provided at the distal end region of the medical catheter delivery system, in which the heart valve prosthesis can be accommodated, can be made sufficiently small with respect to its external diameter.

The expandable heart valve stent with the prosthetic heart valve attached thereto can be accommodated temporarily during implantation in the folded-up state in the catheter tip of the catheter delivery system, which is provided at the distal end region of the medical catheter delivery system. The medical catheter delivery system may be of a length sufficient to allow the catheter tip provided at the distal end region of the catheter system to be guided through the aorta to the patient's heart by insertion at the patient's groin.

The medical catheter delivery system designed for transarterial or transfemoral access is therefore suitable for inserting a heart valve stent with a prosthetic heart valve attached to it, transarterially or transfemorally into the body of the patient; for example, the medical catheter delivery system is inserted with the catheter tip located at the distal end of the medical catheter delivery system via puncture of the A. femoris communis (inguinal artery).

In particular, with the medical catheter delivery system designed for transarterial or transfemoral access, the medical catheter delivery system may be designed so that it is both kink-resistant and flexible such that a bending radius of up to 4 cm, and preferably up to 3 cm, can be realised, at least at the distal end region of the medical catheter delivery system.

In order to treat a heart valve stenosis and/or heart valve insufficiency in a patient, a medical device is further disclosed.

The medical device comprises a medical catheter delivery system and an expandable heart valve stent together with a prosthetic heart valve affixed thereto. The expandable heart valve stent together with the prosthetic heart valve forms a heart valve prosthesis and is accommodated in the catheter tip of the medical catheter delivery system. While it is accommodated in the catheter tip of the medical catheter delivery system, the stent adopts a first previously definable configuration. Outside the catheter tip or in the implanted state, however, the stent exists in a second previously definable configuration. The first configuration of the stent corresponds to the folded-up state, while the stent exists in its expanded state in the second configuration.

A heart valve prosthesis is used with the medical catheter delivery system, as described for example in the European patent application No. 07 110 318 or in the European patent application No. 08 151 963, both of which are incorporated herein by reference in their entireties. In an embodiment of the medical device, a heart valve prosthesis comprising a heart valve stent is accordingly used which exhibits the following:
- a first retaining region, to which a heart valve prosthesis can be attached;
- an opposing, second retaining region with catheter retaining mechanism, for example in the form of retaining eyes or in the form of retaining heads, whereby at least one retaining mechanism of the stent can be put in releasable engagement with the stent holder (stent retaining mechanism) of the catheter tip forming part of the catheter delivery system;
- at least one retaining arch, to which a heart valve prosthesis can be fastened; and
- at least one and preferably three positioning arches, which are designed to engage in pockets of the native heart valve in the implanted state of the stent, thus to enable automatic positioning of the stent in the aorta of the patient.

The following will make reference to the drawings in providing a more precise detailing of preferred embodiments of the disclosure.

Figure 2A:
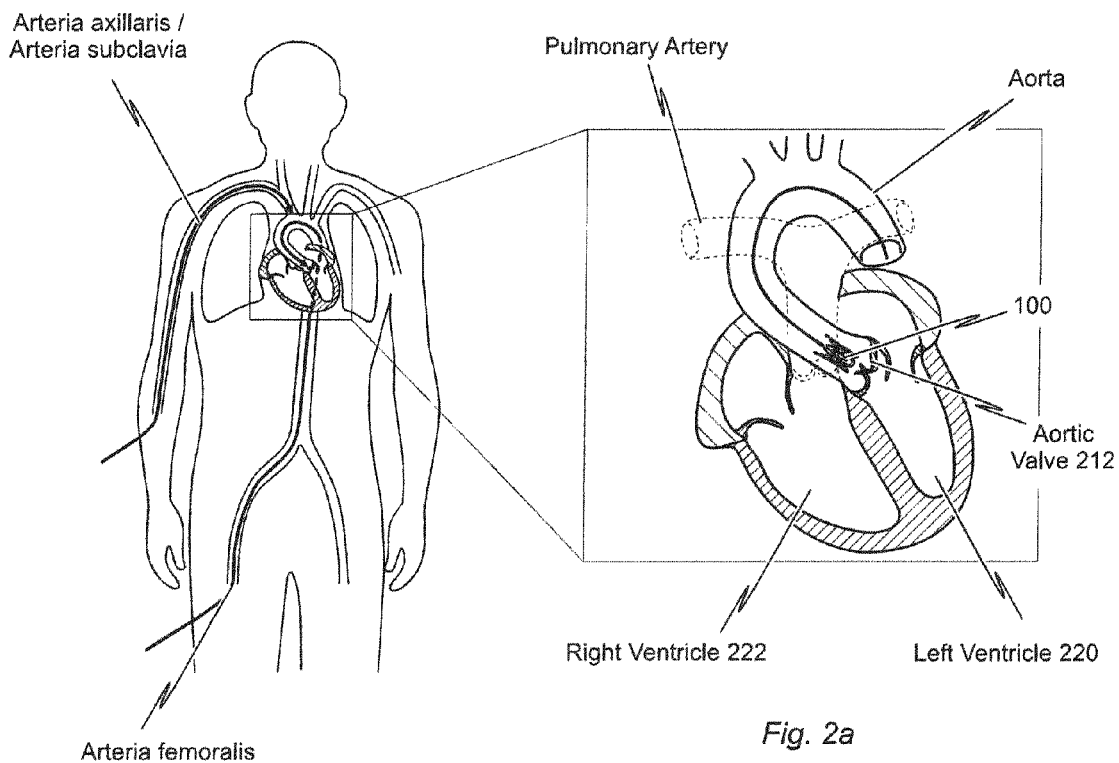
Figure 2B:
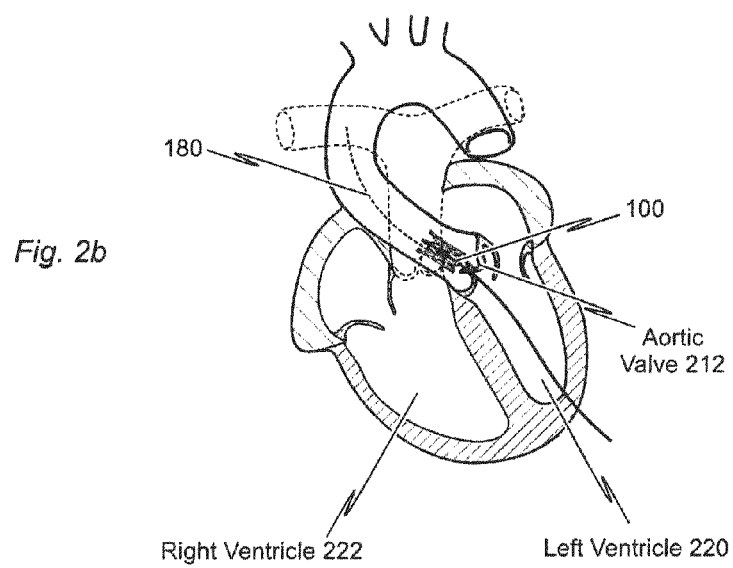
Figure 3:
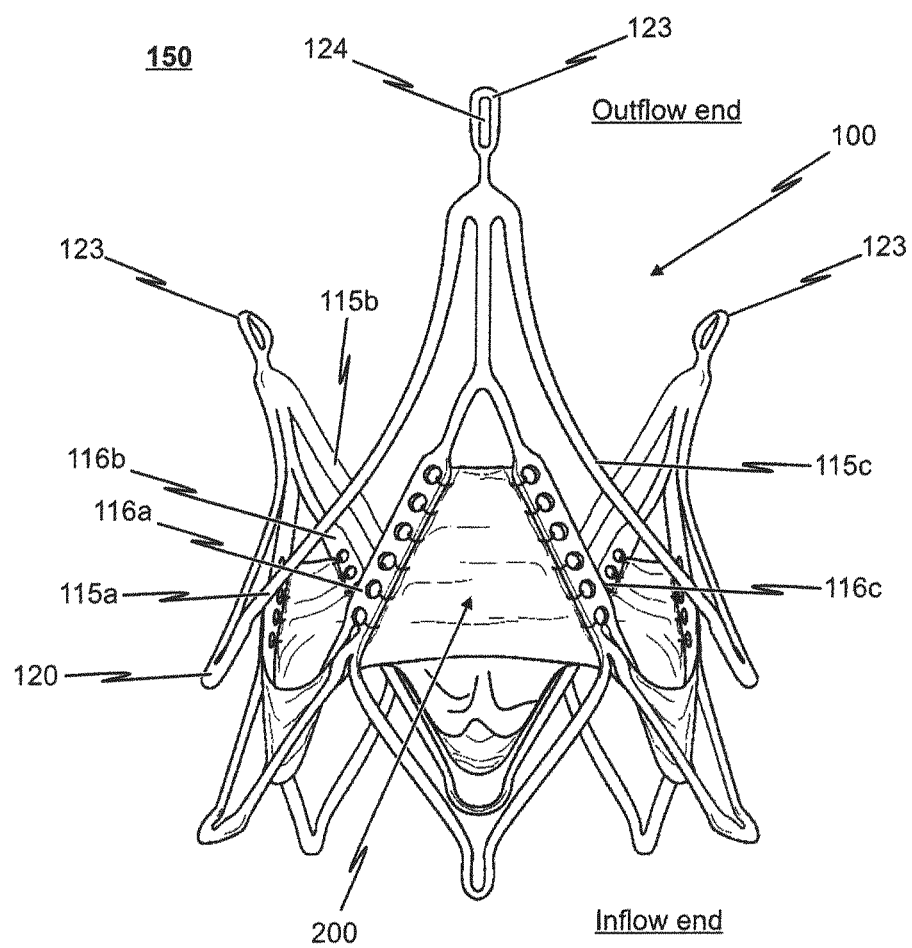
Figure 4:
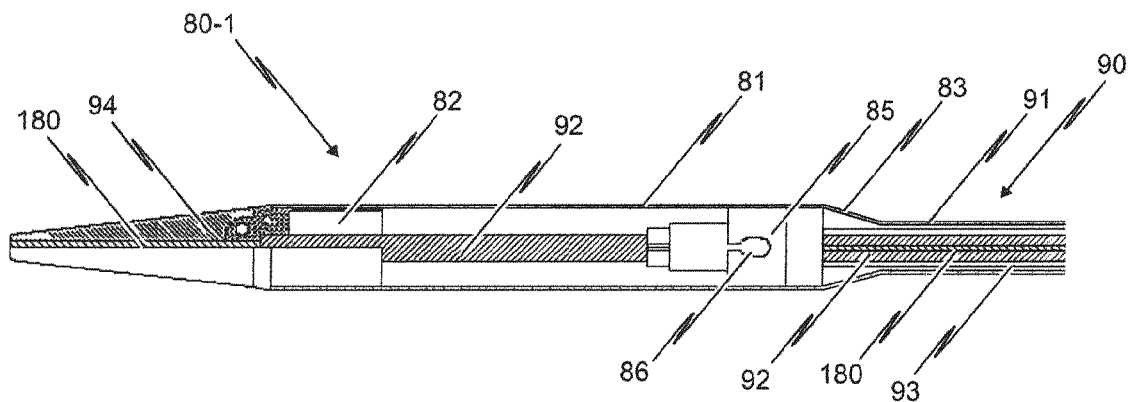
Figure 5:
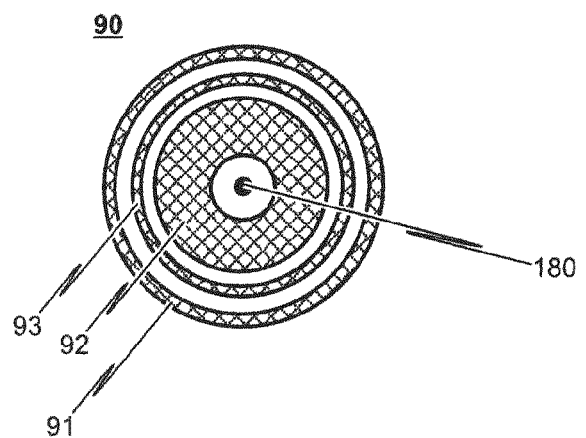
Figure 6A:
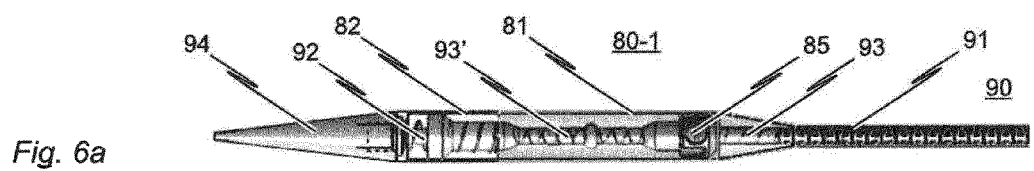
Figure 6B:
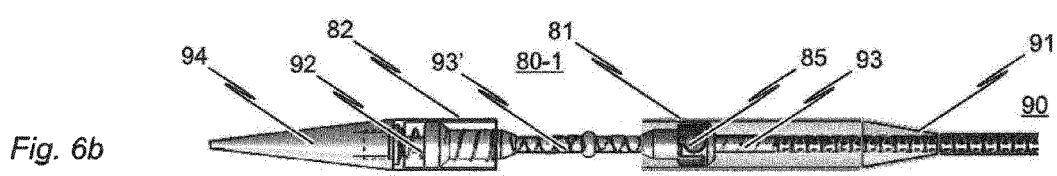
Figure 6C:
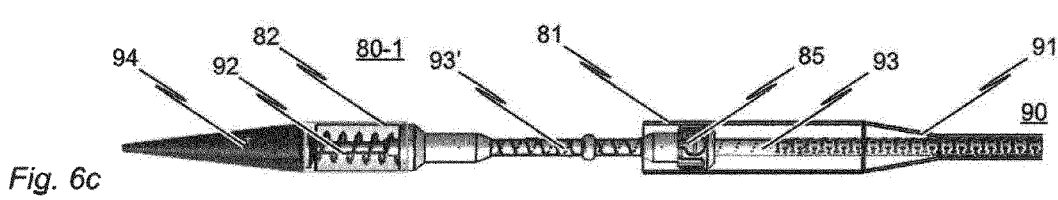
Figure 6D:
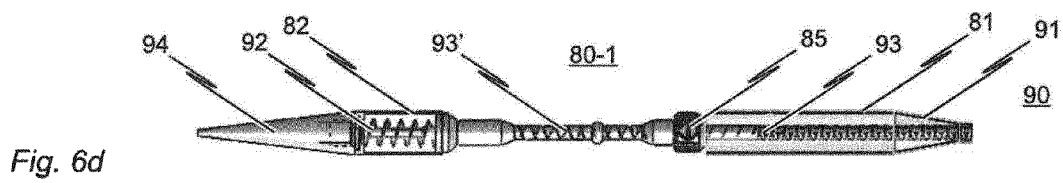
Figure 6E:
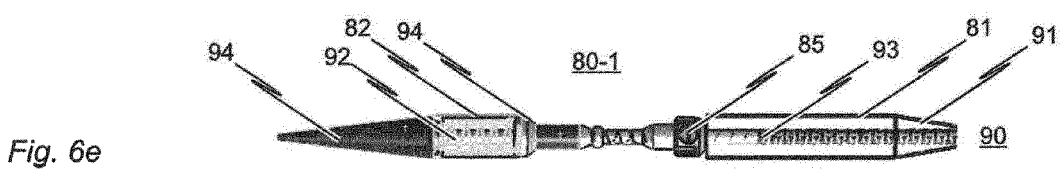
Figure 6F:
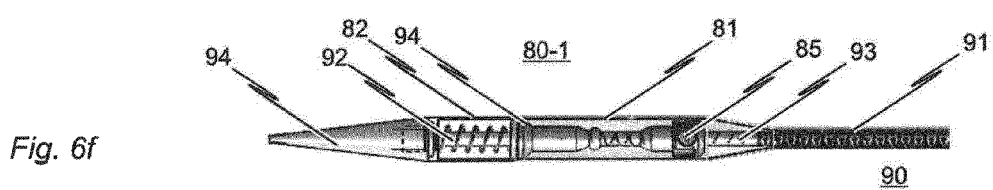
Figure 7C:
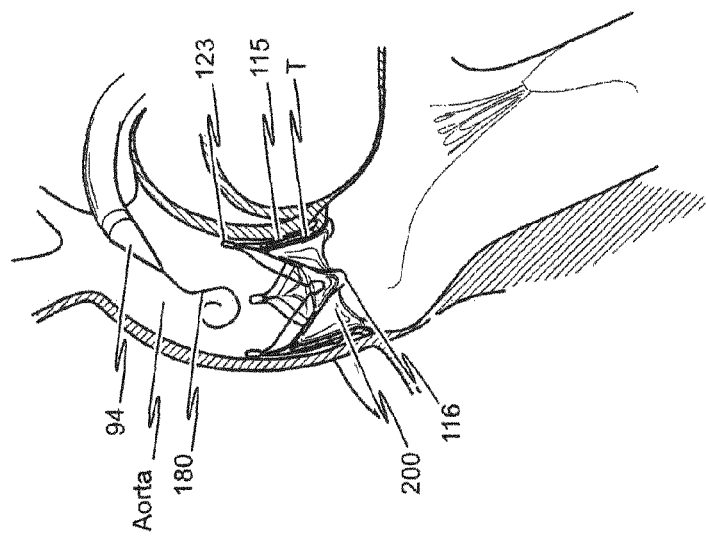
Figure 7B:
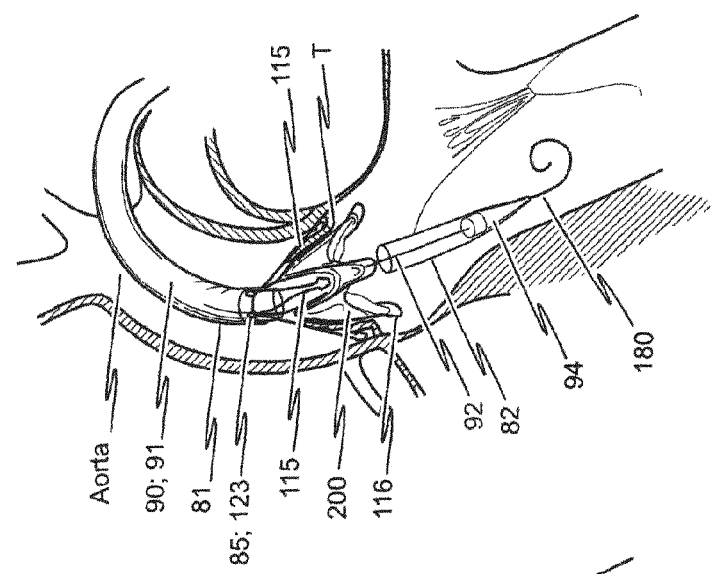
Figure 7A:
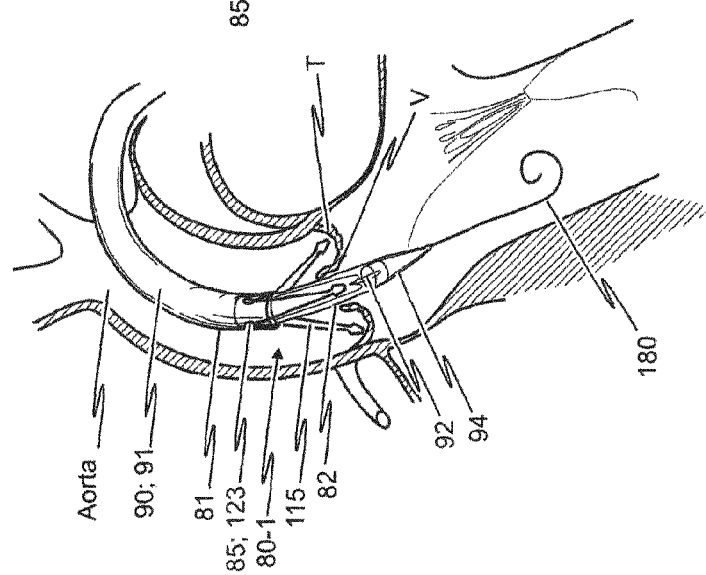
Figure 8:
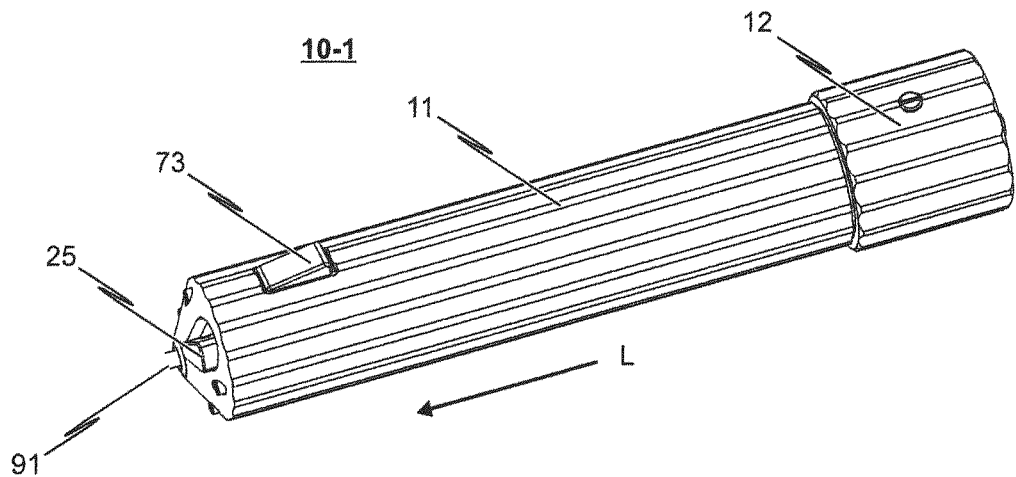
Figure 10:
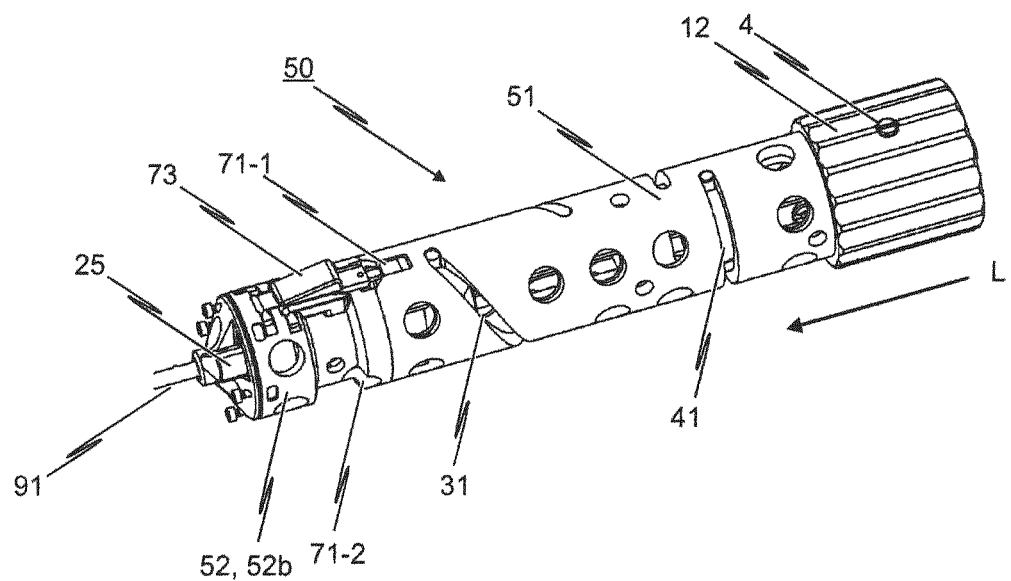
Figure 9A:
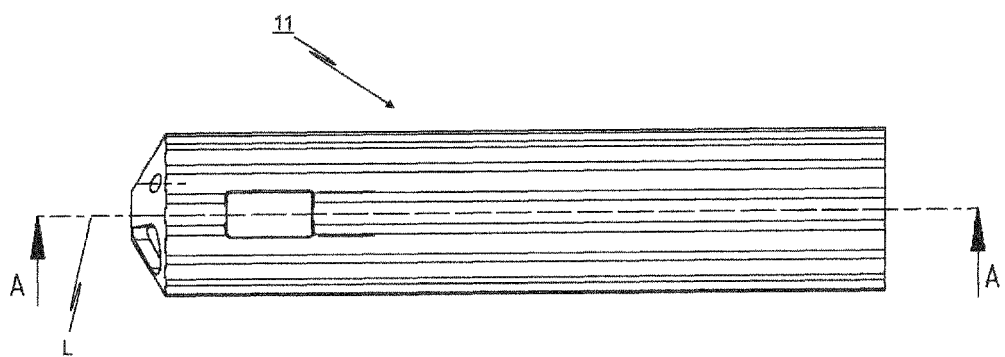
Figure 9B:
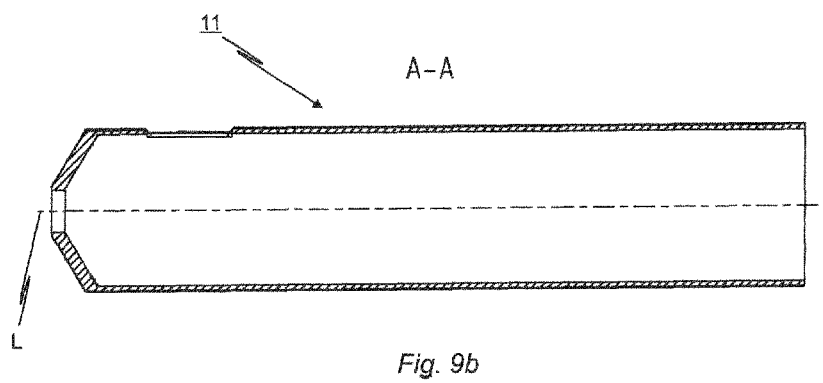
Figure 11:
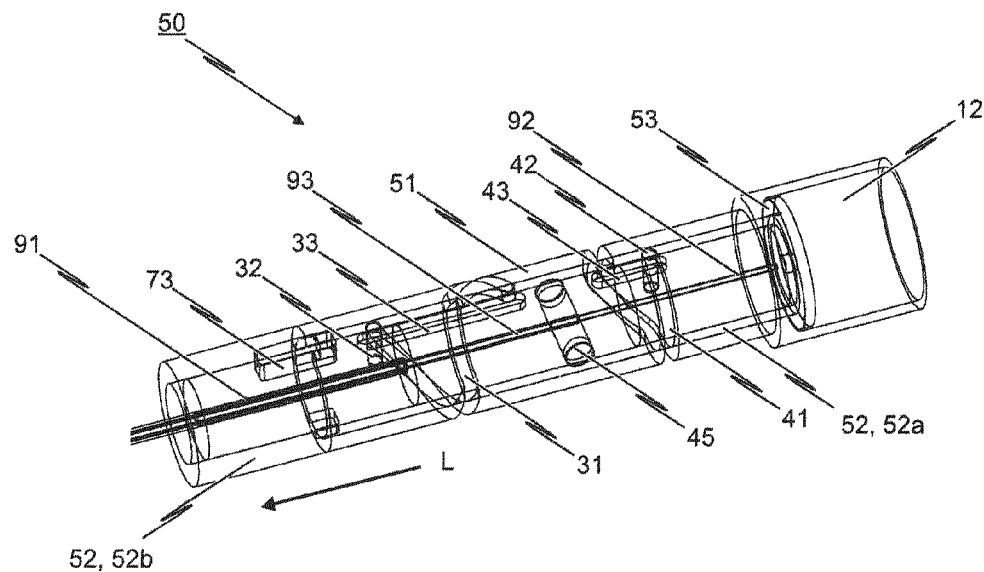
Figure 12:
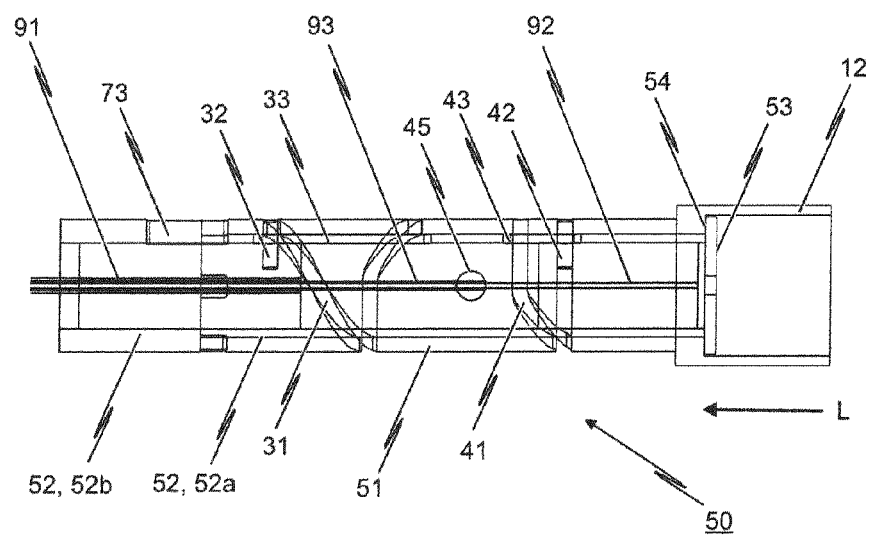
Figure 13:
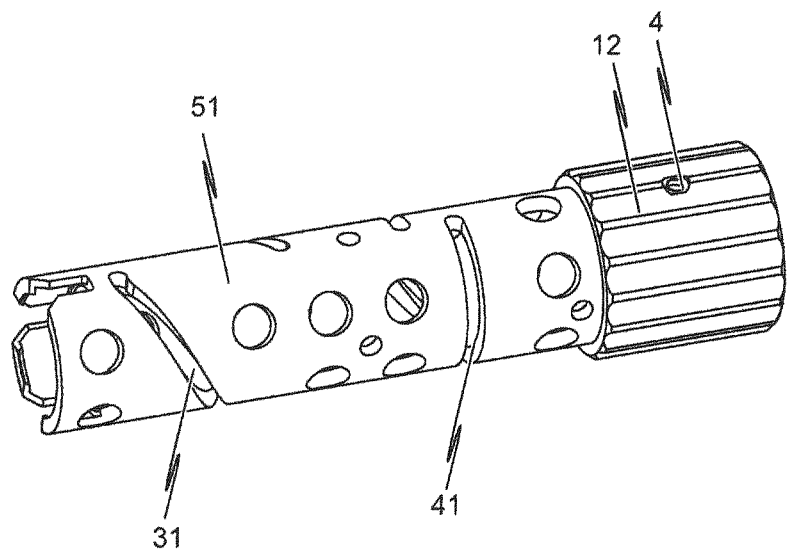
Figure 14:
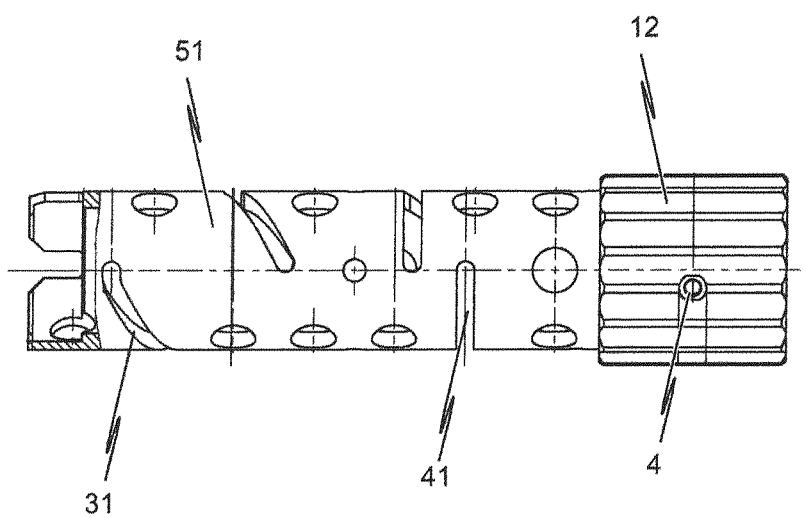
Figure 15:
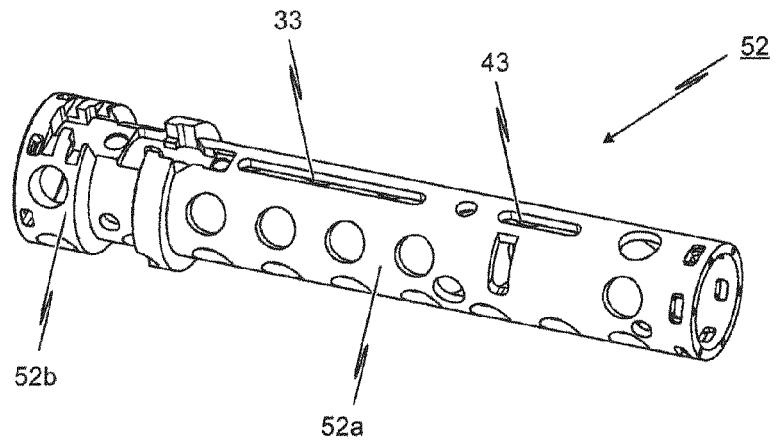
Figure 16:
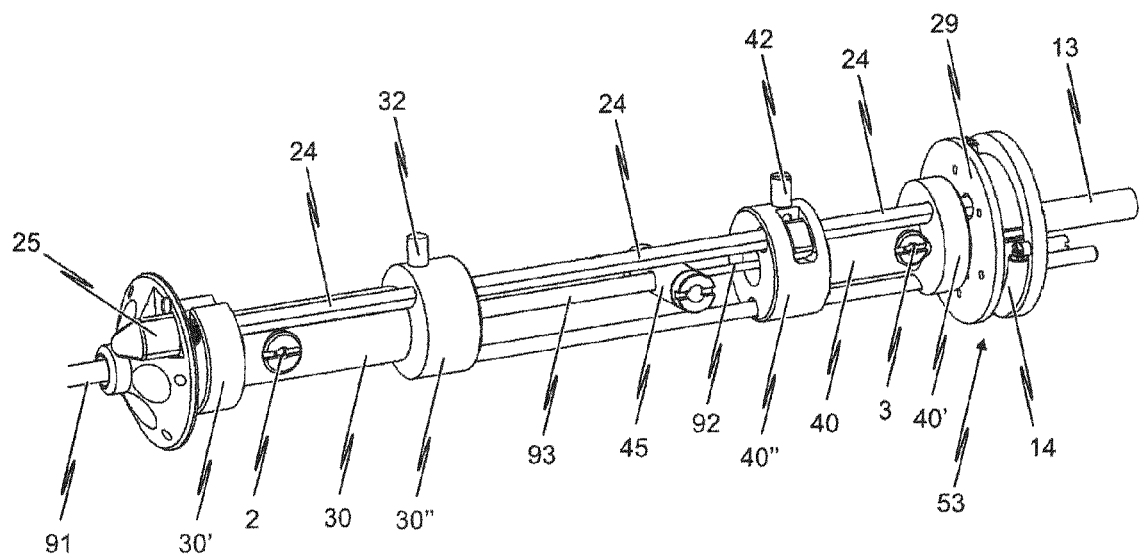
Figure 17A:
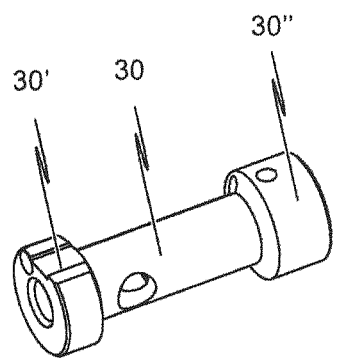
Figure 19:
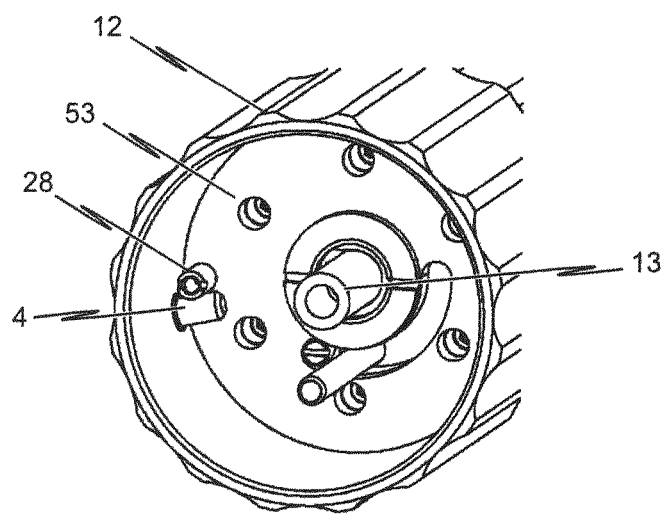
Figure 18A:
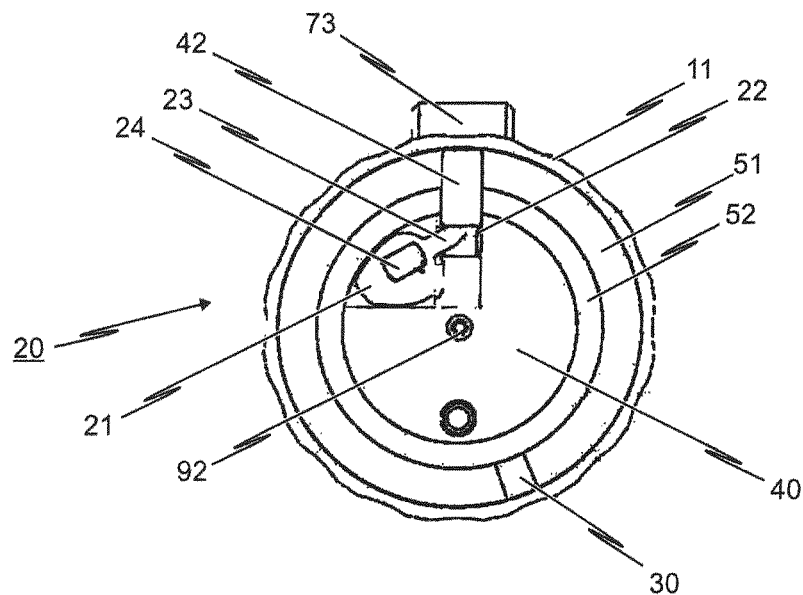
Figure 20A:
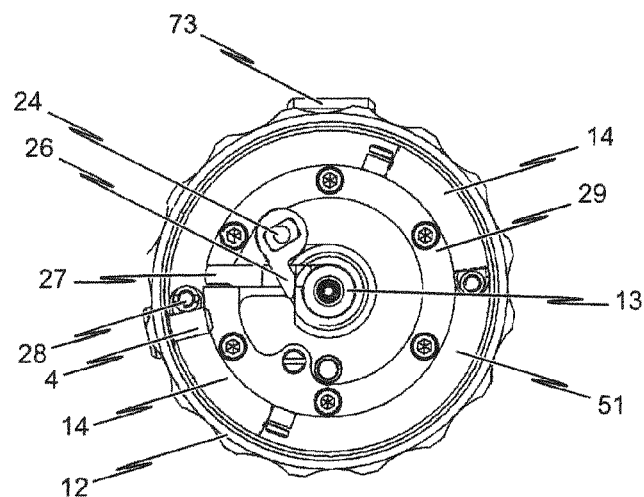
Figure 20B:
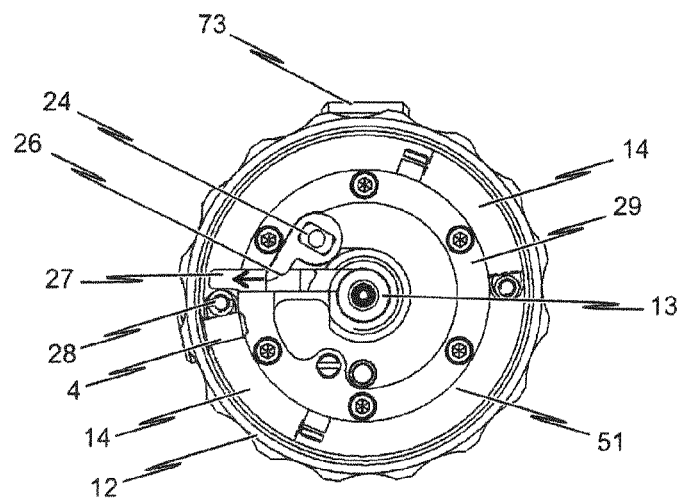
Figure 20C:
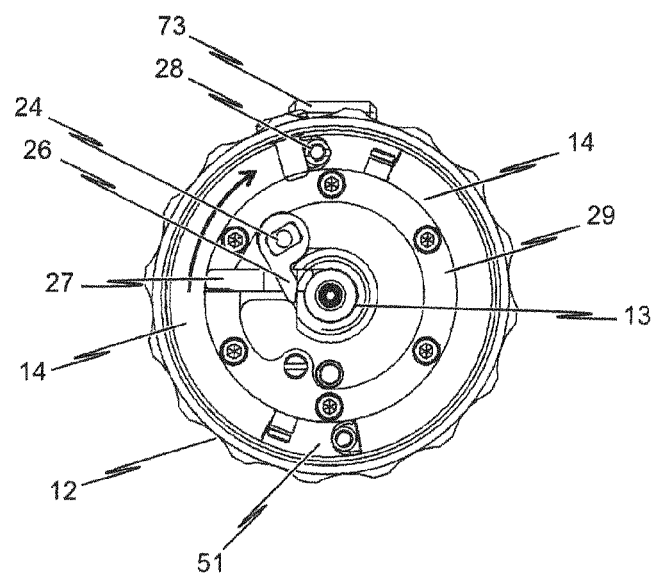
Figure 21:
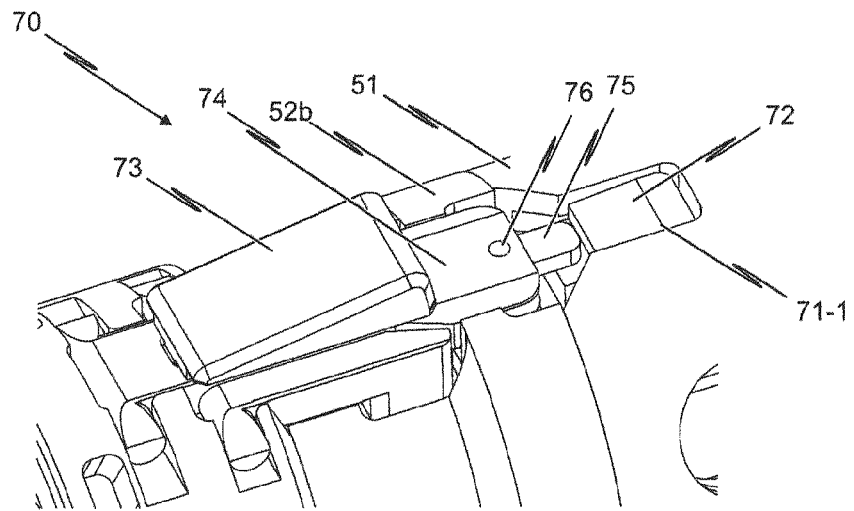
Figure 22:
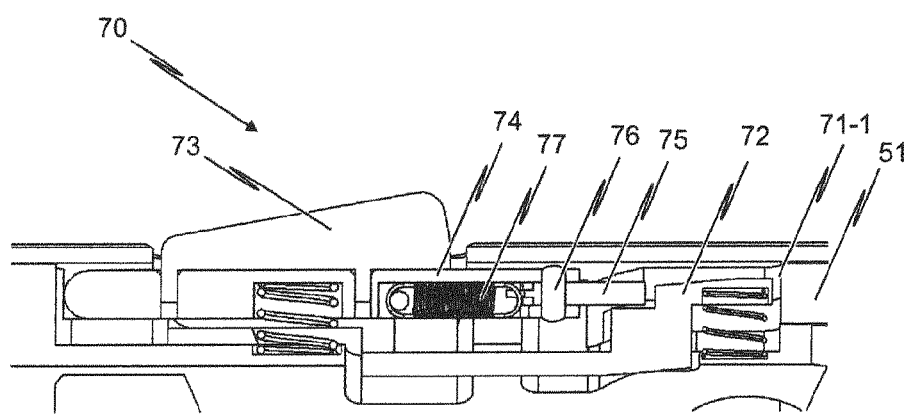
Figure 23A:
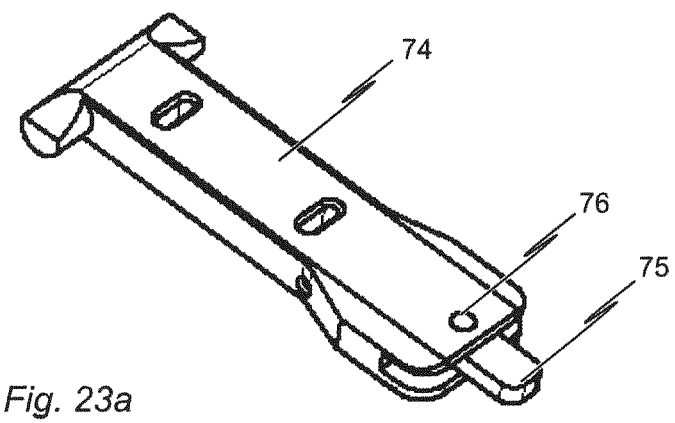
Figure 23B:
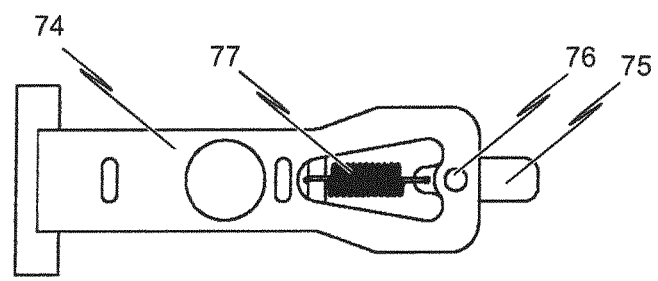
Figure 23C:
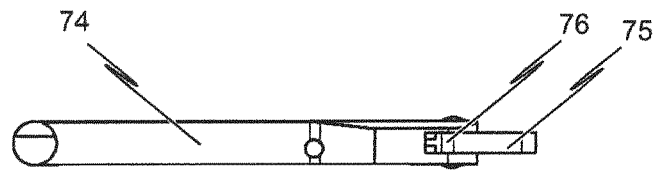
Figure 24:
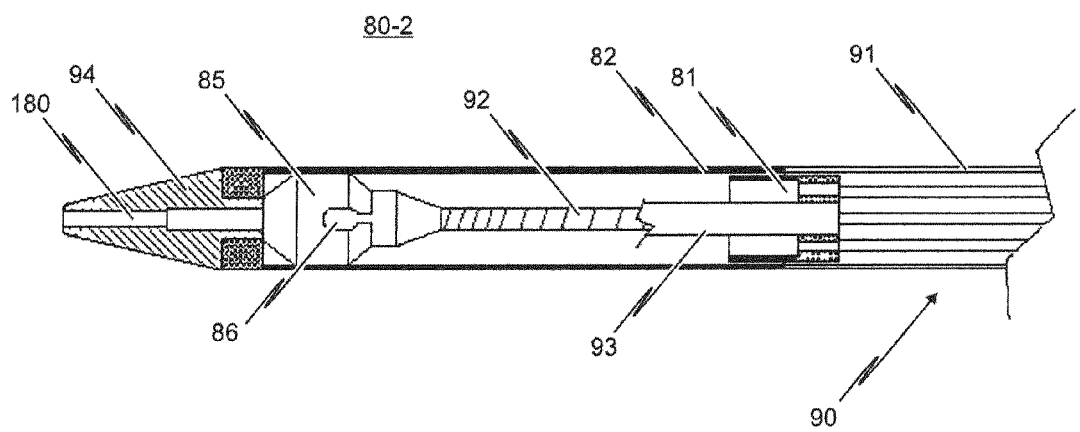
Figure 26:
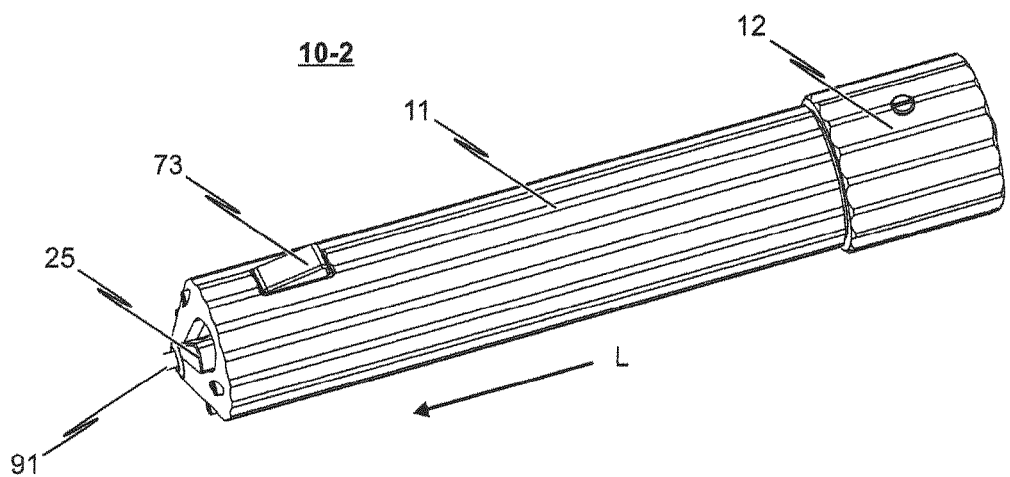
Figure 27:
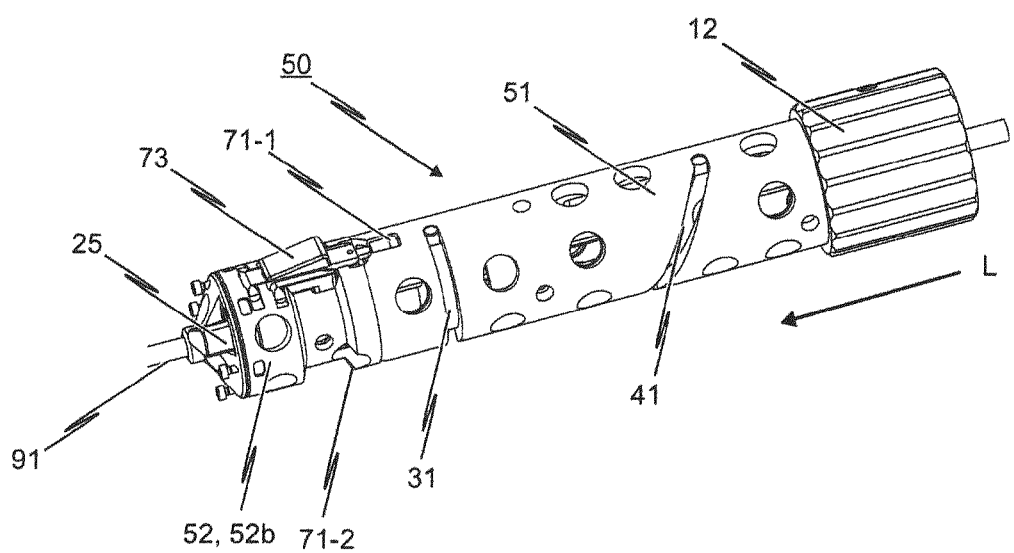
Figure 28:
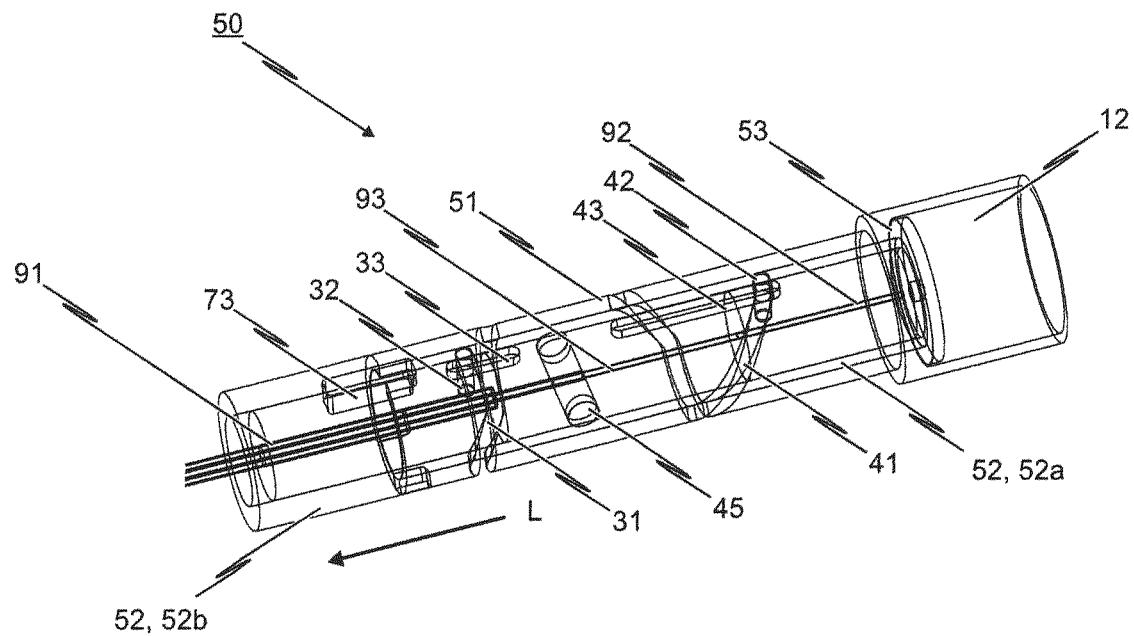
Figure 29:
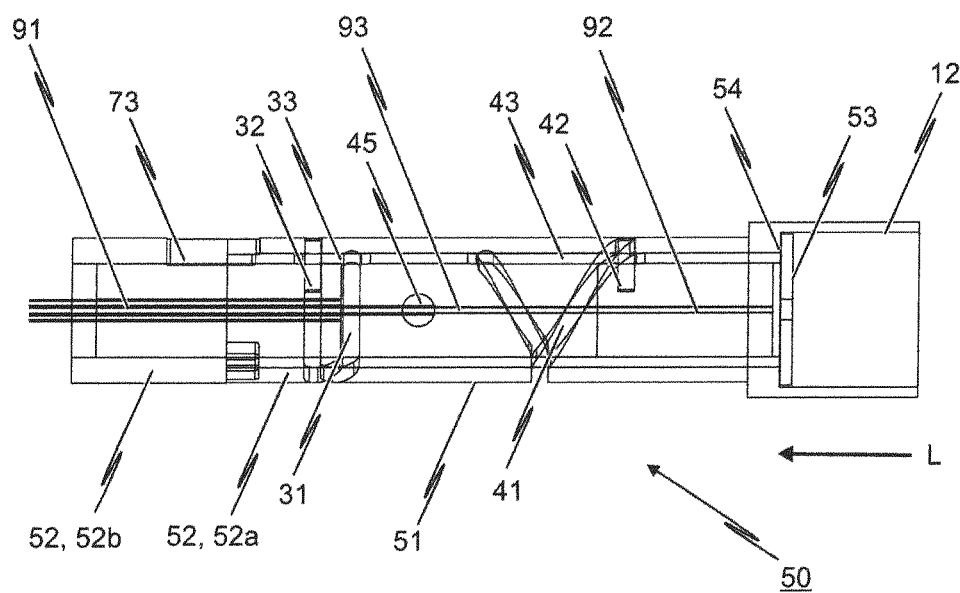

FIG. 1: illustrates aspects of the human heart anatomy;

FIG. 2a: illustrates schematically a retrograde implantation procedure of a heart valve stent;

FIG. 2b: illustrates schematically a antegrade implantation procedure of a heart valve stent;

FIG. 3: illustrates an exemplary embodiment of a heart valve prosthesis comprising a heart valve stent and a prosthetic heart valve attached thereto, said heart valve prosthesis being adapted to be accommodated in a catheter tip of a medical catheter delivery system according to the present disclosure;

FIG. 4: illustrates schematically an exemplary embodiment of a catheter tip of a medical catheter delivery system for retrograde insertion of an expandable heart valve prosthesis in a part-sectioned side elevation;

FIG. 5: illustrates schematically an exemplary embodiment of a catheter shaft of a medical catheter delivery system for retrograde insertion of an expandable heart valve prosthesis in a cross-sectional elevation;

FIGS. 6a to 6d: illustrate side elevations of an exemplary embodiment of a catheter tip of a medical catheter delivery system for retrograde insertion of an expandable heart valve prosthesis in different previously defined functional states for explaining a release procedure of a heart valve prosthesis accommodated in the catheter tip of the medical catheter delivery system;

FIGS. 6e, 6f: illustrate side elevations of the catheter tip in accordance with FIGS. 6a to 6d in two functional state after releasing a heart valve prosthesis which were accommodated in the catheter tip, wherein the catheter tip is ready to be removed from the body of a patient;

FIGS. 7a to 7c: illustrate schematically an exemplary embodiment of a catheter tip of a medical catheter delivery system for retrograde insertion of an expandable heart valve prosthesis in different functional states for explaining an implantation procedure of a heart valve prosthesis accommodated in the catheter tip;

FIG. 8: illustrates an exemplary embodiment of an operating handle of a medical catheter delivery system for retrograde insertion of an expandable heart valve prosthesis;

FIG. 9a: illustrates an exemplary embodiment of a hand grip of the operating handle in accordance with FIG. 8;

FIG. 9b: illustrates the hand grip in accordance with FIG. 9a in a side-sectional elevation;

FIG. 10: illustrates the exemplary embodiment of an operating handle in accordance with FIG. 8 without hand grip;

FIG. 11: illustrates schematically an exemplary embodiment of a cam mechanism utilized in the exemplary embodiment of the operating handle in accordance with FIG. 8;

FIG. 12: illustrates schematically the cam mechanism in accordance with FIG. 11 in a side-sectional elevation;

FIG. 13: illustrates a first component (cylindrical member) of the cam mechanism utilized in the exemplary embodiment of the operating handle in accordance with FIG. 8 in a perspective elevation;

FIG. 14: illustrates the first component (cylindrical member) member of the cam mechanism in accordance with FIG. 13 in a side elevation;

FIG. 15: illustrates a second component (body member) of the cam mechanism utilized in the exemplary embodiment of the operating handle in accordance with FIG. 8 in a perspective elevation;

FIG. 16: illustrates components (sliding members) received within the body member of the cam mechanism utilized in the exemplary embodiment of the operating handle in accordance with FIG. 8 in a perspective elevation;

FIGS. 17a, b: illustrate exemplary embodiments of sliding members adapted to be utilized in the exemplary embodiment of the operating handle in accordance with FIG. 8;

FIGS. 18a, b: illustrate a cross-sectional view of the operating handle in accordance with FIG. 8;

FIG. 19: illustrates a rear side (closed) of the exemplary embodiment of the operating handle in accordance with FIG. 8 in a perspective elevation;

FIGS. 20a to c: illustrate the open rear side of the operating handle in accordance with FIG. 19 for explaining an exemplary embodiment of selectively separating an operative linkage between a sliding member of the cam mechanism of the operating handle and a manipulating part of the operating handle;

FIG. 21: illustrates an exemplary embodiment of a locking mechanism of the operating handle in accordance with FIG. 8 in a perspective elevation;

FIG. 22: illustrates the locking mechanism in accordance with FIG. 21 in a side-sectional elevation;

FIGS. 23a to c: illustrate an exemplary embodiment of operating the locking mechanism in accordance with FIG. 21;

FIG. 24: illustrates schematically an exemplary embodiment of a catheter tip of a medical catheter delivery system for antegrade insertion of an expandable heart valve prosthesis in a part-sectioned side elevation;

FIGS. 25a to d: illustrate schematically an exemplary embodiment of a catheter tip of a medical catheter delivery system for antegrade insertion of an expandable heart valve stent in different functional states for explaining a releasing procedure of a heart valve stent accommodated in the catheter tip of the medical catheter delivery system;

FIG. 26: illustrates an exemplary embodiment of an operating handle of a medical catheter delivery system for antegrade insertion of an expandable heart valve prosthesis;

FIG. 27: illustrates the exemplary embodiment of the operating handle in accordance with FIG. 26 without hand grip;

FIG. 28: illustrates schematically an exemplary embodiment of a cam mechanism utilized in the operating handle in accordance with FIG. 26 in a perspective elevation; and FIG. 29: illustrates schematically the cam mechanism in accordance with FIG. 28 in a side-sectional elevation.

Both the right and left halves of the human heart consist of a ventricle and an atrium. These cavities are separated by the septum of the heart, divided into the atrial septum (septum interatriale) and the ventricular septum (septum interventriculare).

Blood can only flow in one direction through the chambers of the heart due to the cardiac valves situated between the atria and ventricles and in the arteries connected to the ventricles which function like mechanical valves. The superior and inferior vena cava (vena cava superior et inferior) flow into the right atrium. They supply the oxygen-depleted (venous) blood from the systemic circulation to the heart. The tricuspid valve which, like a mechanical valve, prevents a reverse flow of blood into the atrium upon ventricular contraction (systole) is situated between the right atrium and the right ventricle. It comprises three segments which are affixed like flaps to the ventricular musculature by ligaments (hence also called the "flap valve"). The two pulmonary arteries depart the right ventricle of the heart via a common trunk (truncus pulmonalis). There is also a valve between the ventricle and the pulmonary trunk, the so-called pulmonary valve. This type of valve is also called a semi-lunar valve due to its shape. The pulmonary arteries supply the oxygen-depleted blood to the pulmonary circulation.

Oxygen-rich (arterial) blood then usually flows through four pulmonary veins from the pulmonary circulation to the left atrium. From there, it reaches the left ventricle through a further flap valve, the mitral valve. The outflow is carried by the aorta which, like the pulmonary artery, has a semi-lunar valve (aortic valve).

During a heart cycle, the atria are filled first while the ventricles concurrently disgorge the blood into the arteries. When the ventricular musculature relaxes, the flap valves open due to the drop in pressure in the ventricle and the blood flows in from the atria (auricular systole). This is supported by a contraction of the atria. Ventricular contraction follows: the ventricular musculature contracts, the pressure rises, the flap valves close and the blood can now only flow into the arteries through the now-opened semi-lunar valves. A reverse blood flow from the arteries during the relaxation phase (diastole) is prevented by the closing of the semi-lunar valves such that the direction of flow is determined solely by the valves.

The four cardiac valves work like mechanical valves in the heart and prevent a reverse flow of blood in the wrong direction. Each half of the heart has a flap valve (atrioventricular valve) and a semi-lunar valve. The atrioventricular valves are situated between the atrium and the ventricle and are called the bicuspid/mitral valve and the tricuspid valve. The semi-lunar valves are situated between the ventricle and the vascular outflow and are called the pulmonary valve and the aortic valve respectively.

A valve defect, i.e. a dysfunction of a cardiac valve's function, can affect any of the four cardiac valves, although the valves on the left side of the heart (aortic and mitral valves) are affected considerably more frequently than those on the right side of the heart (pulmonary and tricuspid valves). Dysfunction can encompass constriction (stenosis), insufficiency or a combination of the two (combined vitium).

In medicine, the term "aortic valve insufficiency", or "aortic insufficiency" for short, refers to the defective closing of the heart's aortic valve and the diastolic reverse flow of blood from the aorta into the left ventricle as a result. Depending on the severity of the aortic insufficiency and the extent of resistance to aortic depletion, the volume of reverse flow can be up to two thirds of the left ventricle's ejection volume (normal cardiac output: 40 to 70 ml). This results in characteristically high blood pressure amplitude. This regurgitated blood flow increases the diastolic filling of the left chamber and leads to a volume overload of this section of the heart, a consequence of which is eccentric hypertrophy.

Aortic valve stenosis is a valvular heart disease caused by the incomplete opening of the aortic valve. When the aortic valve becomes stenotic, it causes a pressure gradient between the left ventricle and the aorta. The more constricted the valve, the higher the gradient between the left ventricle and the aorta. For instance, with a mild aortic valve stenosis, the gradient may be 20 mmHg. This means that, at peak systole, while the left ventricle may generate a pressure of 140 mmHg, the pressure that is transmitted to the aorta will only be 120 mmHg.

In individuals with aortic valve stenosis, the left ventricle has to generate an increased pressure in order to overcome the increased afterload caused by the stenotic aortic valve and eject blood out of the left ventricle. The more severe the aortic stenosis, the higher the gradient is between the left ventricular systolic pressures and the aortic systolic pressures. Due to the increased pressures generated by the left ventricle, the myocardium (muscle) of the left ventricle undergoes hypertrophy (increase in muscle mass).

Angina in the setting of aortic valve stenosis is secondary to the left ventricular hypertrophy that is caused by the constant production of increased pressure to overcome the pressure gradient caused by the aortic valve stenosis. While the myocardium (i.e. heart muscle) of the left ventricle gets thicker, the arteries that supply the muscle do not get significantly longer or bigger, so the muscle may become ischemic (i.e. doesn't receive an adequate blood supply). The ischemia may first be evident during exercise, when the heart muscle requires increased blood supply to compensate for the increased workload. The individual may complain of exertional angina. At this stage, a stress test with imaging may be suggestive of ischemia.

Mitral valve insufficiency (also called "mitral insufficiency") is a frequent cardiac valve defect in human medicine and also in at least some animal species. It involves a closing defect or "leakage" of the heart's mitral valve which leads to reverse blood flow from the left ventricle into the left atrium during the ejection phase (systole).

The mitral valve functions like a mechanical valve between the left atrium and the left ventricle of the heart. It opens during the filling phase of the ventricle (diastole) and thus enables the inflow of blood from the atrium. At the beginning of the ejection phase (systole), the sudden increase in pressure in the ventricle leads to the closing of the valve and thus to a "sealing" of the atrium. In so doing, a pressure of only about 8 mmHg prevails in the atrium, while at the same time the systolic pressure of about 120 mmHg in the ventricle forces the blood along its usual path into the main artery (aorta).

In cases of severe mitral insufficiency, however, the regurgitation opening is larger than 40 mm$^2$ and the regurgitation volume greater than 60 ml, which can lead to serious and at times life-threatening changes.

In the acute stage, with a normal size to the left ventricle and the left atrium, there is a considerable increase of the pressure in the atrium and thus also in the pulmonary veins. This can be up to 100 mmHg which, given a normal condition to the pulmonary vessels, leads to immediate pulmonary oedema. The then predominantly reverse blood flow can result in insufficient outflow into the aorta and thus decreased blood flow to all the organs.

To treat a severe narrowed cardiac valve or cardiac valve insufficiency, it is necessary for a valvular prosthesis (hereinafter also referred as "heart valve prosthesis") to perform the valve function of the narrowed, diseased or diseased cardiac valve. Essential in this respect is that the valvular prosthesis is securely positioned and anchored in the implantation site in the heart; i.e. in the plane of the (diseased) cardiac valve to be replaced, so that the valvular prosthesis is not displaced or shifted despite the, at times considerable, forces acting on it. An effective seal during systole is also important.

Over the past few years, minimally invasive interventional procedures for the treatment of a severe narrowed cardiac valve or cardiac valve insufficiency have become an established therapeutic alternative to "conventional" open surgical procedures. Certain procedures, however, involve placement of relatively large devices into targeted locations within tissue structures. Procedures such as aortic valve replacement conventionally have been addressed with open surgical procedures which are highly invasive. More recently, such procedures have been attempted using natural lumen excess and catheter delivery systems.

Referring to the human heart anatomy illustrated in FIG. 1, such natural lumen access and delivery systems typically are configured, for example, to reach the aortic valve location 212 inside of the heart 202 from an antegrade approach, i.e. performed in the normal direction of blood flow. An antegrade approach, however, generally requires navigating instrumentation through the right ventricle 222, the left atrium, and the left ventricle 220 of the beating heart 202, by way of the mitral valve 210.

A retrograde approach, i.e. an access performed backward or against the usual direction of blood flow, is an alternative to reach the aortic valve location 212 inside of the heart 202. A retrograde approach generally requires navigating instrumentation along the aortic arch, from the descending aorta 204 to the ascending aorta 206 and adjacent the aortic valve 212.

A transarterial access to the heart 202 of a patient as an example for a retrograde approach is schematically shown in FIG. 2a. In the illustration in accordance with FIG. 2a, a heart valve stent 100 is advanced with the aid of a medical catheter delivery system (only schematically shown) via the femoral artery to the aortic valve 212.

In some cases, a retrograde approach cannot be used in patients who have small or tortuous femoral or iliac vessels or severe peripheral vascular disease such as persons with previous aortobifemoral grafting. Rather, for such patients, an antegrade approach, for example a transarterial, transfemoral or transsubclavian approach, is preferred, whereby the surgeon creates a transcutaneous access to the region around the apex 224 of the beating heart 202 with a surgical thoracotomy, followed by direct access to the left ventricle 220 using a needle or other puncture device aimed to access the left ventricle 220 around the left ventricular apex 224.

Aspects of an antegrade (transapical) access procedure are illustrated in FIG. 2b, wherein the pericardium is opened by using a needle device for puncturing the muscular heart wall to gain access of the left ventricle 220 around the location of the left ventricular apex 224. A guidewire 180 may be advanced toward and through the aortic valve 212 to assist with diagnostic and interventional aspects of the procedure. After treatment of the heart 202, the apex 224 is closed, for example, by using a purse-string suture technique. A purse-string suture is a continuous suture placed in a circle about a round wound or punctures which needs to be closed. The opening is closed by tightly drawing the ends of the suture together.

An exemplary embodiment of a heart valve prosthesis 150 comprising a heart valve stent 100 and a prosthetic heart valve 200 affixed thereto is illustrated in FIG. 3.

The exemplary embodiment of a heart valve prosthesis 150 as schematically illustrated in FIG. 3 is adapted for the treatment of a narrowed cardiac valve or a cardiac valve insufficiency.

The following description will make reference to FIG. 3 to briefly describe the structure and function of the exemplary embodiment of the heart valve prosthesis 150. The heart valve prosthesis 150 comprises a heart valve stent 100 which exhibits an expandable structure which is able to transform from a first predefinable shape, in which the stent 100 is in a collapsed state, into a second predefinable shape in which the stent 100 is in an expanded state. The heart valve stent 100 together with a prosthetic heart valve 200 affixed thereto is introduced in a minimally invasive fashion into the body of a patient in its first shape using a catheter delivery system. During (antegrade or retrograde) insertion by way of a catheter delivery system, the prosthetic heart valve 200 affixed to the stent 100 is likewise in a collapsed state.

The exemplary embodiment of a heart valve prosthesis 150 depicted in FIG. 3 is adapted to be introduced with a retrograde approach or an antegrade approach by way of a catheter delivery system to be described latter.

Upon reaching the site of implantation in the patient's heart, the stent 100 transforms into its second (expanded) shape in which the valvular prosthesis 200 affixed to the stent 100 also unfolds and expands. The second expanded shape is a permanent shape that has been set by programming. FIG. 3 shows the exemplary embodiment of the heart valve prosthesis 150 in a completely expanded state.

The stent 100 according to the exemplary embodiment of the heart valve prosthesis 150 depicted in FIG. 3 has a total of three positioning arches 115a, 115b, 115c which assume a function of self-positioning the stent 100 into the plane of a native pulmonary valve (valva trunci pulmonalis) or a native aortic valve (valva aortae). Each of the positioning arches 115a, 115b, 115c exhibits a rounded head portion 120 which are designed to engage in the pockets T of a (diseased) native cardiac valve to be treated during positioning of the stent 100 at the site of implantation in the heart.

Further details regarding the implantation procedure of a heart valve prosthesis 150 of the kind as depicted in FIG. 3 are described below with reference to FIGS. 7a to 7c, which illustrate schematically an exemplary embodiment of a catheter tip of a medical catheter delivery system for retrograde insertion of an expandable heart valve prosthesis in different functional states to illustrate a implantation procedure of a heart valve prosthesis accommodated in the catheter tip.

As well as providing a symmetry that matches that of the native valve, the provision of a total of three positioning arches 115a, 115b, 115c also provides rotational accuracy, symmetry and stability. The stent 100 is of course not limited to the use of a total of three positioning arches 115a, 115b, 115c.

The head portions 120 of the positioning arches 115a, 115b, 115c, respectively pointing towards an inflow end region of the stent 100, are rounded so that the vascular wall will not be damaged when the positioning arches 115a, 115b, 115c engage in the pockets T of the native cardiac valve to be replaced. To improve movement and position analysis during the implanting of the stent 100 reference markers may be provided on or within the head portions 120 of the positioning arches 115a, 115b, 115c. Radio opaque markers or markers which can be activated by infrared or ultrasound lend themselves particularly well hereto.

As shown in FIG. 3, the positioning arches 115a, 115b, 115c of the heart valve stent 100 respectively exhibit an essentially U-shaped or V-shaped structure which is closed to the inflow end of stent 100. Accordingly, each positioning arch 115a, 115b, 115c has a total of two arms respectively extending from the head portion 120 of the associated positioning arch 115a, 115b, 115c towards an outflow end of stent 100. By doing so, each two adjoining arms of two neighbouring positioning arches 115a, 115b, 115c are connected to one another via a connecting portion.

For implanting and explanting the stent 100 with a suitable catheter delivery system, the stent 100 comprises catheter retaining elements 123 preferably at its outflow end region. The catheter retaining elements 123 may comprise oval-shaped heads which each may comprise a corresponding oval-shaped eyelet 124. The shape of the catheter retaining elements 123 complements stent retaining elements of a crown on the catheter tip of a catheter delivery system used to implant/explant the stent 100.

Exemplary embodiments of a catheter tip of a catheter delivery system having stent retaining elements are described below with reference to FIG. 4 and FIG. 24. In more detail, FIG. 4 illustrates schematically an exemplary embodiment of a catheter tip of a medical catheter delivery system for retrograde insertion of an expandable heart valve prosthesis in a part-sectioned side elevation, whereas an exemplary embodiment of a catheter tip of a medical catheter delivery system for antegrade insertion of an expandable heart valve prosthesis in a part-sectioned side elevation is illustrated schematically in FIG. 24.

In particular, the stent retaining elements of the catheter tip of a catheter delivery system (hereinafter also referred as "stent holder") may have protruding elements that are configured as a negative of the catheter retaining elements 123 provided preferably at the outflow end region of the stent 100.

Alternatively, the protruding elements of the stent retaining elements of the catheter tip may be shaped to be complementary to the eyelets 124 of the catheter retaining elements 123 provided preferably at the outflow end region of the stent 100 and are configured as catheter retaining heads. This realization enables the protruding elements of the crown to form a releasable engagement with the outflow area of stent 100 to allow releasable attachment of the stent 100 to the catheter tip.

Referring back to FIG. 3, the heart valve stent 100 of the exemplary embodiment of the heart valve prosthesis 150 is further provided with retaining arches 116a, 116b, 116c at which the prosthetic heart valve 200 is fastened in particular by way of a thread or a thin wire. It is easily recognized that the widening of the centre area and the inflow end region of the stent 100, at which the prosthetic heart valve 200 is disposed, achieves spreading of the prosthetic heart valve 200.

Exemplary embodiments of a medical catheter delivery system suitable for introducing a heart valve prosthesis, for example a heart valve prosthesis 150 of the kind as shown in FIG. 3, into a body of a patient are described in the following.

In accordance with some embodiments of the present disclosure, the medical catheter delivery system for introducing an expandable heart valve prosthesis 150 into the body of a patient is constituted as catheter system having a catheter tip 80-1, 80-2 at a distal end portion of the catheter delivery system. The catheter tip 80-1, 80-2 is capable of accommodating at least partly a preferably tightly compressed heart valve prosthesis 150 or heart valve stent 100.

According to some aspects of the present disclosure, the catheter system further comprises an operating handle 10-1, 10-2 at a proximal end portion of the catheter system. The operating handle 10-1, 10-2 is configured for manipulating the catheter tip 80-1, 80-2 which becomes necessary for releasing a heart valve prosthesis 150 accommodated in the catheter tip 80-1, 80-2, for example, at an implantation side inside the patient's body.

In some embodiments of the present disclosure, the operating handle 10-1, 10-2 of the catheter system is operatively connected with the catheter tip 80-1, 80-2 by way of a catheter shaft 90. In case the catheter system is designed for retrograde access, preferably at least a distal end portion of the catheter shaft 90 is flexible enough such that the catheter tip 80-1 and the distal end portion of the catheter shaft 90 may pass the aortic arch, in particular during insertion through the aorta of a patient.

An exemplary embodiment of a catheter tip 80-1 of a medical catheter delivery system for retrograde (for example transarterial, transfemoral or transsubclavian) insertion of an expandable heart valve prosthesis 150 or an expandable heart valve stent 100 is described in the following with reference to FIG. 4.

In more detail, FIG. 4 illustrates schematically an exemplary embodiment of a catheter tip 80-1 of a medical catheter delivery system for retrograde insertion of an expandable heart valve prosthesis (not shown in FIG. 4) in a part-sectioned side elevation. For example, a heart valve prosthesis 150 of the kind as shown in FIG. 3 could be inserted into the body of a patient by way of the exemplary embodiment of a catheter tip 80-1 illustrated in FIG. 4.

In the exemplary embodiment depicted in FIG. 4, the catheter tip 80-1 has a seat portion for accommodating a heart valve prosthesis 150 or a heart valve stent 100 to be inserted in its collapsed state. Furthermore, the catheter tip 80-1 is provided with stent retaining element 85 for releasably fixing a heart valve prosthesis 150 or a heart valve stent 100 in the seat portion of the catheter tip 80-1. In the embodiment illustrated in FIG. 4, the stent retaining element 85 comprises a crown having attachment elements 86 for releasably connecting with catheter retaining elements 123 of a heart valve prosthesis 150 or a heart valve stent 100 to be implanted. Hence, the stent retaining element 85 of the catheter tip 80-1 functionally serves as a "stent holder".

In accordance with some aspects of the present disclosure, the seat portion of the catheter tip 80-1 is constituted by at least one sleeve-shaped member. In the exemplary embodiment depicted in FIG. 4, the seat portion of the catheter tip 80-1 comprises a total of two sleeve-shaped members: a first sleeve-shaped member 81 and a second sleeve-shaped member 82. As illustrated, the respective cross-sections of the two sleeve-shaped members 81, 82 are preferably identical to each other such that the first and second sleeve-shaped members 81, 82 can completely enclose a heart valve stent 100 or a heart valve prosthesis 150 accommodated in the catheter tip 80-1.

For releasing a heart valve stent 100 or heart valve prosthesis 150 accommodated in the catheter tip 80-1, the first and second sleeve-shaped members 81, 82 are movable relatively to each other and also relatively to the stent retaining element 85 (stent holder) used for releasably fixing a heart valve stent 100 or heart valve prosthesis 150 to the catheter tip 80-1.

For this purpose, a first force transmitting member having a distal end portion connected to the first sleeve-shaped member 81 is provided. The first force transmitting member is allocated to the first sleeve-shaped member 81 of the catheter tip 80-1 and has a proximal end portion opposite to the distal end portion, the proximal end portion of the first force transmitting member being operatively connected to a corresponding (first) sliding member 30 of an operating handle 10-1, 10-2 of the catheter delivery system. An exemplary embodiment of an operating handle 10-1 having a corresponding (first) sliding member 30 for manipulating the first sleeve-shaped member 81 of the catheter tip 80-1 illustrated in FIG. 4 is described below with reference to FIGS. 8 to 23.

In addition, a second force transmitting member having a distal end portion connected to the second sleeve-shaped member 82 is provided. The second force transmitting member is allocated to the second sleeve-shaped member 82 of the catheter tip 80-1 and has a proximal end portion opposite to the distal end portion, the proximal end portion being operatively connected to a corresponding (second) sliding member 40 of an operating handle 10-1 of the catheter deliver system. An exemplary embodiment of an operating handle 10-1 having a corresponding (second) sliding member 40 for manipulating the second sleeve-shaped member 82 of the catheter tip 80-1 illustrated in FIG. 4 is described below with reference to FIGS. 8 to 23.

When manipulating the respective sliding members 30, 40 of the operating handle 10-1, the first and/or second sleeve-shaped members 81, 82 may be moved relatively to each other and relatively to the stent retaining element 85 (stent holder) of the catheter tip 80-1.

FIG. 5 illustrates schematically an exemplary embodiment of a catheter shaft 90 of a medical catheter delivery system adapted for retrograde (for example transarterial, transfemoral or transsubclavian) insertion of a heart valve prosthesis 150.

As can be seen from FIG. 5, the first force transmitting member allocated to the first sleeve-shaped member 81 of the catheter tip 80-1 and operatively connected with a first sliding member 30 of the operating handle 10-1 may be constituted by a first catheter tube 91 defining a first lumen. The second force transmitting member allocated to the second sleeve-shaped member 82 of the catheter tip 80-1 and operatively connected with a second sliding member 40 of the operating handle 10-1 may be constituted by a further (second) catheter tube 92 defining a further (second) lumen. In the exemplary embodiment depicted in FIG. 5, the second catheter tube 92 has a cross-sectional diameter less than the cross-sectional diameter of the first catheter tube 91. The first catheter tube 91 is disposed concentrically and coaxially with the second catheter tube 92 and the second catheter tube 92 is received within the first lumen defined by the first catheter tube 91.

Contrary to the first and second sleeve-shaped members 81, 82 of the catheter tip 80-1, however, the stent retaining element 85 (stent holder) of the catheter tip 80-1 is preferably not axially movable relatively to the operating handle 10-1 of the catheter system. Rather, the stent retaining element 85 is preferably connected to an anchorage 45 of the operating handle 10-1 by using a further catheter tube 93 having a distal end portion connected to the stent retaining element 85, and further having a proximal end portion connected to an anchorage 45 of the operating handle 10-1. Hereinafter, this further catheter tube 93 is also referred as "stent holder tube".

Referring again to the exemplary embodiment depicted in FIG. 5, the stent holder tube 93 may have a cross-sectional diameter less than the cross-sectional diameter of the first catheter tube 91. In particular, the first catheter tube 91 may be disposed concentrically and coaxially with both, the stent holder tube 93 on the one hand and the second catheter tube 92 on the other hand. Preferably, the stent holder tube 93 has a cross-sectional diameter less than the cross-sectional diameter of the first catheter tube 91 and greater than the cross-sectional diameter of the second catheter tube 92 such that the stent holder tube 93 is received within the first lumen defined by the first catheter tube 91. The second catheter tube 92 is preferably received within a passageway defined by the stent holder tube 93.

In the exemplary embodiment schematically illustrated in FIG. 5, the passageway defined by the stent holder tube 93 has a diameter sufficient to accommodate the second catheter tube 92 such that the second catheter tube 92 is movable relatively to the stent holder tube 93.

The second lumen defined by the second catheter tube 92 has preferably a diameter sufficient to accommodate a guidewire 180. The second catheter tube 92 may be made from a rigid material including, for example, nitinol, stainless steel or a rigid plastic material. The material of the distal end portion of the second catheter tube 92 may have an increased flexibility compared to the material of the proximal end portion in order to allow the distal end portion of the catheter shaft 90 to pass the aortic arch during insertion of the catheter tip 80-1. For example, the first catheter tube 91 may be a 12F-catheter tube. This particularly applies for a catheter delivery system designed for retrograde (for example transarterial, transfemoral or transsubclavian) access.

Reference is made again to the exemplary catheter tip 80-1 for retrograde insertion of an expandable heart valve prosthesis illustrated schematically in FIG. 4.

As can be seen from the exemplary embodiment of the catheter tip 80-1 depicted in FIG. 4, the distal end portion of the second catheter tube 92 terminates in a soft catheter end tip 94 which preferably has an atraumatic shape. The soft catheter end tip 94 is provided with a channel aligned with the second lumen defined by the second catheter tube 92 such that a guidewire 180 accommodated within the second lumen defined by the second catheter tube 92 may pass through the channel of the soft catheter end tip 94.

The second sleeve-shaped member 82 of the catheter tip 80-1 is connected to the soft catheter end tip 94 such that the opened end of the second sleeve-shaped member 82 faces in the proximal direction opposite to the direction of the soft catheter end tip 94, i.e. in the direction of an operating handle 10-1 of the catheter delivery system.

According to the exemplary embodiment depicted in FIG. 5, the stent holder tube 93 is preferably made of a rigid material, for example, a rigid plastic material, stainless steel or nitinol. The distal end portion of the stent holder tube 93 terminates in the stent retaining element 85 and, in more detail, in a crown (stent holder) of the stent retaining element 85. The crown is preferably also made of a rigid material, for example, a rigid plastic material or stainless steel. The passageway defined by the stent holder tube 93 is aligned with a channel which passes through the crown (stent holder) of the stent retaining element 85. In this way, the second catheter tube 92 is accommodated in the passageway of the stent holder tube 93 and in the channel of the crown of the stent retaining element 85 such as to be movable relatively to the stent holder tube 93 and the crown (stent holder) of the stent retaining element 85.

In the exemplary embodiment depicted in FIG. 5, the first catheter tube 91 is preferably made of a bendable but inelastic material. For example, the first catheter tube 91 may be at least partly made of a braided or non-braided catheter tube. In more detail, the first catheter tube 91 is preferably adapted to transfer compression and tension forces from corresponding operating mechanisms (first sliding member 30) of an operating handle 10-1 of the catheter delivery system to the first sleeve-shaped member 81 of the catheter tip 80-1 without overly changing its total length.

The distal end portion of the first catheter tube 91 preferably terminates at a flared section 83 as a transition to the section defining the first sleeve-shaped member 81 of the catheter tip 80-1.

As can be seen from FIG. 4, the flared section 83 and the first sleeve-shaped member 81 may be formed integrally and may be connected to the distal end portion of the first catheter tube 91. In addition, the flared section 83 may constitute the first sleeve-shaped member 81 of the catheter tip 80-1. The first sleeve-shaped member 81 and the flared section 83 of the first catheter tube 91 may be all of the same material and originating from the same raw tube prior to a widening process so that the flared section 83 and the first sleeve-shaped member 81 may be the same elements.

In accordance with some aspects of the present disclosure, a catheter delivery system designed for retrograde (for example transarterial, transfemoral or transsubclavian) access comprises a catheter tip 80-1 for accommodating a heart valve stent 100, with a heart valve prosthesis 150 fastened to it. For example, in the exemplary embodiment depicted in FIG. 4, the catheter tip 80-1 consists of a first sleeve-shaped member 81, particularly for accommodating positioning arches 115*a*, 115*b*, 115*c* of a heart valve stent 100, and a second sleeve-shaped member 82, in particular for accommodating retaining arches 116*a*, 116*b*, 116*c* and a heart valve prosthesis 150 fastened to it.

The catheter delivery system in accordance with some embodiments of the present disclosure is adapted to release an expandable heart valve prosthesis 150 accommodated in the catheter tip 80-1 of the catheter delivery system in a previously definable sequence of events in steps. For this reason, the first and second sleeve-shaped members 81, 82 of the catheter tip 80-1 are movable relatively to each other and relatively to the stent retaining element 85 (stent holder) of the catheter tip 80-1. A manipulation of the respective sleeve-shaped members 81, 82 of the catheter tip 80-1 can be affected on actuation of respective sliding members 30, 40 of the operating handle 10-1 with which the sleeve-shaped members 81, 82 of the catheter tip 80-1 are operatively connected.

In more detail, according to some embodiments of the present disclosure, the first sleeve-shaped member 81 of the catheter tip 80-1 is operatively connected with a first sliding member 30 of a corresponding operating handle 10-1 by way of first force transmitting mechanism, for example, a first catheter tube 91. On the other hand, the second sleeve-shaped member 82 of the catheter tip 80-1 is operatively connected with a corresponding second sliding member 40 of the operating handle 10-1 by way of second force transmitting mechanism, for example, further (second) catheter tube 92. As already indicated, the stent retaining element 85 (stent holder) of the catheter tip 80-1 is preferably not movable in the longitudinal direction relatively to the operating handle 10-1. Accordingly, the stent retaining element 85 is preferably not operatively connected with a corresponding (manipulatable) sliding member of the operating handle 10-1. Rather, according to preferred embodiments of the present disclosure, the stent retaining element 85 of the catheter tip 80-1 is connected, for example by way of a stent holder tube 93, with an anchorage 45 of the operating handle 10-1.

In the exemplary embodiment depicted in FIG. 4, the catheter tip 80-1 is illustrated in a first functional state, in which the catheter tip 80-1 and, for example a heart valve prosthesis 150 accommodated in it, can be inserted into the patient transarterially, transfemorally or transsubclavianally and advanced via the aorta to the implantation side. Accordingly, in the first functional state, the catheter tip 80-1 is completely closed whereby the respective open end sections of the two sleeve-shaped members 81, 82 of the catheter tip 80-1 abut against each other.

Alternatively, the two sleeve-shaped members 81, 82 of the catheter tip 80-1 may also at least partly overlap telescopically. Accordingly, in the first functional state of the catheter tip 80-1, the two sleeve-shaped members 81, 82 provide for a seat portion adapted for accommodating an at least partly preferably tightly compressed heart valve prosthesis 150.

On reaching an implantation location in the patient's body, the catheter tip 80-1 is transferred from its first functional state into a second functional state by transferring the first sliding member 30 of the operating handle 10-1 from a first position into a second position. The longitudinal (axial) displacement stroke transferred by actuation of the first sliding member 30 to the operatively connected first sleeve-shaped member 81 of the catheter tip 80-1 affects a axial displacement of the first sleeve-shaped member 81 relative to the stent retaining element 85 (stent holder) and the second sleeve-shaped member 82 of the catheter tip 80-1 in a proximal direction, thus towards the operating handle 10-1.

The longitudinal (axial) displacement stroke executed on the first sleeve-shaped member 81 of the catheter tip 80-1 during transition from the first functional state to the second functional state by the first sliding member 30 via a corresponding first force transmitting mechanism (for example first catheter tube 91) is previously defined so that the first sleeve-shaped member 81 is displaced relatively to the stent retaining element 85 (stent holder) of the catheter tip 80-1 in the proximal direction just so far that only a predetermined portion of a heart valve prosthesis 150 housed in the catheter tip 80-1 would be released. In more detail, the distal end portion of the first sleeve-shaped member 81 of the catheter tip 80-1 is still covering the stent retaining element 85 (stent holder) of the catheter tip 80-1, so that an engagement between catheter retaining elements 123 provided at a heart valve prosthesis 150 accommodated in the catheter tip 80-1 and the stent retaining element 85 (stent holder) of the catheter tip 80-1 would be secured.

Since the second sleeve-shaped member 82 of the catheter tip 80-1 is not manipulated during a transition from the first functional state into the second functional state, the retaining arches 116a, 116b, 116c of a heart valve stent 100 housed in the catheter tip 80-1 with a prosthetic heart valve 200 fastened to it would continue to be housed in its folded state in the second sleeve-shaped member 82 of the catheter tip 80-1.

However, the positioning arches 115a, 115b, 115c of a heart valve stent 100 housed in the catheter tip 80-1 are released in the second functional state of the insertion system. In more detail, the positioning arches 115a, 115b, 115c radially expand as a result of the radial forces acting on then and can thus be positioned in the pockets T of a native heart valve.

Following appropriate positioning of the positioning arches 115a, 115b, 115c of the stent 100 in the pockets T of the native heart valve, the catheter tip 80-1 of the catheter delivery system is transferred from the second functional state into a third functional state. This is done by manipulation of the second sliding member 40 of the operating handle 10-1 which is operatively connected with the second sleeve-shaped member 82 of the catheter tip 80-1, for example by way of a second catheter tube 92.

On actuation of the second sliding member 40 of the operating handle 10-1, the second sleeve-shaped member 82 of the catheter tip 80-1 is axially moved relatively to the stent retaining element 85 (stent holder) of the catheter tip 80-1 by a previously established longitudinal (axial) displacement stroke in a distal direction, thus away from the operating handle 10-1. The longitudinal (axial) displacement stroke acting on the second sleeve-shaped member 82 is chosen so that the second sleeve-shaped member 82 no longer covers the inflow region of a heart valve prosthesis 150 housed in the catheter tip 80-1, and thus releases the inflow region of the heart valve prosthesis 150. Due to the action of radial forces, the inflow region of the heart valve prosthesis 150 unfolds completely.

Since the first sliding member 30 of the operating handle 10-1 and the associated first sleeve-shaped member 81 of the catheter tip 80-1 are not manipulated during a transition from the second functional state into the third functional state, the distal end region of the first sleeve-shaped member 81 continues to cover the outflow end region of the heart valve prosthesis 150 and, in particular, the stent retaining element 85 (stent holder) of the catheter tip 80-1, so that an engagement between catheter retaining elements 123 of a heart valve prosthesis 150 housed in the catheter tip 80-1 and the stent retaining element 85 (stent holder) of the catheter tip 80-1 is secured and the outflow end region of the heart valve prosthesis 150 is still in its folded state.

The maintained anchorage of the heart valve prosthesis 150 to the catheter tip 80-1 also allows an explantation of the heart valve prosthesis 150 that is already partially unfolded by returning the catheter tip 80-1 from the third functional state by appropriate manipulation of the first and second sliding members 30, 40 of the operating handle 10-1, to the second functional state and then by suitable actuation of the first sliding member transferred to the first functional state.

If an explantation of the heart valve prosthesis 150 is unnecessary, the catheter tip 80-1 is transferred from the third functional state into a fourth functional state by moving the first sliding member 30 of the operating handle 10-1 further from the second position to a third position. The manipulation of the first sliding member 30 results in a further defined movement of the first sleeve-shaped member 81 of the catheter tip 80-1 relative to the stent retaining element 85 (stent holder) of the catheter tip 80-1 in a proximal direction, thus towards the operating handle 10-1. The longitudinal (axial) displacement stroke executed on the first sleeve-shaped member 81 is chosen so that the distal end of the first sleeve-shaped member 81 no longer covers the stent retaining element 85 (stent holder) of the catheter tip 80-1, as a result of which an engagement between catheter retaining elements 123 of a heart valve prosthesis 150 housed in the catheter tip 80-1 and the stent retaining element 85 (stent holder) of the catheter tip 80-1 can be released, which would also lead to a complete release of the outflow end region of the heart valve prosthesis 150 and a complete separation of the heart valve prosthesis 150 from the catheter tip 80-1 and correspondingly to a complete unfolding of the heart valve prosthesis 150.

A further exemplary embodiment of a catheter tip 80-1 of a catheter delivery system for retrograde (for example transarterial, transfemoral or transsubclavian) insertion of an expandable heart valve prosthesis 150 is shown in different functional states in FIGS. 6a to 6f.

In detail, the exemplary embodiment of the catheter tip 80-1 is shown in its first functional state in FIG. 6a, in which the catheter shaft 90 with the catheter tip 80-1 and a heart valve prosthesis 150 accommodated in the catheter tip 80-1 can be inserted into the patient transaterially or transfemorally and advanced, for example, via the aorta to the implantation side at the heart.

In the first functional state of the catheter tip 80-1 in accordance with FIG. 6a, the catheter tip 80-1 is completely closed, whereby the two sleeve-shaped members 81, 82 of the catheter tip 80-1 abut. According to the exemplary embodiment of the catheter tip 80-1 depicted in FIGS. 6a to 6f, the two sleeve-shaped members 81, 82 of the catheter tip 80-1 have an equal outer cross-sectional diameter, thereby not forming a step in the state depicted in FIG. 6a. The respective inner diameters of the sleeve-shaped members 81, 82 are chosen so that compressed retaining arches 116a, 116b, 116c of a heart valve stent 100 can be housed in the second sleeve-shaped member 82. Compressed positioning arches 115a, 115b, 115c of a heart valve stent 100 accommodated in the catheter tip 80-1 would be housed between the second sleeve-shaped member 82 and the first sleeve-shaped member 81 and would be held together in the compressed form.

In the first functional state of the catheter tip 80-1 as shown in FIG. 6a, the retaining region of the stent 100 at the stent's outflow end is fixed with stent retaining element 85 (stent holder) provided at a proximal end region of the catheter tip 80-1. For this purpose, catheter retaining elements 123 (e.g. retaining rings etc.) provided at a corresponding retaining region of the heart valve stent 100 are engaged with the stent retaining element 85 (stent holder) of the catheter tip 80-1.

The stent retaining element 85 (stent holder) of the catheter tip 80-1 are covered by the first sleeve-shaped member 81 of the catheter tip 80-1 in the first functional state shown in FIG. 6a, so that an engagement between catheter retaining elements 123 provided at a heart valve stent 100 accommodated in the catheter tip 80-1 and the stent retaining element 85 (stent holder) of the catheter tip 80-1 would be possible.

The first functional state of the catheter tip 80-1 shown in FIG. 6a is maintained during a retrograde (for example transarterial, transfemoral or transsubclavian) insertion procedure. On reaching an implantation location at the patient's heart, the catheter tip 80-1 is transferred from the first functional state shown in FIG. 6a to a second functional state shown in FIG. 6b by transferring a first sliding member 30 of an operating handle 10-1 operatively connected with the first sleeve-shaped member 81 of the catheter tip 80-1 from a first position into a second position. The longitudinal (axial) displacement stroke transferred by actuation of the first sliding member 30 to the first sleeve-shaped member 81 of the catheter tip 80-1 affects a displacement of the first sleeve-shaped member 81 relative to the stent retaining element 85 (stent holder) of the catheter tip 80-1 in the proximal direction, thus towards the operating handle 10-1.

The longitudinal (axial) displacement stroke executed on the first sleeve-shaped member 81 of the catheter tip 80-1 during the transition from the first functional state (see FIG. 6a) to the second functional state (see FIG. 6b) by the first sliding member 30 via corresponding first force transmitting mechanism is previously defined so that the first sleeve-shaped member 81 is displaced relatively to the stent retaining element 85 (stent holder) of the catheter tip 80-1 in the proximal direction just so far that positioning arches 115a, 115b, 115c of a heart valve stent 100 housed in the catheter tip 80-1 would be released. However, a distal end of the first sleeve-shaped member 81 of the catheter tip 80-1 still covers the stent retaining element 85 (stent holder) of the catheter tip 80-1, so that the engagement between catheter retaining elements 123 provided at a retaining region of the heart valve stent 100 and the stent retaining element 85 (stent holder) of the catheter tip 80-1 would be secured.

In the second functional state of the catheter tip 80-1 depicted in FIG. 6b, the first sleeve-shaped member 81 of the catheter tip 80-1 has already moved by a first predetermined amount of movement in a proximal direction, and thus towards the operating handle 10-1 of the catheter delivery system, leading to a release of positioning arches 115a, 115b, 115c of a stent 100 accommodated in the catheter tip 80-1. These positioning arches 115a, 115b, 115c of the stent 100 are positioned—where necessary by a suitable rotation of the stent retaining element 85 (stent holder) of the catheter tip 80-1—in the pockets T of the native heart valve. After positioning of the positioning arches 115 in the pockets T of the native heart valve is complete, the catheter tip 80-1 of the catheter delivery system is transferred from its second functional state (see FIG. 6b) into its third functional state (see FIG. 6c).

Since the first sliding member 30 of the operating handle 10-1 and the associated first sleeve-shaped member 81 of the catheter tip 80-1 are not manipulated during a transition from the second functional state in accordance with FIG. 6b into the third functional state in accordance with FIG. 6c, the distal end region of the first sleeve-shaped member 81 continues to cover the stent retaining element 85 (stent holder) of the catheter tip 80-1, so that the engagement between catheter retaining elements 123 of a stent 100 housed in the catheter tip 80-1 and the stent retaining element 85 (stent holder) of the catheter tip 80-1 is secure and the outflow region of the stent 100 is still in its folded-up state. This anchorage of the stent 100 to the catheter tip 80-1 of the catheter delivery system allows an explantation of a stent 100 that is already partially unfolded by returning the catheter tip 80-1 from the third functional state, by appropriate manipulation of the second sliding member 40 of the operating handle 10-1, to the second functional state and then by suitable actuation of the first sliding member 30 transfer to the first functional state.

If an explantation of the stent 100 with a prosthetic heart valve 200 attached to it, is unnecessary, the catheter tip 80-1 is transferred from the third functional state shown in FIG. 6c into the fourth functional state shown in FIG. 6d, by turning the first sliding member 30 of the operating handle 10-1 further from the second position to the third position. This manipulation of the first sliding member 30 results in a further defined movement of the first sleeve-shaped member 81 of the catheter tip 80-1 relative to the stent retaining element 85 of the catheter tip 80-1 in a proximal direction, i.e. thus towards the operating handle 10-1. The longitudinal (axial) displacement stroke executed on the first sleeve-shaped member 81 of the catheter tip 80-1 is chosen so that the distal end of the first sleeve-shaped member 81 no longer covers the stent retaining element 85 (stent holder), as a result of which an engagement between catheter retaining elements 123 of a stent 100 housed in the catheter tip 80-1 and the stent retaining element 85 (stent holder) can be released, which would also lead to a complete release of the outflow region of the stent 100 and a complete separation of the stent 100 from the catheter tip 80-1 and correspondingly to a complete unfolding of the stent 100 with a prosthetic heart valve 200 attached thereto.

In the exemplary embodiment of the catheter tip 80-1 depicted in FIGS. 6a to 6f, a stent holder tube 93 is used for connecting the stent retaining element 85 (stent holder) of the catheter tip 80-1 to an anchorage 45 fixed to a body portion of the operating handle 10-1. The stent holder tube 93 has a distal end connected to the stent retaining element 85 (stent holder) of the catheter tip 80-1, a proximal end connected to the body portion of the operating handle 10-1 and a passageway extending through the stent holder tube 93. In addition, an extension portion 93' of the stent holder tube 93 is provided, said extension portion 93' extending from the distal end of the stent retaining element 85 (stent holder) to a support section 94. The support section 94 may be a tapered portion which is completely accommodated in the second sleeve-shaped member 82 of the catheter tip 80-1 when the catheter tip 80-1 is in its first and second functional state (see FIGS. 6a and 6b).

Preferably, the stent holder tube 93 and its extension 93' have a cross-section less than the cross-section of the first catheter tube 91 and greater than the cross-section of the second catheter tube 92 (not shown in FIGS. 6a to 6f), wherein the first catheter tube 91 is disposed concentrically and coaxially with the stent holder tube 93 thereby accommodating the stent holder tube 93 such that the first catheter tube 91 is moveable relative to the stent holder tube 93. The passageway of the stent holder tube 93 may have a diameter sufficient to accommodate the second catheter tube 92 such that the second catheter tube 92 is moveable relative to the stent holder tube 93.

FIG. 6e shows a side elevation of the embodiment of the catheter tip 80-1 in accordance with FIGS. 6a to 6d, whereby the catheter tip 80-1 is in its state after releasing a stent 100, which was accommodated in the catheter tip 80-1. In this state of the catheter tip 80-1, the second sleeve-shaped member 82 of the catheter tip 80-1 is moved proximally, i.e. in the direction of the operating handle 10-1, by manipulation of the second sliding member 40 of the operating handle 10-1.

FIG. 6f shows a side elevation of the embodiment of the catheter tip 80-1 in accordance with FIG. 6e, whereby the catheter tip 80-1 is in its state ready to be removed again from the body of the patient. In this state of the catheter tip 80-1, the first sleeve-shaped member 81 of the catheter tip 80-1 is pushed by manipulation of the first sliding member 30 of the operating handle 10-1 such that the first sleeve-shaped member 81 is in its most distal position, in which the distal end of the first sleeve-shaped member 81 abuts against the proximal end of the second sleeve-shaped member 82 without any gap or step there between. For securing this gap- and step-free state, the distal end of the first sleeve-shaped member 81 and the proximal end of the second sleeve-shaped member 82 are supported by the already mentioned support section 94.

An exemplary embodiment of a medical device according to the present disclosure is described in the following. The medical device is adapted for the treatment of a heart valve defect, in particular a heart valve failure or a heart valve stenosis in a patient.

According to some aspects of the present disclosure, the medical device for the treatment of a heart valve defect comprises a catheter delivery system for introducing an expandable heart valve prosthesis into the body of a patient. The catheter delivery system comprises at least one sleeve-shaped member at a distal end portion of the catheter delivery system, the at least one sleeve-shaped member being part of a catheter tip of the catheter delivery system and capable of receiving at least partly a tightly compressed heart valve prosthesis. Preferably, the catheter tip of the catheter delivery system is provided with a total of two sleeve-shaped members, as will be described in more detail below with reference to FIGS. 7a to 7c.

In accordance with some embodiments of the present disclosure, the catheter delivery system further comprises an operating handle, for example an operating handle 10-1 of the kind as illustrated in FIG. 8. The operating handle 10-1 is disposed at a proximal end portion of the catheter delivery system and is adapted for manipulating the at least one sleeve-shaped member of the catheter tip. As described in more detail below, the operating handle may comprise a hand grip designed to be held by a user, and a manipulating part axially aligned with the hand grip.

According to some preferred embodiments of the present disclosure, the manipulating part of the operating handle is rotatable relatively to the hand grip about a longitudinal axis defined by the operating handle. In accordance with an aspect of the present disclosure, the operating handle comprises at least one sliding member operatively linked with the manipulating part of the operating handle by way of a cam mechanism such that, upon rotation of the manipulating part relative to the hand grip, the at least one sliding member moves axially in the direction of the longitudinal axis.

Reference is made in the following to FIGS. 7a to 7c which illustrate schematically an exemplary embodiment of a catheter tip 80-1 of a medical catheter delivery system for retrograde insertion of an expandable heart valve prosthesis 150 in different functional states for explaining an implantation procedure of the heart valve prosthesis 150 accommodated in the catheter tip 80-1.

In the exemplary embodiment of the medical device depicted in FIGS. 7a to 7c, an operating handle (not shown in FIGS. 7a to 7c) is provided at a proximal end region of a catheter shaft 90 of a catheter delivery system. The operating handle preferably comprises a total of two sliding members: a first sliding member operatively connected to a first sleeve-shaped member 81 of the catheter tip 80-1, and a second sliding member operatively connected to a second sleeve-shaped member 82 of the catheter tip 80-1.

According to some aspects of the present disclosure and as illustrated in FIGS. 7a to 7c, the medical device for the treatment of a heart valve defect further comprises an expandable heart valve stent 100 accommodated in the catheter tip 80-1 of the catheter delivery system.

As schematically shown in FIGS. 7a to 7c, a prosthetic heart valve 200 may be attached to the expandable heart valve stent 100 thereby forming a heart valve prosthesis 150.

Referring to FIGS. 7a to 7c, the exemplary embodiment of the medical device exhibits a catheter delivery system designed for retrograde (for example transarterial, transfemoral or transsubclavian) access. However, it is also possible for the medical device to exhibit a catheter delivery system which it is designed for an antegrade access, as will be described later with reference to FIGS. 25a to 25d.

In addition to the catheter delivery system, the medical device comprises a self-expandable heart valve stent 100 mounted in the catheter tip 80-1 of the catheter delivery system, to which a prosthetic heart valve 200 is fastened. In a first functional state, not shown in FIGS. 7a to 7c, the heart valve stent 100 exhibits a first previously definable configuration, in which it is in its folded-together state. On the other hand, the heart valve stent 100 is designed to adopt a second previously definable configuration in an implanted state, in which it exists in its expanded state.

Through the use of a catheter delivery system of the kind as disclosed herein, during the implantation procedure, the heart valve stent 100 is transferred sequentially, following a previously definable sequence of events in steps from its first previously defined configuration into its second previously defined configuration.

In detail, the heart valve stent 100 that is used with the medical device in accordance with FIGS. 7a to 7c exhibits a first retaining region, to which the prosthetic heart valve 200 is attached. Further, the stent 100 comprises catheter retaining elements 123, for example, in the configuration of retaining rings, which can be brought into a releasable engagement with stent retaining element 85 (stent holder) of the catheter tip 80-1.

In addition, the heart valve stent 100 may have a plurality of retaining arches 116 (in the embodiment depicted in FIGS. 7a to 7c, the heart valve stent 100 is provided with a total of three retaining arches 160) to accommodate a prosthetic heart valve 200, and a plurality of positioning arches 115 (in the embodiment depicted in FIGS. 7a to 7c, the heart valve stent 100 is provided with a total of three positioning arches) for automatic positioning of the stent 100 at the implantation site, whereby the respective positioning arches 115 of the stent 100 are designed in functional and structural respects to engage the pockets T of the native heart valve during an implantation procedure and in the implanted state of the stent 100, in particular from the second functional state of the catheter tip 80-1 of the catheter delivery system. In detail, each positioning arch 115 and its associated retaining arch 116 may have an essentially U or V-shaped structure, which is closed towards the inflow end of the stent 100.

The stent 100 and the prosthetic heart valve 200 attached thereto, which together with the catheter delivery system forms the basis of the medical device according to the present disclosure, is especially suitable for insertion into the body of a patient with minimal invasiveness. The distinctive feature of the heart valve stent 100 is that the positioning arches 115 of the stent 100 undertake the function of automatic positioning of the stent 100 with the prosthetic heart valve 200 attached to it in the aorta of the patient. The positioning arches 115 have radiused head sections, which engage in the pockets T of the insufficient heart valve to be replaced by the heart valve prosthesis 150 during positioning of the stent 100 at the implantation site. The provision of a total of at least three positioning arches 115 takes care of the necessary positioning accuracy in the rotary direction.

In the state shown in FIG. 7a, the catheter tip 80-1 and the distal part of the catheter delivery system have been inserted by a puncture of the groin artery of the patient and the catheter tip 80-1 has been advanced to the implantation site with the aid of a guidewire 180. In detail, the catheter tip 80-1 be used is shown already in its second functional state in FIG. 7a.

As already explained with reference, for example, to FIGS. 6a to 6f, in the second functional state of the catheter tip 80-1, the first sleeve-shaped element 81 of the catheter tip 80-1 has already moved by a first predetermined amount of movement in a proximal direction, and thus towards an operating handle 10-1 of the catheter delivery system, leading to a release of the positioning arches 115 of the catheter valve stent 100 accommodated in the catheter tip 80-1. These already expanded positioning arches 115 of the stent 100 shown in FIG. 7a are positioned, where necessary by a suitable rotation of the catheter tip 80-1, in the pockets T of the native heart valve.

After positioning of the positioning arches 115 in the pockets T of the native heart valve is complete, the catheter tip 80-1 of the catheter delivery system is transferred from its second functional state (see for example FIG. 6b) into its third functional state (see for example FIG. 6c).

The manner in which the catheter tip 80-1 is transferred from its second functional state into its third functional state has been described previously, for example with reference to FIG. 6c.

FIG. 7b shows the catheter tip 80-1 of the catheter delivery system in accordance with FIG. 7a, in which the second sleeve-shaped member 82 of the catheter tip 80-1 has been displaced in a distal direction so that the first retaining region of the stent 100 with the retaining arches 116 and the prosthetic heart valve 200 attached to them are released. These components (retaining arches 116 and prosthetic heart valve 200 attached thereto) are opened as a result of radial forces attacking on them, whereby the leaflets V of the native heart valve are clamped between the positioning arches 115 and the retaining arches 116 of the heart valve stent 100.

After functioning of the prosthetic heart valve 200 affixed to the (partly released) heart valve stent 100 has been checked, the catheter tip 80-1 of the catheter delivery system is then transferred from its third functional state into its fourth functional state, as has previously been described, for example with reference to FIG. 6d.

FIG. 7c shows the effect of a transfer of the catheter tip 80-1 of the catheter delivery system into its fourth functional state on the prosthetic heart valve 200 and the heart valve stent 100.

In detail, it can be seen that, in the fourth functional state of the catheter tip 80-1, the first sleeve-shaped member 81 of the catheter tip 80-1 has been displaced further in a proximal direction, as a result of which the anchorage of the catheter retaining elements 123 on the outflow end region of the stent 100 is released. This has the result that that this retaining region (=outflow region) of the stent 100 can also expand and press against the vessel wall.

Finally, the catheter tip 80-1 and the distal portion of the catheter delivery system are removed again from the body of the patient.

When the heart valve stent 100 is implanted, the leaflets V of the native (insufficient) heart valve is pressed against the vessel wall at the same time due to the self-expanding characteristic of the stent 100, as can be seen in particular in FIG. 7c. In more detail, the semi-lunar leaflets V of the native heart valve are clamped between the positioning arches 115 and the retaining arches 116 of the heart valve stent 100 because of the expansion of the stent 100, in addition to which the prosthetic heart valve 200 is optimally positioned and is stably anchored.

Exemplary embodiments of an operating handle 10-1 of a medical catheter delivery system in accordance with the present disclosure are described in the following with reference to FIGS. 8 to 23.

According to some embodiments of the present disclosure, the operating handle 10-1 comprises a hand grip 11 designed to be held by a user, and a manipulating part 12 axially aligned with the hand grip 11. Preferably, the manipulating part 12 of the operating handle 10-1 is rotatable relatively to the hand grip 11 about a longitudinal axis L defined by the operating handle 10-1.

In some embodiments of the present disclosure, the operating handle 10-1 comprises at least one sliding member 30, 40 operatively linked with the manipulating part 12 of the operating handle 10-1 by way of a cam mechanism 50 such that, upon rotation of the manipulating part 12 relative to the hand grip 11, the at least one sliding member 30, 40 moves axially in the direction of the longitudinal axis L.

Preferably, the cam mechanism 50 is integrated into the operating handle 10-1 and is configured for transforming a rotary motion of the manipulating part 12 relative to the hand grip 11 into a linear motion of the at least one sliding member 30, 40 relative to the hand grip 11.

In accordance with some embodiments of the present disclosure, the manipulating part 12 of the operating handle 10-1 is a rotating wheel designed to be gripped by a user with one of its hands, whereas the other hand holds the hand grip 11.

According to some embodiments of the operating handle 10-1 disclosed herein, the cam mechanism 50 comprises a cylindrical member 51 connected with the manipulating part 12 of the operating handle 10-1, wherein the cylindrical member 51 comprises at least one cam groove 31, 41. In accordance with some preferred embodiments of the present disclosure, the cam mechanism 50 further comprises at least one pin member 32, 42 having a first end portion connected with the at least one sliding member 30, 40, and a second end portion opposite to the first end portion, the second end portion of the at least one pin member 32, 42 engaging the at least one cam groove 31, 41 such that, upon rotation of the manipulating part 12 relative to the hand grip 11, the at least one pin member 32, 42 follows a cam profile defined by the at least one cam groove 31, 41.

Preferably, the hand grip 11 of the operating handle is formed as a jacket. Moreover, according to some embodiments of the present disclosure, the cylindrical member 51 of the cam mechanism 50 is at least partly disposed concentrically and coaxially with the hand grip 11, wherein the cylindrical member 51 of the cam mechanism 50 is rotatable relatively to the hand grip 11.

In accordance with some preferred embodiments of the present disclosure, the cylindrical member 51 of the cam mechanism 50 is at least partly hollow. Furthermore in some embodiments of the present disclosure the cam mechanism 50 of the operating handle 10-1 comprises a body member 52 disposed concentrically and coaxially with the hollow cylindrical member 51, wherein the body member 52 comprises a cylindrical portion 52a having a diameter less than an inner diameter of the hollow cylindrical member 51, the cylindrical portion 52a being at least partly received in the interior of the hollow cylindrical member 51 such that the hollow cylindrical member 51 is rotatable relatively to the body member 52. Preferably, the body member 52 is provided with at least one flange 53 for preventing axial movement of the manipulating part 12 relative to the body member 52.

Reference is made in the following in particular to FIGS. 8 to 23 for explaining an exemplary embodiment of an operating handle 10-1 of a medical catheter delivery system designed for retrograde (for example transarterial, transfemoral or transsubclavian) insertion of an expandable heart valve prosthesis 150.

In detail, FIG. 8 illustrates an exemplary embodiment of an operating handle 10-1 of a medical catheter delivery system for retrograde insertion of an expandable heart valve prosthesis. According to the exemplary embodiment depicted in FIG. 8, the operating handle 10-1 is provided at a proximal end portion of a catheter delivery system (not shown) and comprises a hand grip 11 designed to be held by a user. Moreover, the operating handle 10-1 comprises a manipulating part 12 axially aligned with the hand grip 11. The manipulating part 12 is rotatable relatively to the hand grip 11 about a longitudinal axis L defined by the operating handle 10-1.

Preferably, the manipulating part 12 is a rotating wheel designed to be gripped by a user with one of its hands, whereas the other hand holds the hand grip 11.

The operating handle 10-1 according to the exemplary embodiment depicted in FIGS. 8 to 23 further comprises at least one sliding member 30, 40 operatively linked with the manipulating part 12 of the operating handle 10-1. The at least one sliding member 30, 40 is operatively connected with a sleeve-shaped member 81, 82 of a catheter tip 80-1 (not shown in FIGS. 8 to 23) connected with the operating handle 10-1.

In the exemplary embodiment depicted in FIGS. 8 to 23, the operating handle 10-1 is provided with a total of two sliding members: a first sliding member 30 which is operatively linked with the manipulating part 12 of the operating handle 10-1 and operatively connected with a first sleeve-shaped member 81 of the catheter tip 80-1, and a second sliding member 40 which is operatively linked with the manipulating part 12 of the operating handle 10-1 and operatively connected with a second sleeve-shaped member 82 of the catheter tip 80-1.

FIGS. 17a, b illustrate exemplary embodiments of sliding members 30, 40 adapted to be utilized in the exemplary embodiment of the operating handle 10-1 in accordance with FIG. 8.

Referring to FIG. 17a, a first sliding member 30 preferably comprises a body having a first cylindrical portion 30' and a second cylindrical portion 30".

FIG. 16 illustrates how the sliding members 30, 40 are received within the operating handle 10-1. As can be seen from FIG. 16, the first cylindrical portion 30' of the first sliding member 30 is connected (with of a screw 2) with a proximal end portion of a first catheter tube 91 acting as force transmitting mechanism. The distal end portion of the first catheter tube 91 is preferably connected with a first sleeve-shaped member 81 of a catheter tip 80-1 (not shown in FIG. 16).

Figure 17B:
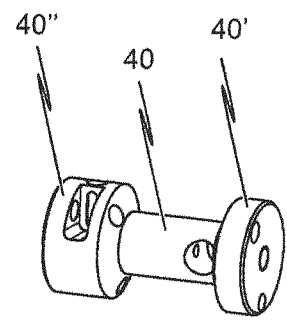

An exemplary embodiment of a second sliding member 40 of the operating handle 10-1 according to some embodiments of the present disclosure is shown in FIG. 17b. Accordingly, the second sliding member 40 may also comprise a body having a first cylindrical portion 40' and a second cylindrical portion 40". Referring to FIG. 16, the first cylindrical portion 40' of the second sliding member 40 is connected (with a screw 3) with a proximal end portion of a second catheter tube 92 acting as force transmitting mechanism. The distal end portion of the second catheter tube 92 is preferably connected with a second sleeve-shaped member 82 of a catheter tip 80-1 (not shown in FIG. 16).

Referring to FIG. 16, the first and second sliding members 30, 40 are respectively provided with a corresponding pin member 32, 42. Each of the two pin members 32, 42 has a first end portion connected with a corresponding one of the two sliding members 30, 40, and a second end portion opposite to the first end portion.

The first and second sliding members 30, 40 are operatively linked with the manipulating part 12 of the operating handle 10-1 by way of a cam mechanism 50. The cam mechanism 50 is adapted to transform a rotary motion of the manipulating part 12 of the operating handle 10-1 relative to the hand grip 11 into a linear motion of the first and/or second sliding member 30, 40 relative to the hand grip 11.

In more detail, in the exemplary embodiment of the operating handle 10-1 depicted in FIGS. 8 to 23, the cam mechanism 50 is integrated into the operating handle 10-1 and is configured for transforming a rotary motion into a linear motion.

In the exemplary embodiment illustrated in FIGS. 8 to 23, the cam mechanism 50 comprises a cylindrical member 51 and a body member 52. An exemplary embodiment of the cylindrical member 51 of the cam mechanism 50 is illustrated in FIGS. 13 and 14, whereas FIG. 15 shows an exemplary embodiment of a body member 52 of the cam mechanism 50.

Hence, according to the exemplary embodiment depicted in FIGS. 13 and 14, the cam mechanism 50 may comprise an at least partly hollow cylindrical member 51 connected with the manipulating part 12 of the operating handle 10-1. Preferably, the at least partly hollow cylindrical member 51 and the manipulating part 12 of the operating handle 10-1 are formed integrally, i.e., made from one piece. In an assembled state of the operating handle depicted in FIG. 8, the cylindrical member 51 of the cam mechanism 50 is at least partly disposed concentrically and coaxially with the (jacked-like) hand grip 11, wherein the cylindrical member 51 is rotatable relatively to the hand grip 11.

According to some embodiments disclosed herein, the cam mechanism 50 further comprises a body member 52 of the kind as shown in FIG. 15. As illustrated in FIG. 15, the body member 52 may be at least partly hollow such that the sliding members 30, 40 of the operating handle 10-1 are accommodatable within the body member 52 in a manner that the sliding members 30, 40 are axially movable relatively to the body member 52. The respective sliding members 30, 40 are preferably designed such as to be guided by an inner surface of the hollow body member 52.

In an assembled state of the operating handle 10-1 shown in FIG. 8, the body member 52 is disposed concentrically and coaxially with the hollow cylindrical member 51. In this regard, reference is also made to FIG. 10, which illustrates the exemplary embodiment of the operating handle 10-1 in accordance with FIG. 8 without hand grip wherein 11.

Reference is made to FIG. 15 which illustrates the body member 53 of the cam mechanism 50 utilized in the exemplary embodiment of the operating handle 10-1 in accordance with FIG. 8 in a perspective elevation. Accordingly, in the exemplary embodiment, the body member 52 comprises a cylindrical portion 52a having a diameter less than an inner diameter of the hollow cylindrical member 51.

Referring to FIGS. 11 and 12, in the assembled state of the operating handle 10-1, the cylindrical portion 52a of the body member 52 is at least partly received in the interior of the hollow cylindrical member 51 such that the hollow cylindrical member 51 is rotatable relatively to the body member 52.

As can be seen from FIG. 15, the body member 52 further comprises a portion 52b which is intended to be fixed to the hand grip 11 of the operating handle 10-1. In more detail, the portion 52b of the body member 52, which is fixed to the hand grip 11 in an assembled state of the operating handle 10-1, is cylindrical and has at least one portion having a diameter equal to or substantially equal to the outer diameter of the hollow cylindrical member 51. As can be seen from the representation of FIG. 8, the (jacket-like) hand grip 11 is at least partly disposed around the cylindrical portion 52b of the body member 52 such as to be concentrically and coaxially with the cylindrical portion 52b.

Referring to FIGS. 10 to 14, in the exemplary embodiment of the operating handle 10-1, the cylindrical member 51 comprises, for each sliding member 30, 40 of the operating handle 10-1, a corresponding cam groove 31, 41. As schematically illustrated in FIGS. 11 and 12, the second end portions of the corresponding pin members 32, 42 of the sliding members 30, 40 engage with a corresponding cam groove 31, 41 provided in the cylindrical member 51 of the cam mechanism 50. Upon rotation of the manipulating part 12 of the operating handle 10-1 relative to the hand grip 11, the respective pin members 32, 42 follow a cam profile defined by the corresponding cam groove 31, 41.

As can be seen in particular from FIG. 11, in the exemplary embodiment of the operating handle 10-1, the manipulating part 12 of the operating handle 10-1 may be formed as a rotating wheel rotating wheel having a diameter greater than the diameter of the cylindrical member 51 of the cam mechanism 50. On the other hand, the hand grip 11 of the operating handle 10-1 may be formed as a jacket (see FIGS. 10a and 10b), wherein the cylindrical member 51 of the cam mechanism 50 is at least partly disposed concentrically and coaxially with the hand grip 11 and wherein the cylindrical member 51 of the cam mechanism 50 is rotatable relatively to the hand grip 11.

In more detail, the cylindrical member 51 of the cam mechanism 50 is preferably at least partly hollow. The cam mechanism 50 preferably further comprises a body member 52 serving as an anchorage of the operating handle. As can be seen from FIG. 16, a proximal end section of a stent holder tube 93 is connected with the body member 52 of the operating handle, a distal end section of the stent holder tube being fixed to stent retaining element 85 of a catheter tip 80-1. In the assembled state of the operating handle 10-1, the body member 52 is disposed concentrically and coaxially with the hollow cylindrical member 51.

In order to prevent axial movement of the manipulating part 12 of the operating handle 10-1 relative to the body member 52, the operating handle 10-1 depicted in FIGS. 8 to 23 is provided with at least one flange 53. In this regard, reference is made to FIGS. 11 and 12. The at least one flange 53 is connected with the body member 52 and abuts a rear side 54 of the manipulating part 12. Moreover, the body member 52 is at least partly hollow, wherein the corresponding sliding members 30, 40 are received within the body member 52 such that the corresponding sliding members 30, 40 are axially movable relatively to the body member 52.

The operating handle 10-1 depicted in FIGS. 8 to 23 is adapted for manipulating a catheter tip 80-1 of a catheter delivery system. In more detail, the operating handle 10-1 is designed for manipulating at least one sleeve-shaped member 81, 82 of a catheter tip 80-1 having a seat portion for accommodating a tightly compressed heart valve prosthesis 150.

In order to secure functional reliability of the cam mechanism 50, the cam mechanism is provided with means for preventing a rotational movement of the sliding members 30, 40 relative to the body member 52.

In the exemplary embodiment depicted in FIGS. 8 to 23, the means for preventing a rotational movement of the sliding members 30, 40 relative to the body member 52 comprises at least one elongated hole 33, 43 allocated to the sliding members 30, 40. In more detail, in the exemplary embodiment, the body member 52 is provided with a total of two elongated holes 33, 43, each extending parallel to the longitudinal axis L of the operating handle 10-1. Through each of the two elongated holes 33, 43 one pin member 32, 42 connected with one of the two sliding members 30, 40 extends (see FIGS. 11 and 12).

The exemplary embodiment of the operating handle 10-1 depicted in FIGS. 8 to 23 is further provided with decoupling mechanism for selectively separating an operative linkage between at least one of the sliding members 30, 40 (preferably the second sliding member 40) and the manipulating part 12 of the operating handle 10-1.

An exemplary embodiment of the decoupling mechanism 20 is described in the following with reference to FIGS. 18a, b, FIG. 19 and FIGS. 20a to 20c. As will be described later, FIGS. 20a to 20c also show a blocking mechanism for blocking a rotation movement of the at least one sliding member 30, 40 relative to the body member 52 upon rotation of the manipulating part 12 of the operating handle 10-1 relative to the hand grip 11.

Figure 18B:
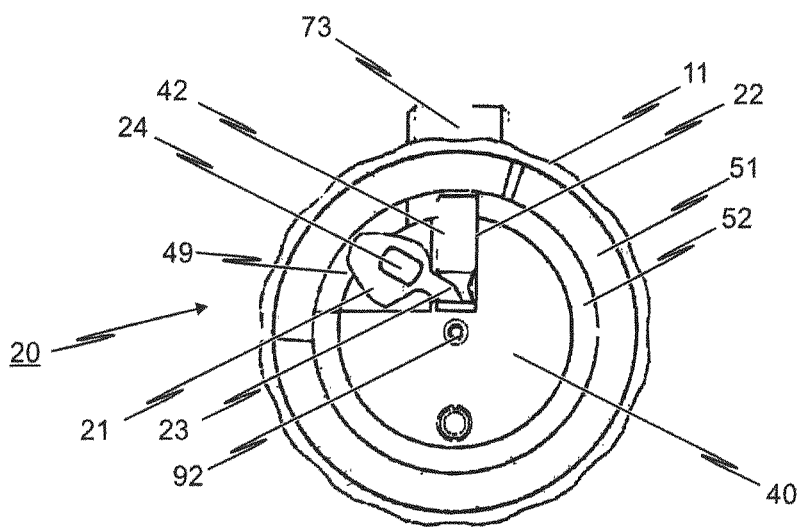

In more detail, FIGS. 18a and 18b illustrate a cross-sectional view of the operating handle in accordance with FIG. 8 for explaining an exemplary embodiment of decoupling mechanism for selectively separating an operative linkage between a sliding member 30, 40 of the cam mechanism 50 of the operating handle 10-1 and the manipulating part 12 of the operating handle 10-1.

FIG. 19 illustrates a rear side (closed) of the exemplary embodiment of the operating handle 10-1 in accordance with FIG. 8 in a perspective elevation, and FIGS. 20a to 20c illustrate the (open) rear side of the operating handle 10-1 in accordance with FIG. 19 for explaining a blocking mechanism for blocking a rotation movement of the at least one sliding member 30, 40 relative to the body member 52 upon rotation of the manipulating part 12 of the operating handle 10-1 relative to the hand grip 11.

Accordingly, the decoupling mechanism 20 comprises a pin member manipulating element 21 operatively connected with one of the two pin members 32, 42 of the cam mechanism 50. The pin member manipulating element 21 is drivable from a first position, in which the corresponding pin member 32, 42 engages with the corresponding cam groove 31, 41, into a second position, in which the corresponding pin member 32, 42 is disengaged from the corresponding cam groove 31, 41.

In the embodiment illustrated in FIGS. 18a and 18b, the decoupling mechanism 20 is adapted to interact with the second pin member 42 of the cam mechanism 50 which is connected with the second sliding member 40 (see FIG. 16) and which normally engages with the second cam groove 41 provided in the hollow cylindrical member 51 (see FIGS. 11 to 14) such that, upon rotation of the manipulating part 12 relative to the hand grip 11, the second pin member 42 follows the cam profile defined by the second cam groove 41.

From the illustrations in FIGS. 18a and 18b, the engagement between the second pin member 42 and the second cam groove 41 provided in the hollow cylindrical member 51 is recognizable. Accordingly, during normal operation depicted in FIG. 18a, the first end portion of the second pin member 42 is at least partly received in a recess 22 provided in the second sliding member 40 such that the second pin member 42 is movable relatively to the second sliding member 40 in a longitudinal direction defined by the recess 22, i.e. in a radial direction relative to the hollow cylindrical member 51.

The pin member manipulating element 21 comprises a lever arm 23 having a first end section operatively connected with the second pin member 42 and, in particular with the first end portion of the second pin member 42. The lever arm 23 of the pin member manipulating element 21 further has a second end section opposite to the first end section. The second end section of the lever arm 23 is operatively connected with an operating bar 24 for moving the lever arm 23 with the second pin member 42 connected thereon.

As illustrated in FIG. 16, the operating bar 24 of the decoupling mechanism 20 may be a rod-like element extending through the interior of the operating handle 10-1 and, in more detail, through the first and second sliding members 30, 40, received within the at least partly hollow body member 52, and also through the distal front side of the operating handle 12, such that the sliding members 30, 40 are movable relatively to the operating bar 24. At the distal front side of the operating handle 12 a manipulation knob 25 is provided for manipulating the operating bar 24 and thus the decoupling mechanism 20. The operating bar 24 preferably has a cross-section which allows a corresponding interaction with the second end section of the lever arm 23, for example, a rectangular cross-section. When turning the manipulation knob 25, the operating bar 24 is turned and the lever arm 23 is transferred from the position illustrated in FIG. 18a into the position illustrated in FIG. 18b.

In the exemplary embodiment depicted in FIGS. 18a and 18b, the second pin member 42 is movable by way of the operating bar 24 and the lever arm 23 operatively connected with the operating bar 24 from a coupled state, in which the second end portion of the pin member 42 engages with the corresponding cam groove 41 (see FIG. 18a), into an uncoupled state, in which the second end portion of the pin member 40 disengages the cam groove 41 and in which the pin member manipulating element 21 at least partly engages with a further recess 49 provided in the body member 52 of the cam mechanism 50 thereby blocking an axial movement of the sliding member 40 relative to the body member 52 upon rotation of the manipulating part 12 of the operating handle 10-1 relative to the hand grip 11.

As illustrated in FIGS. 20a to 20c, the operating bar 24 is further provided with a blocking member 26. When rotating the operating bar 24 for moving the second pin member 42 from its coupled state into its uncoupled state, the operating bar 24 also manipulates the blocking member 26. In more detail, the blocking member 26 moves a stop pin 27 radially outward such that the stop pin 27 abuts upon a body stop 28 provided at the cylindrical member 51 when the manipulating part 12 with the cylindrical member 51 is rotated relatively to the hand grip 11.

In the exemplary embodiment depicted FIGS. 20a to 20c, the body stop 28 is formed as a pin axially extending from disc member 29. The disc member 29, which is part of the manipulating part 12 of the operating handle 10-1, is disposed at the flange 53 such as to be pivotably around a center pin 13 on the longitudinal axis L of the operating handle 10-1.

As can be seen from FIG. 16 or FIGS. 20a to 20c, the disc member 29 is biased via two tension springs 14. A screw 4 connected with the manipulating part 12 such as to extend radially in the interior of the manipulating part interacts with the body stop 28 upon rotation of the manipulating part 12 relative to the hand grip 11. Accordingly, a continued rotation of the manipulating part 12 relative to the hand grip 11 is blocked as soon as the decoupling mechanism 20 is activated.

The spring mechanism constituted by the two tension springs 14 serves for resetting the manipulating part 12 when the manipulating part 12 is rotated relatively to the hand grip 11. In more detail, the two tension springs 14 are stretched as a tension load is applied by means of the screw 4 connected with the manipulating part 12, when the screw 4 abuts the body stop 28 (see FIG. 20b) and the manipulating part 12 is further rotated relatively to the hand grip 11 (see FIG. 20c). The two tension springs 14 are designed to operate with a tension load applied by the screw 4. After applying a tension load to the tension springs 14 by means of the screw 4, the stretched tension springs 14 reset the manipulating part 12 of the operating handle into a state depicted in FIG. 20b, i.e., into a state where the screw 4 begins touching the body stop 28.

When turning the manipulating part 12 of the operating handle 10-1 relatively to the hand grip 11, the sliding members 30, 40 received within the operating handle 10-1 are moved axially in the direction of the longitudinal direction L of the operating handle 10-1. At the same time, corresponding sleeve-shaped elements 81, 82 of a catheter tip 80-1 operatively connected by way of a catheter shaft 90 to the operating handle 10-1 are moved axially because these sleeve-shaped elements 81, 82 are operatively connected by way of force transmitting mechanism with the corresponding sliding members 30, 40 of the operating handle 10-1.

In some embodiment disclosed herein, the first sliding member 30 is operatively connected by way of a first catheter tube 91 with a first sleeve-shaped element 81 of the catheter tip 80-1, whereas the second sliding member 40 is operatively connected by way of a second catheter tube 92 with a second sleeve-shaped member 82 of the catheter tip 80-1. Accordingly, upon rotation of the manipulating part 12 of the operating handle 10-1 relative to the hand grip 11 of the operating handle 10-1, the first sliding member 30 together with the operatively connected first sleeve-shaped member 81 of the catheter tip 80-1 may be moved axially. Independent from this axial movement, the second sliding member 40 together with the operatively connected second sleeve-shaped member 82 of the catheter tip 80-1 may also be moved axially.

The longitudinal (axial) displacement stroke acting on the first sleeve-shaped member 81 of the catheter tip 80-1 when turning the manipulating part 12 of the operating handle 10-1 relative to the hand grip 11 is defined by the cam profile of the first cam groove 31 with which the first pin member 32 of the first sliding member 30 engages. In a similar way, the longitudinal (axial) displacement stroke acting on the second sleeve-shaped member 82 of the catheter tip 80-1 when turning the manipulating part 12 of the operating handle 10-1 relative to the hand grip 11 is defined by the cam profile of the second cam groove 41 with which the second pin member 42 of the second sliding member 40 engages.

Accordingly, by selecting corresponding cam profiles for the first and second cam grooves 31, 41 a predefinable sequence of axial movements of the first and second sleeve-shaped members 81, 82 of the catheter tip 80-1 is obtainable when turning the manipulating part 12 of the operating handle 10-1 relative to the hand grip 11.

In preferred embodiments of the operating handle 10-1 adapted for a catheter delivery system for retrograde heart valve implantation, the respective cam profiles of the first and second cam grooves 31, 41 are chosen such that the catheter tip 80-1 is manipulated as follows:

when turning the manipulating part 12 of the operating handle 10-1 relative to the hand grip 11 through a first angular range, the first sliding member 30 together with the first sleeve-shaped member 81 of the catheter tip 80-1 are moved axially relative to the operating handle 10-1 in the proximal direction, while the second sliding member 40 together with the second sleeve-shaped member 82 of the catheter tip 80-1 are not moved relatively to the operating handle 10-1;

when turning the manipulating part 12 of the operating handle 10-1 relative to the hand grip 11 through a second angular range following the first angular range, the second sliding member 40 together with the second sleeve-shaped member 82 of the catheter tip 80-1 are moved axially relatively to the operating handle 10-1 in the distal direction, while the first sliding member 30 together with the first sleeve-shaped member 81 of the catheter tip 80-1 are not moved relatively to the operating handle 10-1; and when turning the manipulating part 12 of the operating handle 10-1 relative to the hand grip 11 through a third angular range following the second angular range, the first sliding member 30 together with the first sleeve-shaped member 81 of the catheter tip 80-1 are again moved axially relatively to the operating handle 10-1 in the proximal direction, while the second sliding member 40 together with the second sleeve-shaped member 82 of the catheter tip 80-1 are not moved relatively to the operating handle 10-1.

Accordingly, the operating handle 10-1 allows for manipulating a catheter tip 80-1 operatively connected with the operating handle 10-1 such that the catheter tip 80-1 is transferred in a step-wise manner from its first functional state (see for example FIG. 6*a*) into its second functional state (see for example FIG. 6*b*) by turning the manipulating part 12 of the operating handle 10-1 relative to the hand grip 11 through a first angular range, and then from its second functional state (see for example FIG. 6*b*) into its third functional state (see for example FIG. 6*c*) by turning the manipulating part 12 of the operating handle 10-1 relative to the hand grip 11 through a second angular range following the first angular range, and then from its third functional state (see for example FIG. 6*c*) into its fourth functional state (see for example FIG. 6*d*) by turning the manipulating part 12 of the operating handle 10-1 relative to the hand grip 11 through a third angular range following the second angular range.

In accordance with some embodiments of the operating handle 10, the cam profiles of the first and second cam grooves 31, 41 are selected in a manner such that the longitudinal (axial) displacement stroke acting on the first sleeve-shaped member 81 of the catheter tip 80-1 when turning the manipulating part 12 of the operating handle 10-1 relative to the hand grip 11 through a first angular range is 20 mm to 34 mm in the proximal direction, preferably 24 mm to 30 mm in the proximal direction, and more preferably 26 mm to 28 mm in the proximal direction.

Moreover, the cam profiles of the first and second cam grooves 31, 41 are preferably selected in a manner such that the longitudinal (axial) displacement stroke acting on the second sleeve-shaped member 82 of the catheter tip 80-1 when turning the manipulating part 12 of the operating handle 10-1 relative to the hand grip 11 through a second angular range following the first angular range is 6 mm to 18 mm in the distal direction, preferably 9 mm to 15 mm in the distal direction, and more preferably 11 mm to 13 mm in the distal direction.

In addition, the cam profiles of the first and second cam grooves 31, 41 are preferably selected in a manner such that the longitudinal (axial) displacement stroke acting on the first sleeve-shaped member 81 of the catheter tip 80-1 when turning the manipulating part 12 of the operating handle 10-1 relative to the hand grip 11 through a third angular range following the second angular range is 6 mm to 18 mm in the proximal direction, preferably 9 mm to 15 mm in the proximal direction, and more preferably 11 mm to 13 mm in the proximal direction.

For subdividing a maximal available turning movement of the manipulating part 12 of the operating handle 10-1 when rotated relative to the hand grip 11 and for separating the respective angular ranges through which the manipulating part 12 is turnable relatively to the hand grip 11, the operating handle 10-1 according to some embodiments is provided with a corresponding locking mechanism 70.

In accordance with some embodiments, the locking mechanism 70 comprises at least one locking recess 71-1, 71-2 provided in the cylindrical member 51 of the cam mechanism 50. Furthermore, the locking mechanism 70 is provided with at least one engaging piece 72 operatively connected with the body member 52. The engaging piece 72 is adapted to releasably engage with the at least one locking recess 71-1, 71-2 thereby preventing continuous rotation of the cylindrical member 51 relative to the body member 52 of the operating handle 10.

FIG. 21 illustrates an exemplary embodiment of the locking mechanism 70 in a perspective elevation, whereas FIG. 22 illustrates the locking mechanism 70 in accordance with FIG. 21 in a side-sectional elevation.

According to some aspects of the present disclosure, the locking mechanism 70 comprises operating elements for disengaging the engaging piece 72, when the engaging piece 72 engages with the at least one locking recess 71-1, 71-2.

FIGS. 23a to 23c illustrate an exemplary embodiment of operating elements of the locking mechanism in accordance with FIG. 21.

In this embodiment, the engaging piece 72 is spring-loaded and the operating elements comprises a spring-loaded push-button 73 operatively connected with the engaging piece 72. The push-button 73 is designed to be pushed by the user for disengaging the engaging piece 72.

The operating elements further comprises a lever 74 connected with the push-button 73 for pressing the engaging piece 72 down when the push-button 73 is pushed down by the user. Furthermore, the operating elements comprises a driving piece 75 having a first end section coupled to the lever 74 by elements of a pin 76 such as to be pivotable in a plane perpendicular to the direction of pushing of the push-button 73, and further having a second end section for pressing the engaging piece 72 down when the push-button 73 is pushed down by the user.

The driving piece 75 is coupled to the lever 74 such that the driving piece 75 swings out relatively to the lever 74 when the push-button 73 is pushed down by the user and when the cylindrical member 51 of the operating handle 10-1 is simultaneously rotated relatively to the body member 52. The second end section of the driving piece 75 loses contact with the engaging piece 72 when the driving piece 75 swings out relatively to the lever 74.

The operating elements may further comprise centering elements 77 for returning the driving piece 75 when the push-button 73 is released. In preferred embodiments, the centering elements 76 may comprise at least one spring member.

A locking mechanism 70 of the kind as disclosed herein ensures a step-wise manipulation of a catheter tip 80-1. In more detail, the locking mechanism 70 prevents that the manipulating part 12 of the operating handle 10-1 can be rotated by the user relatively to the hand grip 11 through a maximal available angular turning range, when the push-button 73 is continuously pushed.

In the exemplary embodiment depicted in the FIG. 21, the locking mechanism 70 comprises a plurality of locking recesses 71-1, 71-2 provided in the cylindrical member 51 of the cam mechanism 50 such as to subdivide a maximal available turning movement of the manipulating part 12 into a plurality of consecutive indexing turning movements of the manipulating part 12.

In more detail, in the exemplary embodiment depicted in FIG. 21, the locking mechanism 70 comprises a first locking recess 71-1 provided in the cylindrical member 51 such that the pin members 32, 42 of the cam mechanism 50 are at the beginning of their corresponding cam groove 31, 41 when the engaging piece 72 of the locking mechanism 70 engages with the first locking recess 71-1.

Furthermore, the locking mechanism 70 comprises at least one second locking recess 71-2 provided in the cylindrical member 51 such that the pin members 32, 42 of the cam mechanism 50 are in a central portion of their corresponding cam groove 31, 41 when the engaging piece 72 of the locking mechanism 70 engages with the at least one second locking recess 71-2.

Moreover, the locking mechanism 70 comprises a third locking recess provided in the cylindrical member 51 such that the pin members 32, 42 of the cam mechanism are both at the end of their corresponding cam groove 31, 41 when the engaging piece 72 of the locking mechanism 70 engages with the third locking recess.

Reference is made in the following to FIG. 24 which illustrates an exemplary embodiment of a catheter tip 80-2 of a medical catheter delivery system for antegrade insertion of an expandable heart valve prosthesis in a part-sectional side elevation.

The catheter tip 80-2 depicted in FIG. 24 is provided with first and second sleeve-shaped members 81, 82 which define a seat portion of the catheter tip 80-2 for accommodating a heart valve prosthesis 150, for example a heart valve prosthesis of the kind as described with reference to FIG. 3.

The first sleeve-shaped member 81 of the catheter tip 80-2 is connected by way of a first catheter tube 91 with a first sliding member 30-2 of an operating handle 10-2 not illustrated in FIG. 24. The second sleeve-shaped member 82 is connected by way of a second catheter tube 92 with a second sliding member 40-2 of the operating handle 10-2. The second catheter tube 92 is disposed within a lumen defined by the first catheter tube 91.

Moreover, stent retaining element 85 comprising a crown having attachment elements 86 for releasably connecting with at least one catheter retaining elements 123 of a heart valve prosthesis 150 are provided. The stent retaining element 85 are connected with an anchorage 45 of the operating handle 10-2 by way of a stent holder tube 93.

In the catheter tip 80-2 depicted in FIG. 24 which is designed for an antegrade access, the first sleeve-shaped element 81 of the catheter tip 80-2 is in form of a stent funnel, whose opening points in the direction of the distal end of the catheter tip 80-2. The retaining arches 116 of a heart valve stent 100 can be mounted in the interior of the first sleeve-shaped member 81. The first sleeve-shaped member 81 in the form of the stent funnel can be telescopically accommodated by the second sleeve-shaped member 82 which is preferably in the form of a stent sheath, when the catheter tip 80-2 is in a closed state (see FIG. 24). In this way, positioning arches 115 of a heart valve stent 100 accommodated in the catheter tip 80-2 are located between the outer circumferential surface of the stent funnel and the inner circumferential surface of the stent sheath when the heart valve stent 150 is mounted in the catheter tip 80-2.

In relation to the operating handle 10-2 of the antegrade insertion system, it is provided that this has a first sliding member 30 associated with a first sleeve-shaped member 81 of the catheter tip 80-2 and a second sliding member 40 associated with a second sleeve-shaped member 82 of the catheter tip 80-2. The first sliding member 30 cooperates with the first sleeve-shaped member 81 of the catheter tip 80-2 so that, on actuation of the first sliding member 30, a previously definable longitudinal displacement of the first sleeve-shaped member 81 can be effected relative to the stent holder. In addition, the second sliding member of the operating handle cooperates with the second sleeve-shaped member of the catheter tip 80-2 so that, on actuation of the second sliding member, a previously definable longitudinal displacement of the second sleeve-shaped member of the catheter tip 80-2 can be effected relative to the stent retaining element 85 (stent holder) of the catheter tip 80-2.

A procedure for implanting a heart valve stent carried out antegradely is described in more detail in the following with reference to FIGS. 25a to 25d.

In detail, FIGS. 25a to 25d illustrate schematically an exemplary embodiment of a catheter tip 80-2 of a medical catheter delivery system for antegrade insertion of an expandable heart valve prosthesis 200 in different functional states for explaining a releasing procedure of a heart valve stent 100 accommodated in the catheter tip 80-2 of the catheter delivery system.

The distal end region of the catheter delivery system with a corresponding catheter tip 80-2 is shown in detail in the representation in FIG. 25a, whereby the catheter tip 80-2 is in its first functional state. An expandable heart valve stent is housed in the catheter tip 80-2.

In the representation of FIG. 25a, the catheter tip 80-2 is in its first functional state, in which catheter retaining elements 123 of the heart valve stent 100 are in engagement with stent retaining element 85 (stent holder) of the catheter tip 80-2, while retaining arches 116 of the heart valve stent 100 are housed in the first sleeve-shaped member 81 (stent funnel) of the catheter tip 80-2.

Positioning arches 115 of the heart valve stent 100 in the first functional state of the catheter tip 80-2 are between the second sleeve-shaped member of the catheter tip 80-2 and the first sleeve-shaped member 81 of the catheter tip 80-2, whereby the two sleeve-shaped members 81, 82 are arranged to overlap telescopically. In particular, the second sleeve-shaped member 82 of the catheter tip 80-2 covers the following components: the catheter retaining arches 116 of the heart valve stent 100, the positioning arches 115 of the heart valve stent 100, and the first sleeve-shaped member 81 of the catheter tip 80-2.

The inflow region of the heart valve stent 100 remote from the catheter retaining element 85 of the stent 100 is housed in the first sleeve-shaped member 81 of the catheter tip 80-2. The catheter tip 80-2, in the state shown in FIG. 25a, is advanced to the native heart valve antegradely, e.g. by approaching from the apex of the heart.

When the catheter tip 80-2 with the heart valve stent 100 accommodated in the catheter tip 80-2 has been advanced to the desired implantation location, the second sleeve-shaped member 82 of the catheter tip 80-2 is moved in the distal direction by manipulating the second sliding member 40 of the operating handle 10-2. As a consequence, the positioning arches 115 of the heart valve stent 100 are released, following a suitable stepwise release of the heart valve stent 100 from the catheter delivery system. This is achieved by transferring the catheter tip 80-2 from its first functional state to its second functional state by moving the second sleeve-shaped member 82 of the catheter tip 80-2 relatively to the stent retaining element 85 (stent holder) in the distal direction, and thus away from the operating handle 10-2, by manipulating the second sliding member 40 of the operating handle 10-2.

The longitudinal displacement stroke of the second sleeve-shaped member 82 of the catheter tip 80-2 that is effected relative to the stent holder has a result that the positioning arches 115 of the heart valve stent 100 are not longer surrounded and held by the second sleeve-shaped member 82 of the catheter tip 80-2. As a consequence of the self-expanding characteristic of the positioning arches 115 of the stent 100, these are opened because of the radial forces acting on them in a radial direction. The opened positioning arches 115 are then positioned in the pockets T of the native heart valve.

The catheter tip 80-2 can turn together with the catheter delivery system about the longitudinal axis L of the catheter tip 80-2, facilitating the positioning of the unfolded positioning arches 115 of the stent 100 in the pockets T of the native heart valve.

Figure 25C:
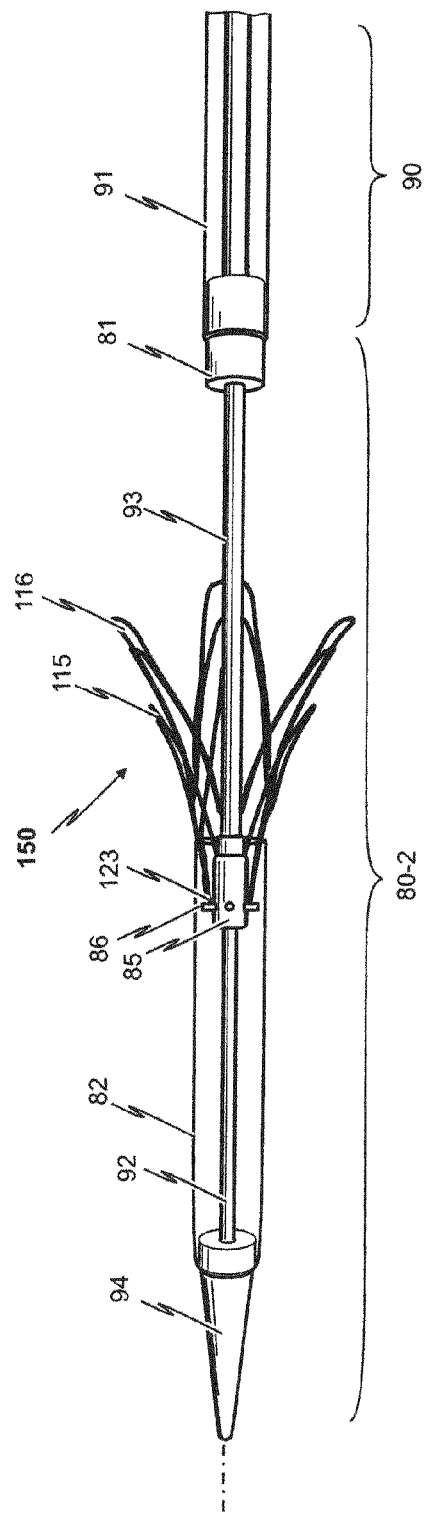

After positioning of the partially expanded heart valve stent 100 in the pockets T of the native heart valve, the catheter tip 80-2 is transferred from its second functional state in accordance with FIG. 25b into its third functional state in accordance with FIG. 25c.

In more detail, the first sleeve-shaped member 81 of the catheter tip 80-2 is moved relatively to the stent retaining element 85 (stent holder) in the proximal direction by manipulating the first sliding member 30 of the operating handle 10-2. Then, the retaining arches 116 of the heart valve stent 100 are released. Due to the radial forces acted on them in the radial direction, a prosthetic heart valve 200 attached to the retaining arches 116 of the stent 100 unfolds like an umbrella.

The function of the already unfolded prosthetic heart valve 200 can then be checked in the state depicted in FIG. 25c. After the functioning of the prosthetic heart valve has been demonstrated, the catheter tip 80-2 can then be transferred, by further manipulating of the second sliding member of the operating handle 10-2, from its third functional state (see FIG. 25c) into its fourth functional state (see FIG. 25d).

In more detail, by manipulating the second sliding member 40 of the operating handle 10-2, the second sleeve-shaped member 82 of the catheter tip 80-2 is moved in the distal direction, and thus away from the operating handle 10-2. As a consequence, the second sleeve-shaped member 82 of the catheter tip 80-2 no longer covers the stent retaining element 85 (stent holder) of the catheter tip 80-2. Thus, the (outflow) region of the stent 100 facing the catheter end tip 94 of the catheter tip 80-2 is released from the catheter tip 80-2, so that the outflow region of the stent 100 also expands, consequently leading to a complete unfolding of the heart valve stent 100.

In contrast, if it is found that the implanted prosthetic heart valve 200 cannot or can only adequately fulfill its function during the check of function of the already unfolded prosthetic heart valve 200 in the third functional state of the catheter tip 80-2, in accordance with FIG. 25c, or if the heart valve stent 100 is not optimally positioned or cannot be optimally positioned in the implantation side, there is the possibility of retracting the catheter tip 80-2 back into the second and then into the first functional state, by moving the corresponding sleeve-shaped members 81, 82 of the catheter tip 80-2 in the appropriate opposite direction. This allows the already released and expanded components of the heart valve stent 100 to be retracted back again into the respective sleeve-shaped members 81, 82 of the catheter tip 80-2, so that the stent 100 housed in the catheter tip 80-2 can be removed from the body of the patient.

Figure 25D:
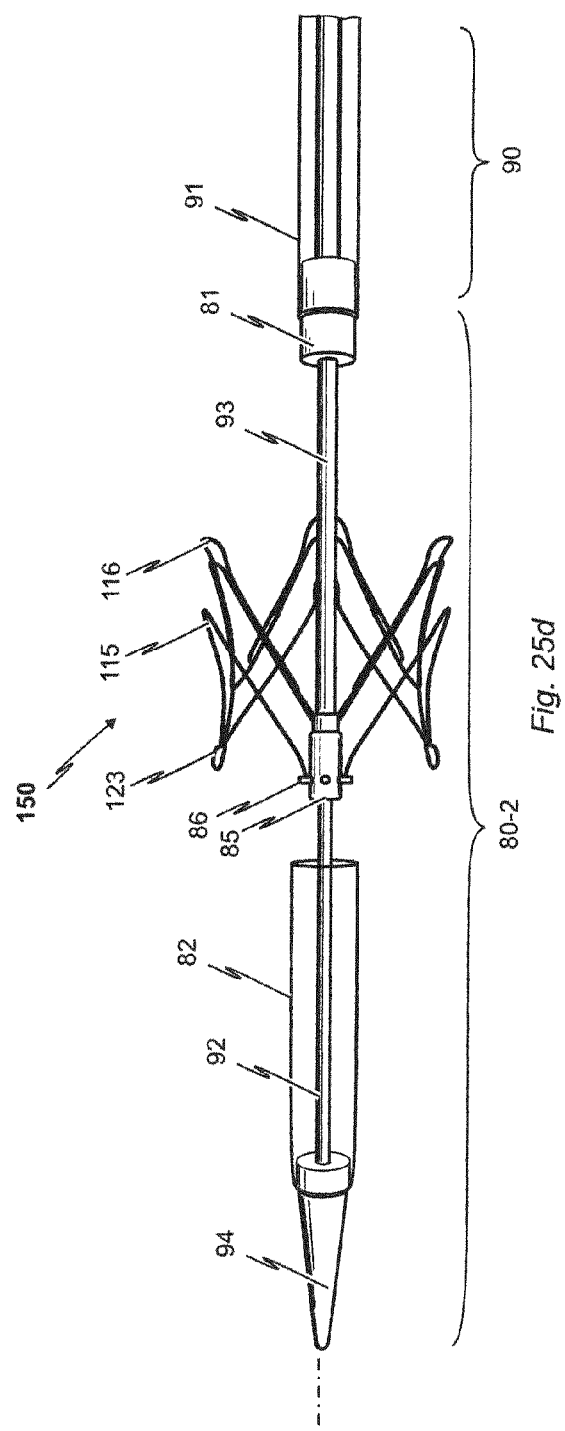

As shown in FIG. 25d, the retaining arches 116 of the heart valve stent 100 open in their radial direction on implantation of the heart valve stent 100, whereby the radial forces acting on the retaining arches 116 and also on the inflow region of the heart valve stent 100 result in the stent being pressed against the vessel wall, on the one hand ensuring that the heart valve stent 100 with a prosthetic heart valve 200 attached thereto is securely anchored at the implantation side and, on the other hand, that the heart valve stent 100 is reliably sealed in the inflow region of the stent 100.

An exemplary embodiment of an operating handle 10-2 of a medical catheter delivery system for antegrade insertion of an expandable heart valve prosthesis 150 is shown in FIGS. 26 to 29. From a structural and functional point of view, the operating handle 10-2 of the antegrade catheter delivery system mostly corresponds to the operating handle 10-1 of the transfemoral catheter delivery system previously described with reference to FIGS. 8 to 23; however, the shape of the two cam grooves 32, 42 is now different.

As shown in FIG. 26, the operating handle 10-2 for antegrade insertion comprises a hand grip 11 designed to be held by a user, and a manipulating part 12 axially aligned with the hand grip 11. The manipulating part 12 of the operating handle 10-2 is rotatable relatively to the hand grip 11 about a longitudinal axis L defined by the operating handle 10-2. In more detail, in the embodiment depicted in FIGS. 26 to 29, the manipulating part 12 of the operating handle 10-2 is a rotating wheel designed to be gripped by a user with one of its hands, whereas the other hand holds the hand grip 11.

As illustrated schematically in FIGS. 28 and 29, the operating handle 10-2 further comprises a first and second sliding member 30, 40 of the kind as already described with reference to FIGS. 17a and 17b. The first and second sliding members 30, 40 are operatively linked with the manipulating part 12 of the operating handle 10-2 with a cam mechanism 50 such that, upon rotation of the manipulating part 12 relative to the hand grip 11, the at least one sliding member 30, 40 moves axially in the direction of the longitudinal axis L.

Referring to FIGS. 28 and 29, the first sliding member 30 is operatively connected with a proximal end section of a first catheter tube 91, said first catheter tube 91 also having a opposite distal end section operatively connected with a first sleeve-shaped member 81 of a catheter-tip 80-2 such that manipulation of the first sliding member 30 of the operating handle 10-2 results directly in a corresponding manipulation of the first sleeve-shaped member 81 of the catheter tip 80-2. Also, the second sliding member 40 is operatively connected with a proximal end section of a second catheter tube 92. The second catheter tube 92 has a distal end section opposite to the proximal end section, said distal end section of the second catheter tube 92 being operatively connected with a second sleeve-shaped member 82 of a catheter-tip 80-2 such that manipulation of the second sliding member 40 of the operating handle 10-2 results directly in a corresponding manipulation of the second sleeve-shaped member 82 of the catheter tip 80-2.

Preferably, the cam mechanism 50 is integrated into the operating handle 10-2 and transforms a rotary motion of the manipulating part 12 relative to the hand grip 11 into a linear motion of the at least one sliding member 30, 40 relative to the hand grip 11.

As illustrated in FIG. 27, the cam mechanism 50 of the operating handle 10-2 for antegrade insertion comprises an at least partly hollow cylindrical member 51 connected with the manipulating part 12 of the operating handle 10-2. The at least partly hollow cylindrical member 51 is provided with a first cam groove 31 allocated to the first sliding member 30 and with a second cam groove 41 allocated to the second sliding member 40.

As illustrated schematically in FIGS. 28 and 29, the cam mechanism 50 of the operating handle 10-2 for antegrade insertion further comprises two pin members 32, 42, each of them having a first end portion connected with a corresponding one of the two sliding members 30, 40. Each of the two pin members 32, 42 have also a second end portion opposite to the corresponding first end portion. The second end portion of each of the two pin members 32, 42 engages with a corresponding one of the two cam grooves 31, 41 such that, upon rotation of the manipulating part 12 relative to the hand grip 11, the pin member 32, 42 follows a cam profile defined by the corresponding am groove 31, 41.

Preferably, the hand grip 11 of the operating handle 10-2 for antegrade insertion is formed as a jacket (see FIGS. 9a and 9b). Also, the cylindrical member 51 of the cam mechanism 50 is at least partly disposed concentrically and coaxially with the hand grip 11, wherein the cylindrical member 51 of the cam mechanism 50 is rotatable relatively to the hand grip 11.

As schematically illustrated in FIGS. 28 and 29, the cylindrical member 51 of the cam mechanism 50 is at least partly hollow. Furthermore, the cam mechanism 50 of the operating handle 10-2 comprises a body member 52 disposed concentrically and coaxially with the hollow cylindrical member 51.

When turning the manipulating part 12 of the operating handle 10-2 relatively to the hand grip 11, the sliding members 30, 40 received within the operating handle 10-2 are moved axially in the direction of the longitudinal direction L of the operating handle 10-2. At the same time, corresponding sleeve-shaped elements 81, 82 of a catheter tip 80-2 operatively connected by way of a catheter shaft 90 to the operating handle 10-2 are moved axially because these sleeve-shaped elements 81, 82 are operatively connected by way of force transmitting member with the corresponding sliding members 30, 40 of the operating handle 10-2.

In some embodiment of the antegrade catheter delivery system as disclosed herein, the first sliding member 30 of the operating handle 10-2 is operatively connected with a first catheter tube 91 to a first sleeve-shaped element 81 of the catheter tip 80-2, whereas the second sliding member 40 is operatively connected by means of a second catheter tube 92 with a second sleeve-shaped member 82 of the catheter tip 80-2. Accordingly, upon rotation of the manipulating part 12 of the operating handle 10-2 relative to the hand grip 11 of the operating handle 10-2, the first sliding member 30 together with the operatively connected first sleeve-shaped member 81 of the catheter tip 80-2 may be moved axially. Independent from this axial movement, the second sliding member 40 together with the operatively connected second sleeve-shaped member 82 of the catheter tip 80-2 may also be moved axially.

The longitudinal (axial) displacement stroke acting on the first sleeve-shaped member 81 of the catheter tip 80-2 when turning the manipulating part 12 of the operating handle 10-2 relative to the hand grip 11 is defined by the cam profile of the first cam groove 31 with which the first pin member 32 of the first sliding member 30 engages. In a similar way, the longitudinal (axial) displacement stroke acting on the second sleeve-shaped member 82 of the catheter tip 80-2 when turning the manipulating part 12 of the operating handle 10-2 relative to the hand grip 11 is defined by the cam profile of the second cam groove 41 with which the second pin member 42 of the second sliding member 40 engages.

Accordingly, by selecting corresponding cam profiles for the first and second cam grooves 31, 41 a predefinable sequence of axial movements of the first and second sleeve-shaped members 81, 82 of the catheter tip 80-2 is obtainable when turning the manipulating part 12 of the operating handle 10-2 relative to the hand grip 11.

In preferred embodiments of the operating handle 10-2 adapted for a catheter delivery system for antegrade heart valve implantation, the respective cam profiles of the first and second cam grooves 31, 41 are chosen such that the catheter tip 80-2 is manipulated as follows:

when turning the manipulating part 12 of the operating handle 10-2 relative to the hand grip 11 through a first angular range, the second sliding member 40 together with the second sleeve-shaped member 82 of the catheter tip 80-2 are moved axially relative to the operating handle 10-2 in the distal direction, while the first sliding member 30 together with the first sleeve-shaped member 81 of the catheter tip 80-2 are not moved relatively to the operating handle 10-2;

when turning the manipulating part 12 of the operating handle 10-2 relative to the hand grip 11 through a second angular range following the first angular range, the first sliding member 30 together with the first sleeve-shaped member 81 of the catheter tip 80-2 are moved axially relatively to the operating handle 10-2 in the proximal direction, while the second sliding member 40 together with the second sleeve-shaped member 82 of the catheter tip 80-2 are not moved relatively to the operating handle 10-2; and when turning the manipulating part 12 of the operating handle 10-2 relative to the hand grip 11 through a third angular range following the second angular range, the second sliding member 40 together with the second sleeve-shaped member 82 of the catheter tip 80-2 are again moved axially relatively to the operating handle 10-2 in the distal direction, while the first sliding member 30 together with the first sleeve-shaped member 81 of the catheter tip 80-2 are not moved relatively to the operating handle 10-2.

Accordingly, the operating handle 10-2 for antegrade insertion allows for manipulating a catheter tip 80-2 operatively connected with the operating handle 10-2 such that the catheter tip 80-2 is transferred in a step-wise manner from its first functional state (see for example FIG. 25*a*) into its second functional state (see for example FIG. 25*b*) by turning the manipulating part 12 of the operating handle 10-2 relative to the hand grip 11 through a first angular range, and then from its second functional state (see for example FIG. 25*b*) into its third functional state (see for example FIG. 25*c*) by turning the manipulating part 12 of the operating handle 10-2 relative to the hand grip 11 through a second angular range following the first angular range, and then from its third functional state (see for example FIG. 25*c*) into its fourth functional state (see for example FIG. 25*d*) by turning the manipulating part 12 of the operating handle 10-2 relative to the hand grip 11 through a third angular range following the second angular range.

In accordance with some embodiments of the operating handle 10-2, the cam profiles of the first and second cam grooves 31, 41 are selected in a manner such that the longitudinal (axial) displacement stroke acting on the second sleeve-shaped member 82 of the catheter tip 80-2 when turning the manipulating part 12 of the operating handle 10-2 relative to the hand grip 11 through a first angular range is 20 mm to 34 mm in the distal direction, preferably 24 mm to 30 mm in the distal direction, and more preferably 26 mm to 28 mm in the distal direction.

Moreover, the cam profiles of the first and second cam grooves 31, 41 are preferably selected in a manner such that the longitudinal (axial) displacement stroke acting on the first sleeve-shaped member 81 of the catheter tip 80-2 when turning the manipulating part 12 of the operating handle 10-2 relative to the hand grip 11 through a second angular range following the first angular range is 6 mm to 18 mm in the proximal direction, preferably 9 mm to 15 mm in the proximal direction, and more preferably 11 mm to 13 mm in the proximal direction.

In addition, the cam profiles of the first and second cam grooves 31, 41 are preferably selected in a manner such that the longitudinal (axial) displacement stroke acting on the second sleeve-shaped member 82 of the catheter tip 80-2 when turning the manipulating part 12 of the operating handle 10-2 relative to the hand grip 11 through a third angular range following the second angular range is 6 mm to 18 mm in the distal direction, preferably 9 mm to 15 mm in the distal direction, and more preferably 11 mm to 13 mm in the distal direction.

For subdividing a maximal available turning movement of the manipulating part 12 of the operating handle 10-2 when rotated relative to the hand grip 11 and for separating the respective angular ranges through which the manipulating part 12 is turnable relatively to the hand grip 11, the operating handle 10-2 for antegrade insertion is preferably also provided with a corresponding locking mechanism 70 of a kind as previously described with reference to FIGS. 21 to 23.

Also, the operating handle 10-2 for antegrade insertion is preferably also provided with a corresponding decoupling mechanism 20 of a kind as previously described with reference to FIGS. 19 and 20.

In accordance with some embodiments of catheter delivery systems for antegrade or retrograde insertion of heart valve prostheses, the catheter shaft 90 connecting the operating handle 10-1, 10-2 with the catheter tip 80-1, 80-2 is constituted by a plurality of catheter tubes 91, 92, 93 which are at least partly telescopically disposed. At least some of the plurality of catheter tubes 91, 92, 93 of the catheter shaft 90 is preferably made from flexible, sterilizable materials. These materials may include, for example, polyurethane, silicone, polyvinyl chloride (PVC), nylon, polyimide, PEEK, PET and/or polyether block amide, e.g. Pebax®. In some preferred embodiments, at least one inner catheter tube 92, 93 of the catheter shaft 90 is made from nitinol or stainless steel or a rigid plastic material.

Furthermore, the catheter tubes 91, 92, 93 are preferably least partly made of a braided wire construction. In this regard, the catheter shaft 90 constituted by the catheter tubes 91, 92, 93 is adapted to transfer compression and tension forces from the operating handle 10-1, 10-2 and, in particular, from a corresponding operating mechanisms of the operating handle 10-1, 10-2 (sliding members 30, 40) to the catheter tip 80-1, 80-2 without overly changing its total length.

In some embodiments of catheter delivery systems for antegrade or retrograde insertion of heart valve prostheses, the catheter shaft 90 is constituted by a plurality of catheter tubes 91, 92, 93 which are at least partly telescopically disposed, wherein the most outer catheter tube (first catheter tube 91) has at least partly a cross-sectional diameter which corresponds to the cross-sectional diameter of the catheter tip 80-1, 80-2 and, in particular, the cross-sectional diameter of a proximal sleeve-shaped member (first sleeve-shaped member 81) of the catheter tip 80-1, 80-2, thereby avoiding any gap or step between the catheter shaft 90 and the catheter tip 80-1, 80-2.

In preferred embodiments, the medical device for the treatment of a heart valve defect comprises a catheter delivery system adapted for antegrade or retrograde introducing a heart valve prosthesis 150 into the body of a patient, wherein the heart valve prosthesis comprises a heart valve stent 100 as disclosed, for example, in document WO 2010/086460 A1 (Int. Appl. No.: PCT/EP2010/052429) which is incorporated herein by reference. Moreover, the heart valve prosthesis 150 preferably comprises a prosthetic hear valve 200 as disclosed, for example, in document WO 2011/147849 A1 (International Appl. No.: PCT/EP2011/058506) which is also incorporated herein by reference.

In accordance with some embodiments disclosed, the operating handle 10-1, 10-2 is provided with a cam mechanism 50 comprising a cylindrical member 51 having at least one cam groove 31, 41. The cylindrical member 51 is connected with the manipulating part 12 the operating handle 10-1, 10-2 such as to be rotatable relatively to the hand grip 11 of the operating handle 10-1, 10-2 and also relatively to a body member 52 connected with the hand grip 11. At least one sliding member 30, 40 is received within the body member 52 such that the at least one sliding member 30, 40 is axially movable relatively to the body member 52. The cam mechanism 50 further comprises at least one pin member 32, 42 having a first end portion connected with the at least one sliding member 30, 40, and further having a second end portion opposite to the first end portion, the second end portion of the at least one pin member 32, 42 engaging with the at least one cam groove 31, 41 such that, upon rotation of the manipulating part 12 relative to the hand grip 11, the at least one pin member 32, 42 follows a cam profile defined by the at least one cam groove 31, 41.

The cam profile defined by the at least one cam groove 31, 41 is chosen such that a displacement diagram characterizing the cam mechanism 50 of the operating handle 10-1, 10-2 provides a step-wise changing of an axial position of the at least one sliding member 30, 40 as the manipulating part 12 of the manipulating handle 10-1, 10-2 together with the cylindrical member 51 therewith rotates relatively to the hand grip 11 of the operating handle 10-1, 10-2 about a longitudinal axis L defined by the operating handle 10-1, 10-2.

Preferably, the operating handle 10-1, 10-2 is also provided with a locking mechanism 70 for subdividing a maximal available turning movement of the manipulating part 12 when rotated relatively to the hand grip 11. The locking mechanism 70 comprises a plurality of locking recesses 71-1, 71-2 provided in the cylindrical member 51 of the cam mechanism 50 such as to a subdivide the maximal available turning movement of the manipulating part 12 into a plurality of consecutive indexing turning movements of the manipulating part 12.

The cam profile defined by the at least one cam groove 31, 41 is preferably chosen in accordance with the plurality of consecutive indexing turning movements of the manipulating part 12 defined by the locking mechanism 70 in such a manner that each of the consecutive indexing turning movements of the manipulating part 12 defined by the locking mechanism 70 corresponds to a step-wise changing of an axial position of the at least one sliding member 30, 40 as the manipulating part 12 of the manipulating handle 10-1, 10-2 together with the cylindrical member 51 therewith rotates relatively to the hand grip 11 of the operating handle 10-1, 10-2.

In preferred embodiments of the operating handle 10-1, 10-2, the locking mechanism 70 comprises at an engaging piece 72 operatively connected with the body member 52 of the cam mechanism, the engaging piece 72 being adapted to releasably engage with the a locking recess 71-1, 71-2 provided in the cylindrical member 51 of the cam mechanism 50 thereby preventing continuous rotation of the cylindrical member 51 relative to the body member 52.

According to a preferred embodiment of the operating handle 10-1, 10-2, the locking mechanism 70 comprises a first locking recess 71-1 provided in the cylindrical member 51 such that the at least one pin member 32, 42 of the cam mechanism 50 is at the beginning of the at least one cam groove 31, 41 when the engaging piece 72 of the locking mechanism 70 engages with the first locking recess 71-1.

Furthermore, the locking mechanism 70 comprises a second locking recess 71-2 provided in the cylindrical member 51 such that the at least one pin member 32, 42 of the cam mechanism 50 is in a first central portion of the at least one cam groove 31, 41 when the engaging piece 72 of the locking mechanism 70 engages with the second locking recess 71-2. A transfer of the at least one pin member 32, 42 from the beginning of the at least one cam groove 31, 41 to the first central portion of the at least one cam groove 31, 41 results in a previously defined first axial displacement stroke acting on the at least one pin member 32, 42. This previously defined first axial displacement stroke acting on the at least one pin member 32, 42 may initiate a first step when releasing a heart valve stent or a heart valve prosthesis accommodated in a catheter tip 10-1, 10-2 (see FIG. 7a or FIG. 25b).

Moreover, the locking mechanism 70 preferably comprises a further second locking recess provided in the cylindrical member 51 such that the at least one pin member 32, 42 of the cam mechanism 50 is in a second central portion of the at least one cam groove 31, 41 when the engaging piece 72 of the locking mechanism 70 engages with the further second locking recess 71-2. When transferring the at least one pin member 32, 42 from the first central portion of the at least one cam groove 31, 41 to the second central portion of the at least one cam groove 31, 41, the at least one pin member 32, 42 is axially moved with a previously defined second axial displacement stroke acting on the at least one pin member 32, 42. This previously defined second axial displacement stroke acting on the at least one pin member 32, 42 may initiate a second step when releasing a heart valve stent or a heart valve prosthesis accommodated in a catheter tip 10-1, 10-2 (see FIG. 7b or FIG. 25c).

In the preferred embodiment of the operating handle 10-1, 10-2, the locking mechanism 70 preferably comprises a third locking recess provided in the cylindrical member 51 such that the at least one pin member 32, 42 of the cam mechanism 50 is at the end of the at least one cam groove 31, 41 when the engaging piece 72 of the locking mechanism 70 engages with the third locking recess. When transferring the at least one pin member 32, 42 from the second central portion of the at least one cam groove 31, 41 to the end of the at least one cam groove 31, 41, the at least one pin member 32, 42 is axially moved with a previously defined third axial displacement stroke acting on the at least one pin member 32, 42. This previously defined third axial displacement stroke acting on the at least one pin member 32, 42 may initiate a third step when releasing a heart valve stent or a heart valve prosthesis accommodated in a catheter tip 10-1, 10-2 (see FIG. 7c or FIG. 25d).

The solution in accordance with the disclosure is not limited to the embodiments described in the attached drawings. It is contemplated that combinations of the individual features described in detail are also possible.

The invention claimed is:
1. Operating handle for manipulating a catheter tip of a catheter delivery system, the operating handle comprising:
 a hand grip designed to be held by a user; and
 a manipulating part axially aligned with the hand grip, wherein the manipulating part is rotatable relative to the hand grip about a longitudinal axis defined by the operating handle; and
 a first sliding member and a second sliding member, each being operatively coupled to the manipulating part via a cam mechanism that comprises:

a cylindrical member connected with the manipulating part, the cylindrical member comprising a first cam groove and a second cam groove;

a first pin member having a first end portion connected with the first sliding member, and a second end portion opposite to the first end portion, the second end portion of the first pin member engaging the first cam groove such that, upon rotation of the manipulating part relative to the hand grip, the first pin member follows a cam profile defined by the first cam groove;

a second pin member having a first end portion connected with the second sliding member, and a second end portion opposite to the first end portion, the second end portion of the second pin member engaging the second cam groove such that, upon rotation of the manipulating part relative to the hand grip, the second pin member follows a cam profile defined by the second cam groove;

wherein upon rotation of the manipulating part relative to the hand grip independently from each other, the first and second sliding members are axially moved along the longitudinal axis.

2. The handle according to claim 1, wherein the cam mechanism is integrated into the handle and is configured to transform rotation of the manipulating part relative to the hand grip into a linear motion of at least one of the first sliding member or the second sliding member relative to the hand grip.

3. The handle according to claim 1, wherein the manipulating part comprises a rotating wheel designed to be gripped by a first hand of a user while a second hand of the user holds the hand grip.

4. The handle according to claim 3, wherein the rotating wheel has a diameter greater than the diameter of the cylindrical member of the cam mechanism.

5. The handle according to claim 1,
wherein the hand grip is formed as a jacket,
wherein the cylindrical member of the cam mechanism is at least partly disposed concentrically and coaxially with the hand grip, and
wherein the cylindrical member of the cam mechanism is rotatable relative to the hand grip.

6. The handle according to claim 1, wherein the cylindrical member of the cam mechanism is at least partly hollow and comprises a body member disposed concentrically and coaxially with the hollow cylindrical member, wherein the body member comprises a cylindrical portion having a diameter less than an inner diameter of the hollow cylindrical member, the cylindrical portion being at least partly received in the interior of the hollow cylindrical member such that the hollow cylindrical member is rotatable relative to the body member.

7. The handle according to claim 6, wherein the body member is provided with at least one flange for preventing axial movement of the manipulating part relative to the body member.

8. The handle according to claim 6, wherein the body member is at least partly hollow, and wherein the at least one sliding member is received within the body member such that the first and second sliding member is axially movable relative to the body member.

9. The handle according to claim 8, wherein the body member is provided with a first and a second elongated hole each being parallel to the longitudinal axis of the operating handle, wherein the first pin member extends through the first elongated hole and the second pin member extends through the second elongated hole.

10. The handle according to claim 6, wherein the body member further comprises a portion fixed to the hand grip.

11. The handle according to claim 6, wherein the body member comprises a portion fixed to the hand grip that is cylindrical and has a diameter equal to or substantially equal to the outer diameter of the hollow cylindrical member, wherein the hand grip is at least partly disposed around the cylindrical portion of the body member such as to be concentrically and coaxially with the cylindrical portion.

12. The handle according to claim 6, wherein a surface of the cylindrical member guides an axial movement of the at least one sliding member relative to the body member.

13. The handle according to claim 1, wherein the operating handle is provided with a locking mechanism for subdividing a maximal available turning movement of the manipulating part when rotated relative to the hand grip.

14. The handle according to claim 6, wherein the locking mechanism comprises at least one locking recess provided in the cylindrical member of the cam mechanism and at least one engaging piece operatively connected with the body member, the at least one engaging piece being adapted to releasably engage with the at least one locking recess thereby preventing continuous rotation of the cylindrical member relative to the body member.

15. The handle according to claim 14, wherein the locking mechanism comprises an actuator for disengaging the engaging piece when the engaging piece engages with the at least one locking recess.

16. The handle according to claim 15, wherein the engaging piece is spring-loaded and wherein the actuator comprises a spring-loaded push-button operatively connected with the engaging piece, the push-button being designed to be pushed by the user for disengaging the engaging piece.

17. The handle according to claim 16, wherein the actuator further comprises a lever connected with the push-button for pressing the engaging piece down when the push-button is pushed down by the user.

18. The handle according to claim 17, wherein the actuator further comprises a driving piece having a first end section coupled to the lever by a pin such as to be pivotable in a plane perpendicular to the direction of pushing of the push-button, and further having a second end section for pressing the engaging piece down when the push-button is pushed down by the user.

19. The handle according to claim 18, wherein the driving piece is coupled to the lever, such that the driving piece swings out relative to the lever from a first position to a second position when the push-button is pushed down by the user and when the cylindrical member is simultaneously rotated relative to the body member, wherein the second end section of the driving piece loses contact with the engaging piece when the driving piece swings out relative to the lever to the second position.

20. The handle according to claim 19, wherein the actuator is configured to return the driving piece to the first position when the push-button is released.

* * * * *